US 9,403,846 B2

(12) United States Patent
Brodney et al.

(10) Patent No.: US 9,403,846 B2
(45) Date of Patent: Aug. 2, 2016

(54) CARBOCYCLIC- AND HETEROCYCLIC-SUBSTITUTED HEXAHYDROPYRANO[3,4-D][1,3]THIAZIN-2-AMINE COMPOUNDS

(71) Applicant: Pfizer Inc., New York, NY (US)

(72) Inventors: Michael Aaron Brodney, Newton, MA (US); Brian Thomas O'Neill, Haddam, CT (US); Christopher Ryan Butler, Canton, MA (US); Erik Alphie LaChapelle, Johnston, RI (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 14/653,549

(22) PCT Filed: Dec. 4, 2013

(86) PCT No.: PCT/IB2013/060633
§ 371 (c)(1),
(2) Date: Jun. 18, 2015

(87) PCT Pub. No.: WO2014/097038
PCT Pub. Date: Jun. 26, 2014

(65) Prior Publication Data
US 2016/0002264 A1    Jan. 7, 2016

Related U.S. Application Data

(60) Provisional application No. 61/739,053, filed on Dec. 19, 2012.

(51) Int. Cl.
C07D 513/04    (2006.01)

(52) U.S. Cl.
CPC .................................. *C07D 513/04* (2013.01)

(58) Field of Classification Search
CPC .................................................. C07D 513/04
USPC ........................................ 544/48; 514/224.2
See application file for complete search history.

(56) References Cited

U.S. PATENT DOCUMENTS

| 5,750,349 | A  | 5/1998  | Suzuki et al.   |
|-----------|-----|---------|-----------------|
| 7,115,600 | B2 | 10/2006 | Wager et al.    |
| 7,285,293 | B2 | 10/2007 | Castillo et al. |
| 7,975,664 | B2 | 7/2011  | Himsel et al.   |
| 8,158,620 | B2 | 4/2012  | Suzuki et al.   |
| 8,198,269 | B2 | 6/2012  | Motoki et al.   |
| 8,278,441 | B2 | 10/2012 | Mergott et al.  |
| 8,822,456 | B2 | 9/2014  | Brodney et al.  |
| 8,865,706 | B2 | 10/2014 | Brodney et al.  |
| 8,933,221 | B2 | 1/2015  | Brodney et al.  |
| 8,962,616 | B2 | 2/2015  | Brodney et al.  |
| 9,045,498 | B2 | 6/2015  | Brodney et al.  |
| 9,045,499 | B2 | 6/2015  | Brodney et al.  |
| 9,192,612 | B2 | 11/2015 | Brodney et al.  |
| 9,198,917 | B2 | 12/2015 | Brodney et al.  |
| 9,233,981 | B1 | 1/2016  | Brodney et al.  |
| 9,315,520 | B2 | 4/2016  | Brodney et al.  |
| 2003/0073655 | A1 | 4/2003  | Chain         |
| 2003/0195205 | A1 | 10/2003 | DeNinno et al. |
| 2004/0192898 | A1 | 9/2004  | Jia et al.     |
| 2004/0220186 | A1 | 11/2004 | Bell et al.    |
| 2005/0019328 | A1 | 1/2005  | Schenk et al.  |
| 2005/0043354 | A1 | 2/2005  | Wager et al.   |
| 2005/0048049 | A1 | 3/2005  | Schenk et al.  |
| 2005/0256135 | A1 | 11/2005 | Lunn et al.    |
| 2005/0267095 | A1 | 12/2005 | Bernardelli et al. |
| 2005/0267100 | A1 | 12/2005 | Elliott et al. |
| 2006/0057701 | A1 | 3/2006  | Rosenthal et al. |
| 2006/0106035 | A1 | 5/2006  | Hendrix et al. |
| 2006/0111372 | A1 | 5/2006  | Hendrix et al. |
| 2006/0178501 | A1 | 8/2006  | Summers et al. |

(Continued)

FOREIGN PATENT DOCUMENTS

| EP | 0994728 | 10/1998 |
| EP | 127584  | 10/2004 |

(Continued)

OTHER PUBLICATIONS

International Application No. PCT/IB2013/060456, filed Nov. 27, 2013, International Preliminary Report on Patentability, mailed Jun. 16, 2015, 5 pages.
International Application No. PCT/IB2013/060633, filed Dec. 4, 2013, International Preliminary Report on Patentability, mailed Jun. 23, 2015.
International Application No. PCT/IB2014/0558760 filed Feb. 3, 2014, International Preliminary Report on Patentability, mailed Aug. 18, 2015, 7 pages.
International Application No. PCT/IB2014/0558777 filed Feb. 4, 2014, International Preliminary Report on Patentability, mailed Aug. 18, 2015, 7 pages.

(Continued)

*Primary Examiner* — Kahsay Habte
(74) *Attorney, Agent, or Firm* — John A. Wichtowski

(57) ABSTRACT

The present invention provides compounds of formula I, wherein the variables $R^1$, $R^2$, $R^5$ and b are as defined in the specification. Corresponding pharmaceutical compositions, methods of treatment, methods of synthesis, and intermediates are also disclosed.

19 Claims, No Drawings

(56) References Cited

U.S. PATENT DOCUMENTS

| | | |
|---|---|---|
| 2007/0031416 A1 | 2/2007 | Shoji et al. |
| 2007/0160616 A1 | 7/2007 | Rosenthal et al. |
| 2007/0179175 A1 | 8/2007 | Lunn |
| 2008/0096955 A1 | 4/2008 | Wager et al. |
| 2008/0176925 A1 | 7/2008 | Butler et al. |
| 2009/0054482 A1 | 2/2009 | Chan et al. |
| 2010/0056618 A1 | 3/2010 | Mascitti et al. |
| 2010/0093999 A1 | 4/2010 | Motoki et al. |
| 2010/0285145 A1 | 11/2010 | Darout et al. |
| 2011/0027279 A1 | 2/2011 | Chain |
| 2011/0038861 A1 | 2/2011 | Rosenthal |
| 2011/0046122 A1 | 2/2011 | Andreini et al. |
| 2011/0207723 A1 | 8/2011 | Motoki et al. |
| 2012/0245155 A1 | 9/2012 | Yoshida et al. |
| 2013/0053373 A1 | 2/2013 | Brodney et al. |
| 2013/0296308 A1 | 11/2013 | Brodney et al. |
| 2015/0087637 A1 | 3/2015 | Brodney et al. |
| 2015/0133438 A1 | 5/2015 | Brodney et al. |
| 2015/0224110 A1 | 8/2015 | Brodney et al. |
| 2015/0231144 A1 | 8/2015 | Brodney et al. |
| 2015/0239908 A1 | 8/2015 | Brodney et al. |

FOREIGN PATENT DOCUMENTS

| | | |
|---|---|---|
| EP | 2332943 | 6/2011 |
| EP | 2511269 | 10/2012 |
| WO | 9844955 | 10/1998 |
| WO | 0220521 | 3/2002 |
| WO | 03072197 | 9/2003 |
| WO | 2004032868 | 4/2004 |
| WO | 2005025616 | 3/2005 |
| WO | 2005049616 | 11/2005 |
| WO | 2005116014 | 12/2005 |
| WO | 2006069081 | 6/2006 |
| WO | 2006118959 | 11/2006 |
| WO | 2006120552 | 11/2006 |
| WO | 2006126081 | 11/2006 |
| WO | 2006126082 | 11/2006 |
| WO | 2006126083 | 11/2006 |
| WO | 2006136924 | 12/2006 |
| WO | 2007063385 | 6/2007 |
| WO | 2007069053 | 6/2007 |
| WO | 2007088450 | 8/2007 |
| WO | 2007088462 | 9/2007 |
| WO | 2007099423 | 9/2007 |
| WO | 2007105053 | 9/2007 |
| WO | 2007122466 | 11/2007 |
| WO | 2007122482 | 11/2007 |
| WO | 2007138431 | 12/2007 |
| WO | 2008065508 | 6/2008 |
| WO | 2009016462 | 2/2009 |
| WO | 2009091016 | 7/2009 |
| WO | 2009144554 | 12/2009 |
| WO | 2009144555 | 12/2009 |
| WO | 2010013161 | 2/2010 |
| WO | 2010038686 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010140092 | 12/2010 |
| WO | 2011005611 | 1/2011 |
| WO | 2011071109 | 6/2011 |
| WO | 2012098461 | 7/2012 |
| WO | 2012162334 | 11/2012 |
| WO | 2013030713 | 3/2013 |
| WO | 2013164730 | 11/2013 |

OTHER PUBLICATIONS

International Application No. PCT/IB2015/052279, filed Mar. 27, 2015, International Search Report and Written Opinion, mailed Jun. 24, 2015, 10 pages.
International Patent Application No. PCT/IB2014/058777, filed Feb. 4, 2014, International Search Report and Written Opinion, mailed Mar. 25, 2014, 11 pages.
International Application No. PCT/IB2014/0558760 filed Feb. 3, 2014, International Search Report and Written Opinion, mailed Mar. 13, 2014, 10 pages.
International Patent Application PCT/IB2013/060633 filed Dec. 4, 2013, International Search Report and Written Opinion mailed Mar. 25, 2014, 12 pages.
Haan, J., et al., "Amyloid in Central Nervous System Disease", Clinical Neurology and Neurosurgery, 1990, pp. 305-310, 92(4).
Glenner, G., et al., "Amyloidosis of the Nervous System", Journal of Neurological Science, Dec. 1989, pp. 1-28, vol. 94.
Farah, M., et al., "Reduced BACE1 Activity Enhances Clearance of Myelin Debris and Regeneration of Axons in the Injured Peripheral Nervous System", Journal of Neuroscience, Apr. 13, 2011, pp. 5744-5754, 31(15).
Meakin, Paul, et al., "Reduction in BACE1 decreases body weight, protects against diet-induced obesity and enhances insulin sensitivity in mice", Biochemical Journal, Jan. 1, 2012, pp. 285-296, 441(1).
Esterhazy, Daria, et al., "BACE2 Is a β Cell-Enriched Protease that Regulates Pancreatic β Cell Function and Mass", Cell Metabolism, Sep. 2011, pp. 365-377, 14(3).
Zimmet, P.Z. et al., "The Metabolic Syndrome: Perhaps an Etiologic Mystery but Far From a Myth—Where Does the International Diabetes Federation Stand?," Medscape Diabetes & Endocrinology, Oct. 11, 2005, 8 pages, www.medscape.com, 7(2).
Alberti, K.G. et al., "The Metabolic Syndrome—A New Worldwide Definition," Lancet, Sep. 24-30, 2005, pp. 1059-1062, 366(9491).
Haleblian, John K., "Characterization of Habits and Crystalline Modification of Solids and Their Pharmaceutical Applications", Journal Pharmaceutical Sciences, Aug. 1975, pp. 1269-1288, 64(8).
Finnin, Barrie, et al., "Transdermal Penetration Enhancers Applications, Limitations, and Potential", Journal Pharmaceutical Sciences, Oct. 1999, pp. 955-958, 88(10).
Zhang, S. et al., "PTP1B as a Drug Target: Recent Developments in PTP1B Inhibitor Discovery", Drug Discovery Today, May 2007, pp. 373-381, 12(9/10).
Chao, Edward, et al., "SGLT2 Inhibition—A Novel Strategy for Diabetes Treatment", Nature Reviews Drug Discovery, Jul. 2010, pp. 551-559, 9(7).
Demong, D.E. et al., "Chapter 8, Glucagon Receptor Antagonists for Type II Diabetes", Annual Reports in Medicinal Chemistry 2008, pp. 119-137, vol. 43.
Jones, R.M. et al., "Chapter 7, The Emergence of GPR119 Agonists as Anti-Diabetic Agents", Annual Reports in Medicinal Chemistry 2009, pp. 149-170, vol. 44.
Zhong, M., "TGR5 as a Therapeutic Target for Treating Obesity", Current Topics in Medicinal Chemistry, 2010, pp. 386-396, 10(4).
Medina, J.C., et al., "Chapter 5, GPR40 (FFAR1) Modulators", Annual Reports in Medicinal Chemistry 2008, pp. 75-85, vol. 43.
Carpino, P.A., et al., "Diabetes Area Participation Analysis: A Review of Companies and Targets Described in the 2008-2010 Patent Literature", Expert Opinion on Therapeutic Patents, Dec. 2010, pp. 1627-1651, 20(12).
Spek, A.L., "Single-Crystal Structure Validation with the Program PLATON", Journal of Applied Crystallography, Feb. 2003, pp. 7-13, 36(1).
Macrae, Clare, et al., "Mercury: Visualization and Analysis of Crystal Structures", Journal of Applied Crystallography, Jun. 2006, pp. 453-457, 39(3).
Hooft, Rob, et al., "Determination of Absolute Structure Using Bayesian Statistics on Bijvoet differences", Journal of Applied Crystallography, Feb. 2008, pp. 96-103, 41(1).
Flack, H.D., "On Enantiomorph-Polarity Estimation", Acta Cryst., 1983, pp. 876-881, vol. A39.
England, et al., "An Improved Synthesis of a Novel α1A Partial Agonist Including a New Two-Step Synthesis of 4-Fluoropyrazole", Tetrahedron Letters, May 26, 2010, pp. 2849-2851, 51(21).
Kharitonenkov, A. et al., "FGF21: A Novel Prospect for the Treatment of Metabolic Diseases", Current Opinion in Investigational Drugs, Apr. 2009, pp. 359-364, 10(4).
Denmark, S.E, et al., "Allylation of Carbonyls: Methodology and Stereochemistry", Modern Carbonyl Chemistry, 2000, Chapter 10, pp. 299-401.

(56) References Cited

OTHER PUBLICATIONS

Miyaura, N., et al., "Palladium-Catalyzed Cross-Coupling Reactions of Organoborn Compounds", Chemical Review, Nov. 1995, pp. 2457-2483, 95(7).

Olsen, R., et al., "Secretase Inhibitors and Modulators for the Treatment of Alzheimer's Disease", Annual Reports in Medicinal Chemistry, 2007, pp. 27-47, vol. 42.

International Application No. PCT/IB2012/054198, filed Aug. 17, 2012, International Search Report and Written Opinion, mailed Jan. 23, 2013, 14 pages.

Sheppeck, J.E. II, et al., "A Convenient and Scaleable Procedure for Removing the Fmoc Group in Solution", Tetrahedron Letters, 2000, pp. 5329-5333, vol. 41(28).

Suzuki, Akira, "Recent advances in the cross-coupling reactions of organoboron derivatives with organic electrophiles 1995-1998", Journal Organometallic Chemistry, 1999, pp. 147-168, vol. 576.

International Application No. PCT/IB2013/053178, filed Apr. 22, 2013, International Written Opinion and Search Report, mailed Jul. 3, 2013, 10 pages.

English equivalent U.S. Pat. No. 8,158,620; Suzuki, et al., filed Jan. 16, 2009 for WO 2009091016, published Jun. 23, 2007.

International Application No. PCT/IB2013/058402, filed Sep. 9, 2013, International Search Report and Written Opinion, mailed Dec. 16, 2013, 11 pages.

International Application No. PCT/IB2013/060456, filed Nov. 27, 2013, International Search Report, mailed Feb. 21, 2014, 8 pages.

PCT/IB2013/060633 application filed Dec. 4, 2013.

PCT/IB2013/058402 application filed Sep. 9, 2013.

PCT/IB2013/060456 application filed Nov. 27, 2013.

PCT/IB2014/058760 application filed Feb. 3, 2014.

PCT/IB2014/058777 application filed Feb. 4, 2014.

Guidance for Industry, Q3C—Tables and List, U.S. Department of Health and Human Services, Food and Drug Administration, Center for Drug Evaluation and Research (CDER), Center for Biologics Evaluation and Research (CBER), Nov. 2003, ICH, Revision I.

CARBOCYCLIC- AND HETEROCYCLIC-SUBSTITUTED HEXAHYDROPYRANO[3,4-D][1,3]THIAZIN-2-AMINE COMPOUNDS

This application is a national stage application under 35 U.S.C. 371 of PCT/IB2013/060633, filed on Dec. 4, 2013, which claims the benefit of U.S. Provisional Patent Application No. 61/739,053, filed on Dec. 19, 2012, the disclosures of which is hereby incorporated by reference in their entirety.

FIELD OF THE INVENTION

The present invention relates to small molecule compounds and pharmaceutically acceptable salts thereof that are inhibitors of β-site amyloid precursor protein (APP) Cleaving Enzyme 1 (BACE1) and inhibitors of BACE2. This invention relates to inhibiting the production of A-beta peptides that can contribute to the formation of neurological deposits of amyloid protein. The present invention also relates to the treatment of Alzheimer's Disease (AD) and other neurodegenerative and/or neurological disorders, as well as the treatment of diabetes in mammals, including humans. More particularly, this invention relates to thioamidine compounds and pharmaceutically acceptable salts thereof useful for the treatment of neurodegenerative and/or neurological disorders, such as AD and Down's Syndrome, related to A-beta peptide production.

BACKGROUND OF THE INVENTION

Dementia results from a wide variety of distinctive pathological processes. The most common pathological processes causing dementia are Alzheimer's disease ("AD"), cerebral amyloid angiopathy ("CM") and prion-mediated diseases (see, e.g., Haan et al., Clin. Neurol. Neurosurg. 1990, 92(4): 305-310; Glenner et al., J. Neurol. Sci. 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050.

The accumulation of amyloid-β (Aβ peptides) is believed to be one of the underlying causes of Alzheimer's Disease (AD), which is the most common cause of cognitive decline in the elderly (Hardy & Allsop, Trends Pharmacol Sci 1991; 12(10):383-8; Selkoe, Behav Brain Res 2008; 192(1):106-13). Aβ, the major protein constituent of amyloid plaques, is derived from sequential cleavage of amyloid precursor protein (APP), a type I integral membrane protein, by two proteases, β- and γ-secretase. Proteolytic cleavage of APP by the β-site APP cleaving enzymes (BACE1 and BACE2) generates a soluble N-terminal ectodomain of APP (sAPPβ) and the C-terminal fragment C99. Subsequent cleavage of the membrane-bound C99 fragment by the γ-secretase liberates the various Aβ peptide species, of which Aβ40 and Aβ42 are the most predominant forms (Vassar et al., J Neurosci 2009; 29(41):12787-94; Marks & Berg, Neurochem Res 2010; 35:181-210). Therefore, limiting the generation of Aβ directly through inhibition of BACE1 is one of the most attractive approaches for the treatment of AD, as BACE1 inhibitors could effectively inhibit the formation of all predominant Aβ peptides.

In addition, it has been determined that BACE1 knock-out mice had markedly enhanced clearance of axonal and myelin debris from degenerated fibers, accelerated axonal regeneration, and earlier reinnervation of neuromuscular junctions compared with littermate controls. These data suggest BACE1 inhibition as a therapeutic approach to accelerate regeneration and recovery after peripheral nerve damage. (See Farah et al., J. Neurosci., 2011, 31(15): 5744-5754).

Insulin resistance and impaired glucose homoeostasis are important indicators of Type 2 diabetes and are early risk factors of AD. In particular, there is a higher risk of sporadic AD in patients with Type 2 diabetes and AD patients are more prone to Type 2 diabetes (Butler, Diabetes 53:474-481, 2004.). Recently, it has also been proposed that AD should be reconsidered as Type 3 Diabetes (de la Monte, J Diabetes Sci Technol 2008; 2(6):1101-1113). Of special interest is the fact that AD and Type 2 diabetes share common pathogenic mechanisms and possibly treatments (Park S A, J Clin Neurol 2011; 7:10-18; Raffa, Br J Clin Pharmacol 2011/71:3/365-376). Elevated plasma levels of Aβ, the product of BACE activities, were recently associated with hyperglycemia and obesity in humans (see Meakin et al., Biochem J. 2012, 441 (1):285-96; Martins, Journal of Alzheimer's Disease 8 (2005) 269-282). Moreover, increased Aβ production prompts the onset of glucose intolerance and insulin resistance in mice (Cózar-Castellano, Am J Physiol Endocrinol Metab 302: E1373-E1380, 2012; Delibegovic, Diabetologia (2011) 54:2143-2151). Finally, it is also suggested that circulating Aβ could participate in the development of atherosclerosis in both humans and mice (De Meyer, Atherosclerosis 216 (2011) 54-58; Catapano, Atherosclerosis 210 (2010) 78-87; Roher, Biochimica et Biophysica Acta 1812 (2011) 1508-1514).

Therefore, it is believed that BACE1 levels may play a critical role in glucose and lipid homoeostasis in conditions of chronic nutrient excess. Specifically, BACE1 inhibitors may be potentially useful for increasing insulin sensitivity in skeletal muscle and liver as illustrated by the fact that reduction in BACE1 decreases body weight, protects against diet-induced obesity and enhances insulin sensitivity in mice (see Meakin et al., Biochem J. 2012, 441(1):285-96). Of equal interest is the identification of LRP1 as a BACE1 substrate and the potential link to atherosclerosis (Strickland, Physiol Rev 88: 887-918, 2008; Hyman, J. Biol. Chem. Vol. 280, No. 18, 17777-17785, 2005).

Likewise, inhibition of BACE2 is proposed as a treatment of Type 2 diabetes with the potential to preserve and restore β-cell mass and stimulate insulin secretion in pre-diabetic and diabetic patients (WO2011/020806). BACE2 is a β-cell enriched protease that regulates pancreatic β cell function and mass and is a close homologue of BACE1. Pharmacological inhibition of BACE2 increases β-cell mass and function, leading to the stabilization of Tmem27. (See Esterhazy et al., Cell Metabolism 2011, 14(3): 365-377). It is suggested that BACE2 inhibitors are useful in the treatment and/or prevention of diseases associated with the inhibition of BACE2 (WO2011/020806).

Aminodihydrothiazine or thioamidine compounds are described in WO 2009/091016 and WO 2010/038686 as useful inhibitors of the β-secretase enzyme. Co-pending PCT application, PCT/IB2012/054198, filed by Pfizer Inc on Aug. 17, 2012, also describes aminodihydrothiazine compounds that are useful inhibitors of the β-secretase enzyme. The present invention is directed to novel thioamidine compounds and their use in the treatment of neurodegenerative diseases, including AD, as well as the treatment of metabolic diseases and conditions such as diabetes and obesity.

SUMMARY OF THE INVENTION

The present invention is directed to compounds having the structure of formula I:

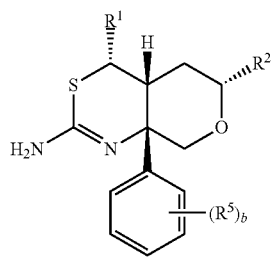

I or a tautomer thereof or a pharmaceutically acceptable salt of said compound or tautomer, wherein:

$R^1$ is selected from hydrogen, —$CH_3$, —$CH_2F$, —$CHF_2$, —$CF_3$, or —$CH_2OCH_3$;

$R^2$ is —$(C(R^{3a})(R^{3b}))_m$—$(C_3-C_6)$cycloalkyl or —$(C(R^{3a})(R^{3b}))_m$— (4- to 10-membered) heterocycloalkyl having one to three heteroatoms independently selected from N, O or S, wherein said N is optionally substituted with $R^4$; and wherein each available carbon position of said $(C_3-C_6)$cycloalkyl moiety or said (4- to 10-membered)heterocycloalkyl moiety is optionally substituted with one to two $R^6$;

$R^{3a}$ and $R^{3b}$ are each independently hydrogen, fluoro, or $(C_1-C_6)$alkyl; wherein said $(C_1-C_6)$alkyl is optionally substituted with one to three fluoro;

$R^4$ is selected from $(C_1-C_6)$alkyl, $(C_1-C_6)$alkylcarbonyl, $(C_3-C_6)$cycloalkylcarbonyl or $(C_1-C_6)$alkylcarbonyl$(C_1-C_6)$alkyl; wherein said $(C_1-C_6)$alkyl moiety, said $(C_1-C_6)$alkylcarbonyl moiety and said $(C_1-C_6)$alkylcarbonyl$(C_1-C_6)$alkyl moiety are optionally substituted with one to three fluoro;

$R^5$ at each occurrence is independently halogen, $(C_1-C_3)$alkyl, and $(C_1-C_3)$alkoxy, wherein said $(C_1-C_3)$alkyl moiety and said $(C_1-C_3)$alkoxy are optionally substituted with one to three fluoro;

$R^6$ at each occurrence is independently halogen, —OH, —CN, $(C_1-C_6)$alkyl, and $(C_1-C_6)$alkoxy, wherein said $(C_1-C_6)$alkyl or $(C_1-C_6)$alkoxy is optionally substituted with one to three fluoro;

m is 0, 1, or 2; and b is 0, 1, 2, 3, 4, or 5.

The present invention is further directed to compounds of formula I, or a tautomer thereof or a pharmaceutically acceptable salt of said compound or tautomer, wherein the compound is selected from:

(4aR,6R,8aS)-8a-(2,4-Difluorophenyl)-6-(tetrahydrofuran-2-yl)-4,4a,5,6,8,8a-hexahydropyrano[3,4-d][1,3]thiazin-2-amine;

(4aR,6R,8aS)-6-Cyclopropyl-8a-(2,4-difluorophenyl)-4,4a,5,6,8,8a-hexahydropyrano[3,4-d][1,3]thiazin-2-amine;

(4R,4aR,6R,8aS)-6-Cyclopropyl-8a-(2,4-difluorophenyl)-4-methyl-4,4a,5,6,8,8a-hexahydropyrano[3,4-d][1,3]thiazin-2-amine;

(4aR,6R,8aS)-8a-(2,4-Difluorophenyl)-6-(oxetan-2-yl)-4,4a,5,6,8,8a-hexahydropyrano[3,4-d][1,3]thiazin-2-amine;

rel-(4S,4aR,6R,8aS)-6-Cyclopropyl-8a-(2,4-difluorophenyl)-4-(methoxymethyl)-4,4a,5,6,8,8a-hexahydropyrano[3,4-d][1,3]thiazin-2-amine;

(4S,4aR,6R,8aS)-6-Cyclopropyl-8a-(2,4-difluorophenyl)-4-(fluoromethyl)-4,4a,5,6,8,8a-hexahydropyrano[3,4-d][1,3]thiazin-2-amine;

(4aR,6R,8aS)-8a-(2,4-Difluorophenyl)-6-(1-methylcyclopropyl)-4,4a,5,6,8,8a-hexahydropyrano[3,4-d][1,3]thiazin-2-amine;

(4aR,6S,8aS)-6-(Cyclopropylmethyl)-8a-(2,4-difluorophenyl)-4,4a,5,6,8,8a-hexahydropyrano[3,4-d][1,3]thiazin-2-amine;

(4aR,6R,8aS)-6-Cyclopropyl-8a-(2,4,6-trifluorophenyl)-4,4a,5,6,8,8a-hexahydropyrano[3,4-d][1,3]thiazin-2-amine;

(4aR,6R,8aS)-6-Cyclopropyl-8a-(4-fluorophenyl)-4,4a,5,6,8,8a-hexahydropyrano[3,4-d][1,3]thiazin-2-amine;

(4aR,6R,8aS)-6-Cyclopropyl-8a-(2,5-difluorophenyl)-4,4a,5,6,8,8a-hexahydropyrano[3,4-d][1,3]thiazin-2-amine;

(4aR,6R,8aS)-6-Cyclopropyl-8a-(2,6-difluorophenyl)-4,4a,5,6,8,8a-hexahydropyrano[3,4-d][1,3]thiazin-2-amine;

(4aR,6R,8aS)-6-Cyclopropyl-8a-(2-fluorophenyl)-4,4a,5,6,8,8a-hexahydropyrano[3,4-d][1,3]thiazin-2-amine;

(4aR,6R,8aS)-6-Cyclopropyl-8a-phenyl-4,4a,5,6,8,8a-hexahydropyrano[3,4-d][1,3]thiazin-2-amine;

(4aR,6R,8aS)-6-Cyclopropyl-8a-(2-fluoro-4-methylphenyl)-4,4a,5,6,8,8a-hexahydropyrano[3,4-d][1,3]thiazin-2-amine;

(4aR,6R,8aS)-6-Cyclopropyl-8a-(3-fluoro-4-methylphenyl)-4,4a,5,6,8,8a-hexahydropyrano[3,4-d][1,3]thiazin-2-amine;

(4aR,6R,8aS)-8a-(2,4-Difluorophenyl)-6-(5,5-dimethyltetrahydrofuran-2-yl)-4,4a,5,6,8,8a-hexahydropyrano[3,4-d][1,3]thiazin-2-amine;

(4aR,6R,8aS)-8a-(2,4-Difluorophenyl)-6-[(1R,2R)-2-methylcyclopropyl]-4,4a,5,6,8,8a-hexahydropyrano[3,4-d][1,3]thiazin-2-amine; and (4aR,6R,8aS)-8a-(2,4-Difluorophenyl)-6-[(2S)-tetrahydrofuran-2-yl]-4,4a,5,6,8,8a-hexahydropyrano[3,4-d][1,3]thiazin-2-amine.

The present invention is also directed to a pharmaceutical composition comprising compounds of formula I, or a tautomer thereof or a pharmaceutically acceptable salt of said compound or tautomer, or a solvate thereof, and a pharmaceutically acceptable excipient, e.g., vehicle, diluent or carrier. The pharmaceutical composition described herein can be administered in a therapeutically effective amount to a mammal, including a human, in need thereof for any or all of the following:

(1) inhibiting production of amyloid-β protein and for inhibiting beta-site amyloid precursor protein cleaving enzyme 1 (BACE1);

(2) treating neurodegenerative disease and, in particular, Alzheimer's Disease;

(3) inhibiting BACE1 and/or BACE2 activity for the therapeutic and/or prophylactic treatment of diseases and disorders characterized by elevated β-amyloid levels, including diabetes or type 2 diabetes;

(4) increasing insulin sensitivity in skeletal muscle and liver in a mammal, including humans; and (5) treating and/or preventing obesity.

The present invention is also directed to the compound of formula I, or tautomer thereof or pharmaceutically acceptable salt of said compound or tautomer, wherein the compound is selected from the compounds described in Examples 1-16 and 19-21.

The present invention is also directed to methods of inhibiting BACE2 enzyme activity, by administering a therapeutically effective amount of a thioamidine compound of any of the embodiments of formula I, or tautomer thereof or pharmaceutically acceptable salt of said compound or tautomer, and a pharmaceutically acceptable excipient, to a mammal or a patient in need thereof.

The present invention is further directed to methods for treating conditions or diseases of the central nervous system and neurological disorders in which the β-secretase enzyme is involved (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment ("MCI")); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema), nerve injury treatment (including accelerating regeneration and recovery after peripheral nerve damage) and pediatric psychiatric disorders (including attention deficit disorder, attention deficit/hyperactive disorder, conduct disorder, and autism) in a mammal, preferably a human, comprising administering to said mammal a therapeutically effective amount of a compound of formula I or pharmaceutically acceptable salt thereof. The compounds of formula I may also be useful for improving memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress.

The present invention is further directed to:

(1) Methods for treating a neurological disorder (such as migraine; epilepsy; Alzheimer's disease; Parkinson's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of formula I or pharmaceutically acceptable salt thereof;

(2) Methods for the treatment (e.g., delaying the progression or onset) of diabetes or diabetes-related disorders including Type 1 and Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy;

(3) Methods for the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on metabolic syndrome, see, e.g., Zimmet, P. Z. et al., "The Metabolic Syndrome: Perhaps an Etiologic Mystery but Far From a Myth—Where Does the International Diabetes Federation Stand?," Medscape Diabetes & Endocrinology, 7(2), (2005); and Alberti, K. G. et al., "The Metabolic Syndrome—A New Worldwide Definition," *Lancet*, 366, 1059-62 (2005);

(4) Methods for the treatment of nonalcoholic fatty liver disease (NAFLD) and hepatic insulin resistance; and (5) Combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided.

As used herein, "eating disorders" refer to illnesses in which the patient suffers disturbances in his/her eating behaviors and related thoughts and emotions. Representative examples of obesity-related eating disorders include overeating, bulimia, binge-eating disorder, compulsive dieting, nocturnal sleep-related eating disorder, pica, Prader-Willi syndrome, and night-eating syndrome.

Other features and advantages of this invention will be apparent from this specification and the appendent claims which describe the invention.

DETAILED DESCRIPTION OF THE INVENTION

The headings within this document are only being utilized to expedite its review by the reader. They should not be construed as limiting the invention or claims in any manner.

Definitions and Exemplifications

As used throughout this application, including the claims, the following terms have the meanings defined below, unless specifically indicated otherwise. The plural and singular should be treated as interchangeable, other than the indication of number:

The term "$(C_1-C_6)$alkyl" refers to a linear or branched-chain saturated hydrocarbyl substituent (i.e., a substituent obtained from a hydrocarbon by removal of a hydrogen) containing from 1 to 6 carbon atoms. Examples of such substituents include methyl, ethyl, propyl (including n-propyl and isopropyl), butyl (including n-butyl, isobutyl, sec-butyl and tert-butyl), n-pentyl, isopentyl, neopentyl, and n-hexyl.

The term "$(C_1-C_3)$alkyl" refers to a linear or branched-chain saturated hydrocarbyl substituent (i.e., a substituent obtained from a hydrocarbon by removal of a hydrogen)

containing from 1 to 3 carbon atoms. Examples of such substituents include methyl, ethyl, and propyl (including n-propyl and isopropyl) and the like.

The term "($C_1$-$C_6$)alkoxy" as used herein, means a ($C_1$-$C_6$) alkyl group, as defined herein, appended to the parent molecular moiety through an oxygen atom. Examples include, but are not limited to, methoxy, ethoxy, and n-propoxy, isopropoxy, butoxy, sec-butoxy, tert-butoxy, pentyloxy, hexyloxy and the like.

The term "carbonyl" as used herein, means a —C(O)— group.

The term "($C_1$-$C_6$)alkylcarbonyl" as used herein, means a ($C_1$-$C_6$)alkyl group, as defined herein, appended to the parent molecular moiety through a carbonyl group, as defined herein. Representative examples of ($C_1$-$C_6$)alkylcarbonyl include, but are not limited to, acetyl, 1-oxopropyl, 2,2-dimethyl-1-oxopropyl, 1-oxobutyl, and 1-oxopentyl and the like.

The term "($C_1$-$C_6$)alkylcarbonyl($C_1$-$C_6$)alkyl" as used herein, means a ($C_1$-$C_6$)alkylcarbonyl group, as defined herein, appended to the parent molecular moiety through a ($C_1$-$C_6$)alkyl group, as defined herein. Representative examples of (C1-C6)alkylcarbonyl($C_1$-$C_6$)alkyl include, but are not limited to, 2-oxopropyl, 3,3-dimethyl-2-oxopropyl, 3-oxobutyl, and 3-oxopentyl.

The term "($C_3$-$C_6$)cycloalkyl" refers to a saturated or partially saturated monocyclic, bicyclic, bridged bicyclic or tricyclic alkyl radical wherein each cyclic moiety has 3 to 6 carbon atoms. Examples include cyclopropyl, cyclobutyl, cyclopentyl, cyclohexyl and the like.

The term "4- to 10-membered heterocycloalkyl" refers to a substituent obtained by removing a hydrogen from a saturated or partially saturated ring structure containing a total of 4 to 10 ring atoms, wherein at least one of the ring atoms is a heteroatom selected from oxygen, nitrogen, or sulfur. A heterocycloalkyl alternatively may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is bound to the group may be the at least one heteroatom when the heteroatom is nitrogen, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom when the heteroatom is nitrogen, or it may be bound to a ring carbon atom, where the ring carbon atom may be in the same ring as the at least one heteroatom or where the ring carbon atom may be in a different ring from the at least one heteroatom. Non-limiting examples of heterocycloalkyls include, but are not limited to, azetidinyl, pyrrolidinyl, piperidinyl, azepinyl, piperazinyl, 1,2,3,6-tetrahydropyridinyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0] heptanyl, quinolizinyl, quinuclidinyl, 1,4-dioxaspiro[4.5] decyl, 1,4-dioxaspiro[4.4]nonyl, 1,4-dioxaspiro[4.3]octyl, and 1,4-dioxaspiro[4.2]heptyl.

The term "cyano" (also referred to as "nitrile") means —CN.

The term "hydrogen" refers to a hydrogen substituent, and may be depicted as —H.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "halo" or "halogen" refers to fluorine (which may be depicted as —F), chlorine (which may be depicted as —Cl), bromine (which may be depicted as —Br), or iodine (which may be depicted as —I).

The term "methoxy" refers to a substituent consisting of a methyl group bound to an oxygen, and may be depicted as —$OCH_3$.

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

This specification uses the terms "substituent," "radical," and "group" interchangeably.

If substituents are described as being "independently selected" from a group, each instance of a substituent is selected independent of the other. Each substituent therefore may be identical to or different from the other substituent(s).

As used herein the terms "formula I", "formula Ia", "formula Ib", "formula Ic", and "formula Id", may be hereinafter referred to as a "compound(s) of the invention." Such terms are also defined to include all forms of the compound of formulas I, Ia, Ib, Ic and Id including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (———) a solid wedge ( ◂▬▬ ), or a dotted wedge ( ⸱⸱⸱⸱⸱⸱⸱ ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry are marked with (+/−). For example, unless stated otherwise, it is intended that the compounds of the invention can exist as stereoisomers, which include cis and trans isomers, optical isomers such as R and S enantiomers, diastereomers, geometric isomers, rotational isomers, conformational isomers, and mixtures thereof (such as racemates and diastereomeric pairs). The compounds of the invention may exhibit more than one type of isomerism. Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomenon of tautomerism and are regarded as compounds of the invention. For example, the compounds of the invention may exist in several tautomeric forms, including the 2-amino-dihydrothiazine form, Ia, and the 2-imino-tetrahydrothiazine form, Ib. All such tautomeric forms, and mixtures thereof, are included within the scope of compounds of the invention. Tautomers exist as mixtures of a tautomeric set in solution. In solid form, usually one tautomer predominates. Even though one tautomer may be described, the present invention includes all tautomers of the compounds of the invention and salts thereof. Examples of tautomers are described by the compounds of formula Ia and Ib and, collectively and generically, are referred to as compounds of formula I.

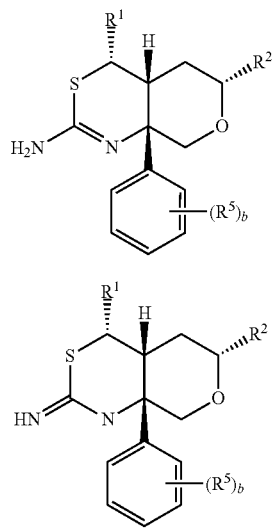

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of formula I with an acid whose anion, or a base whose cation, is generally considered suitable for human consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalenesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulphate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and W. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of formula I with certain moieties known to those skilled in the art as "promoieties" as described, for example, in "Design of Prodrugs" by H Bundgaard (Elsevier, 1985).

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine and chlorine, such as $^2$H, $^3$H, $^{13}$C, $^{11}$C, $^{14}$C, $^{15}$N, $^{18}$O, $^{17}$O, $^{32}$P, $^{35}$S, $^{18}$F, and $^{36}$Cl, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out the procedures disclosed in the Schemes and/or in the Examples and Preparations below, by substituting a readily available isotopically labeled reagent for a non-isotopically labeled reagent.

Compounds

To further elucidate the compounds of the present invention, the following subgenuses are described below.

Formula Ic depicted below is a subset of formula I as depicted, wherein the phenyl ring contains fluorine atoms at the 2- and 4-positions and an $R^{5a}$ substituent at the 6-position of the phenyl ring, wherein $R^{5a}$ is selected from hydrogen, fluoro or $(C_1-C_3)$alkyl.

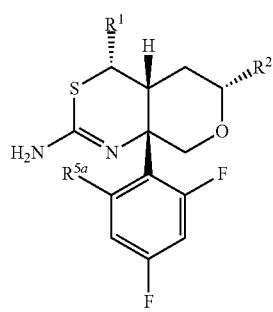

Ic

In certain embodiments of formula Ic, $R^1$ is hydrogen, —CH$_3$, —CH$_2$F, or —CH$_2$OCH$_3$ and $R^2$ is —(C(R$^{3a}$)(R$^{3b}$))$_m$—(C$_3$-C$_6$)cycloalkyl or —(C(R$^{3a}$)(R$^{3b}$))$_m$— (4- to 5-membered) heterocycloalkyl having one to two heteroatoms selected from N, O or S, wherein said N is optionally substituted with $R^4$; and $R^4$ is $(C_1-C_3)$alkyl; wherein said $(C_3-C_6)$cycloalkyl moiety or said (4- to 10-membered)heterocycloalkyl moiety is optionally substituted with one to three $R^6$; wherein $R^6$ is $(C_1-C_3)$alkyl; and $R^{5a}$ is hydrogen. In certain embodiments $R^1$ is hydrogen.

In certain embodiments of formula Ic, $R^1$ is hydrogen; $R^2$ is $(C_3-C_6)$cycloalkyl wherein said cycloalkyl is cyclopropyl optionally substituted with one $R^6$, wherein $R^6$ is methyl; and $R^{5a}$ is hydrogen. In certain embodiments $R^1$ is methyl. In certain embodiments $R^1$ is methoxymethyl. In certain embodiments $R^1$ is fluoromethyl. In certain embodiments of formula Ic, $R^2$ is 2-methylcyclopropyl. In certain embodiments of formula Ic, $R^2$ is cyclopropylmethyl.

In certain other embodiments $R^1$ is hydrogen; $R^2$ is a 4- to 5-membered heterocycloalkyl, wherein said heterocycloalkyl is tetrahydrofuranyl; and $R^{5a}$ is hydrogen. In certain embodiments said heterocycloalkyl is 5,5-dimethyltetrahydrofuranyl. In certain embodiments said heterocycloalkyl is oxetanyl.

In another embodiment of formula Ic, $R^{5a}$ is fluoro; $R^1$ is methyl; and $R^2$ is cyclopropyl.

Formula Id depicted below is a subset of formula I, wherein the phenyl ring contains a fluoro at the 2-position and an optional $R^5$ substituent at the 3-, 4-, 5- or 6-position of the phenyl ring.

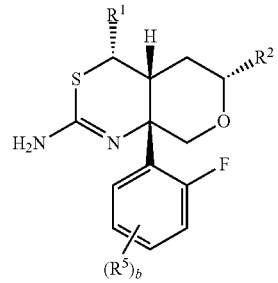

Id

In certain embodiments of formula Id, b is 1; $R^5$ is fluoro attached to the 3-, 5-, or 6-position of the phenyl ring; $R^1$ is hydrogen and $R^2$ is —(C(R$^{3a}$)(R$^{3b}$))$_m$—(C$_3$-C$_6$)cycloalkyl or —(C(R$^{3a}$)(R$^{3b}$))$_m$— (4- to 5-membered) heterocycloalkyl having at least one to two heteroatoms selected from N, O or S, wherein said N is optionally substituted with $R^4$; and $R^4$ is $(C_1-C_3)$alkyl; wherein said $(C_3-C_6)$cycloalkyl moiety or said (4- to 5-membered)heterocycloalkyl moiety is optionally substituted with one to three $R^6$; and $R^6$ is $(C_1-C_3)$alkyl. In certain embodiments of formula Id, $R^2$ is cyclopropyl. In certain embodiments of formula Id, wherein $R^5$ is fluoro, said fluoro is attached at the 5-position of the phenyl ring. In another embodiment, wherein $R^5$ is fluoro, said fluoro is attached at the 6-position of the phenyl ring. In certain other embodiments $R^5$ is methyl attached at the 4-position of the phenyl ring.

In another embodiment of formula Id, b is 0; $R^1$ is hydrogen and $R^2$ is cyclopropyl.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the condition are readily ascertained by one of ordinary skill in the art using preclinical and clinical approaches familiar to the medicinal arts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable excipient(s). The excipinet can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug excipients. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of the invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a BACE inhibitor compound as provided in the present invention and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the present invention or a tautomer thereof or a pharmaceutically acceptable salt of the compound or tautomer; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, without limitation:

(i) anti-obesity agents (including appetite suppressants), including gut-selective MTP inhibitors (e.g., dirlotapide, mitratapide, implitapide, and CAS No. 913541-47-6), CCKa agonists (e.g., N-benzyl-2-[4-(1H-indol-3-ylmethyl)-5-oxo-1-phenyl-4,5-dihydro-2,3,6,10b-tetraazabenzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonists (e.g., compounds described in U.S. Pat. No. 6,818,658), lipase inhibitors (e.g., Cetilistat), $PYY_{3-36}$ (as used herein "$PYY_{3-36}$" includes analogs, such as peglated $PYY_{3-36}$, e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine.

(ii) anti-diabetic agents, such as an acetyl-CoA carboxylase (ACC) inhibitor as described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a monoacylglycerol O-acyltransferase inhibitor, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPAR γ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S. et al., Drug Discovery Today, 12(9/10), 373-381 (2007)), a SIRT-1 inhibitor (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secretagogue, a fatty acid oxidation inhibitor, an A2 antagonist, a c-jun amino-terminal kinase (JNK) inhibitor, a glucokinase activator (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g., GSK1362885), a VPAC2 receptor agonist, an SGLT2 inhibitor, such as those described in E. C. Chao et al., Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211, as well as those in WO2010023594, a glucagon receptor modulator such as those described in Demong, D. E. et al., Annual Reports in Medicinal Chemistry 2008, 43, 119-137, a GPR119 modulator, particularly an agonist, such as those described in WO2010140092, WO2010128425, WO2010128414, WO2010106457, Jones, R. M. et al., Medicinal Chemistry 2009, 44, 149-170 (e.g., MBX-2982, GSK1292263, APD597 and PSN821), an FGF21 derivative or an analog such as those described in Kharitonenkov, A. et al., Current Opinion in Investigational Drugs 2009, 10(4), 359-364, TGR5 (also termed GPBAR1) receptor modulators, particularly agonists, such as those described in Zhong, M., Current Topics in Medicinal Chemistry 2010, 10(4), 386-396 and INT777, a GPR40 agonist, such as those described in Medina, J. C., Annual Reports in Medicinal Chemistry 2008, 43, 75-85, including but not limited to TAK-875, a GPR120 modulator, particularly an agonist, a high affinity nicotinic acid receptor (HM74A) activator, and an SGLT1 inhibitor, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors (e.g., SSTR1, SSTR2, SSTR3 and SSTR5), inhibitors or modulators of PDHK2 or PDHK4, inhibitors of MAP4K4, modulators of IL1 family including IL1beta, and modulators of RXRalpha. In addition, suitable anti-diabetic agents include mechanisms listed by Carpino, P. A., Goodwin, B. Expert Opin. Ther. Pat, 2010, 20(12), 1627-51;

(iii) anti-hyperglycemic agents, for example, those described at page 31, line 31 through page 32, line 18 of WO 2011005611;

(iv) lipid lowering agents (for example, those described at page 30, line 20 through page 31, line 30 of WO 2011005611), and anti-hypertensive agents (for example, those described at page 31, line 31 through page 32, line 18 of WO 2011005611);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as $A\beta_{1-15}$ conjugated to pan HLA DR-binding epitope (PADRE®), ACC-001 (Elan/Wyeth), and Affitope;

(vii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate, celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko biloba extract EGb-761 (ROKAN®, TEBONIN®), tramiprosate (CEREBRIL®, ALZHEMED®), KIACTA®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285, 293, including PTI-777;

(ix) alpha-adrenergic receptor agonists, and beta-adrenergic receptor blocking agents (beta blockers); anticholinergics; anticonvulsants; antipsychotics; calcium channel blockers;

catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lanciemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xiii) phosphodiesterase (PDE) inhibitors, including (a) PDE1 inhibitors (b) PDE2 inhibitors (c) PDE3 inhibitors (d) PDE4 inhibitors (e) PDE5 inhibitors (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl) quinoline (PF-2545920);

(xiv) serotonin (5-hydroxytryptamine) 1A (5-HT$_{1A}$) receptor antagonists, such as spiperone, levo-pindolol, lecozotan;

(XV) serotonin (5-hydroxytryptamine) 2C (5-HT$_{2C}$) receptor agonists, such as vabicaserin, and zicronapine; serotonin (5-hydroxytryptamine) 4 (5-HT$_4$) receptor agonists/antagonists, such as PRX-03140 (Epix) and PF-04995274;

(xvi) serotonin (5-hydroxytryptamine) 3C (5-HT$_{3C}$) receptor antagonists, such as Ondansetron (Zofran);

(xvii) serotonin (5-hydroxytryptamine) 6 (5-HT$_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xviii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xix) Glycine transporter-1 inhibitors such as paliflutine, ORG-25935, and ORG-26041; and mGluR modulators such as AFQ-059 and amantidine;

(xx) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xxi) P450 inhibitors, such as ritonavir;

(xxii) tau therapy targets, such as davunetide; and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of the present invention may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of the invention, or tautomers thereof or pharmaceutically acceptable salts of said compounds or tautomers, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in many cases, the compounds in Schemes 1 through 10 will be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1 refers to the preparation of compounds of formula I. Referring to Scheme 1, the compound of formula I can be prepared from the compound of formula II through a removal of protecting group $P^1$. $P^1$ in this case refers to groups well known to those skilled in the art for amine protection. For example, $P^1$ may be a benzoyl group (Bz), which can be cleaved via acidic conditions, or through treatment with 1,8-diazabicyclo[5.4.0]undec-7-ene (DBU) in methanol. Alternatively $P^1$ may be one of many protecting group suitable for amines, including 9-fluorenylmethoxycarbonyl (Fmoc) or tert-butoxycarbonyl (BOC) and can be cleaved under standard conditions known to one skilled in the art.

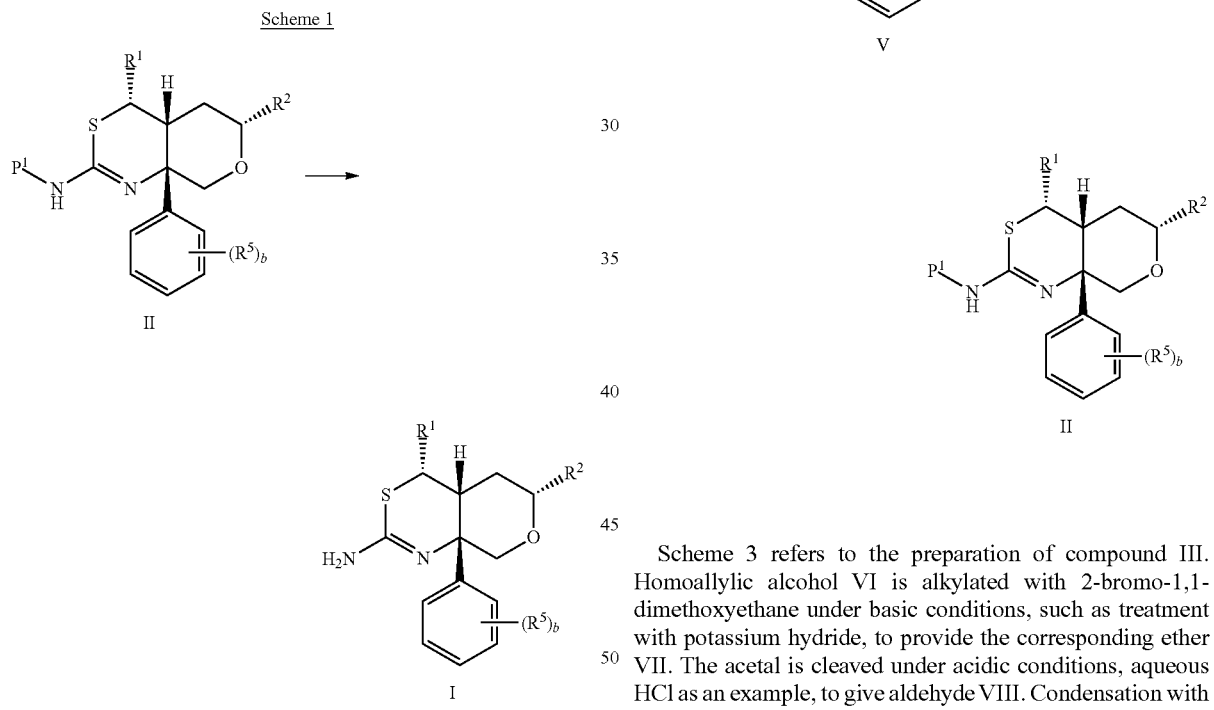

Scheme 2 refers to the preparation of compounds II wherein $P^1$ is Bz or Boc. Isoxazolidines of formula III are subjected to reducing conditions, for instance zinc in acetic acid, affording compounds of formula IV. The resulting amino alcohols are treated with an isothiocyanate, for instance benzoyl isothiocyanate, to provide thioureas of formula V. Cyclization is induced using strong acid, including for instance sulfuric acid, or alternatively, standard Mitsunobu conditions, to give compounds of formula II. Compound II can be converted into a compound of formula I according to the methods of Scheme 1.

Scheme 3 refers to the preparation of compound III. Homoallylic alcohol VI is alkylated with 2-bromo-1,1-dimethoxyethane under basic conditions, such as treatment with potassium hydride, to provide the corresponding ether VII. The acetal is cleaved under acidic conditions, aqueous HCl as an example, to give aldehyde VIII. Condensation with a hydroxylamine salt, such as hydroxylamine sulfate, provides a geometric mixture of the corresponding oxime IX. Cycloaddition to form isoxazoline X may be carried out by treatment of oxime IX with an oxidizing agent, such as sodium hypochlorite or N-chlorosuccinimide. Reaction of isoxazoline X with an appropriate arylmetallic reagent (for instance, an aryllithium such as 2,4-difluorophenyllithium, or the corresponding aryl Grignard reagent) at low temperature, e.g., −78° C., yields compounds of formula III. One of ordinary skill in the art will recognize that the stereochemistry of addition of the arylmetallic reagent is determined by the stereochemistry of the adjacent methine center, yielding a racemic mixture of cis-fused diastereomers, which can be converted into compounds of formula I according to the methods of Schemes 2 and 1.

Scheme 3

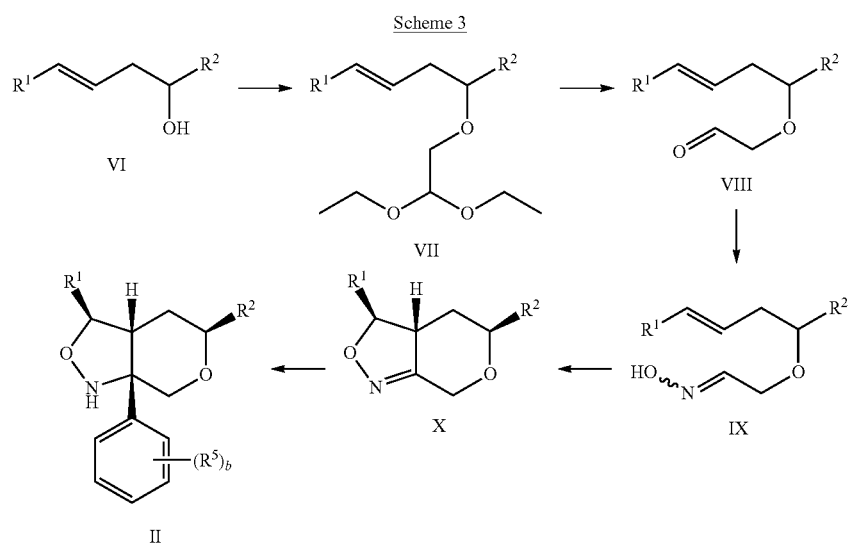

Scheme 4 refers to the preparation of compounds II wherein $P^1$ is Bz and $R^2$ is an oxetane. Treatment of compounds of formula XI with appropriate ylide-generating conditions, for instance the combination of trimethylsulfoxonium iodide and sodium hydride, provides epoxides of formula XII. A second iteration of appropriate ylide-generating conditions, for instance the combination of trimethylsulfoxonium iodide and sodium hydride, provides compounds of formula II, wherein $R^2$ is an oxetane. Compound II can be converted into a compound of formula I according to the methods of Scheme 1.

Scheme 4

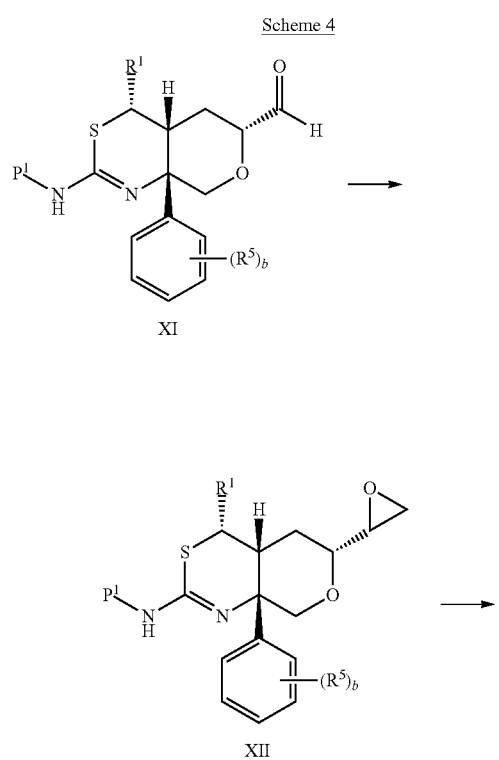

-continued

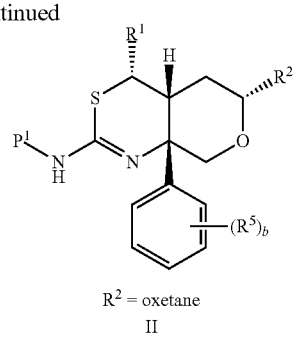

$R^2$ = oxetane
II

Scheme 5 refers to the preparation of compounds II wherein $P^1$ is Bz and $R^2$ is a tetrahydrofuran. Treatment of compounds of formula XI with an appropriate alkylmagnesium reagent, for instance 3-{[tert-butyl(dimethyl)silyl]oxy}propyl)magnesium bromide, provides secondary alcohols of formula XIII, wherein $P^2$ is tert-butyldimethylsilyl (TBS). Deprotection of $P^2$ using standard desilylative conditions, for instance tetrabutylammonium fluoride (TBAF) in THF, provides diols of formula XIV. Diol XIV can be closed to compounds of formula II via activation of the primary alcohol, for instance via the use of trifluoromethanesulfonic anhydride and 2,6-dimethylpyridine in dichloromethane at −78° C., and allowing the reaction to warm to 0° C. over 30 minutes. Compound II can be converted into a compound of formula I according to the methods of Scheme 1.

Scheme 5

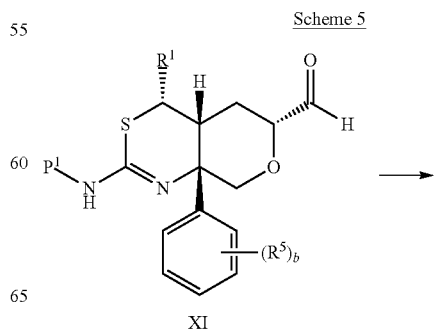

-continued

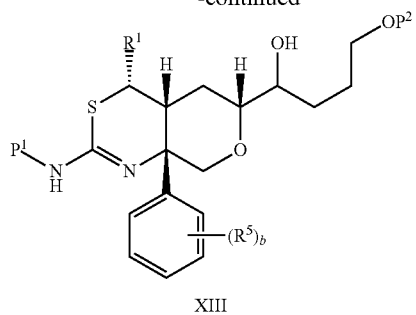

XIII

-continued

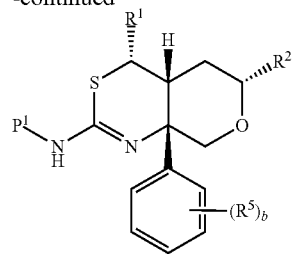

$R^2$ = tetrahydrofuran
II

Scheme 6 refers to the preparation of compounds XI wherein $P^1$ is Bz. Isoxazolidines of formula XV (which may be obtained via the chemistry depicted in Scheme 3, utilizing a benzyloxymethyl group in place of $R^2$) are subjected to reducing conditions, for instance zinc in acetic acid, affording compounds of formula XVI. The amino alcohols XVI are treated with an isothiocyanate, for instance benzoyl isothiocyanate, to provide thioureas of formula XVII. Cyclization is induced using strong acid, including for instance sulfuric acid, or alternatively, standard Mitsunobu conditions, to give compounds of formula XVIII. Cleavage of the benzyl ether under standard conditions, for instance using boron trichloride, provides alcohols of formula XIX. The oxidation of compounds of formula XIX can be effected by a number of standard oxidation protocols, for instance using Dess-Martin periodinane or sulfur trioxide-pyridine with DMSO (Parikh-Doering conditions). Compound XI can be converted into a compound of formula II according to the methods of Schemes 4 or 5.

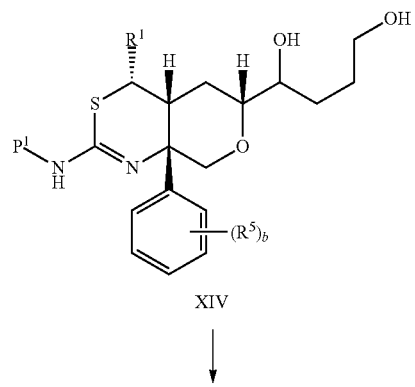

XIV

Scheme 6

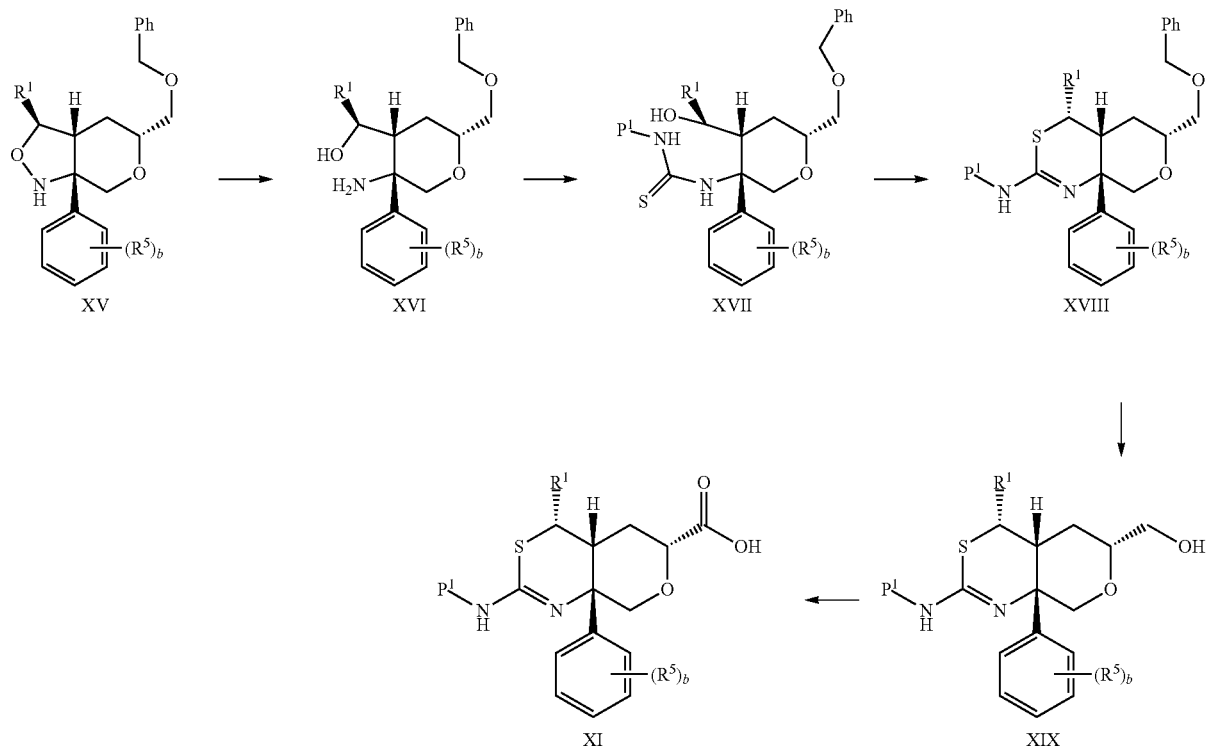

Scheme 7 refers to the preparation of compounds III wherein $R^1$ is —$CH_2F$ or —$CH_2OCH_3$. Isoxazolidines of formula XX are subjected to suitable conditions to introduce the respective group, for instance sodium hydride followed by methyl iodide, affording compounds of formula XXI. Reaction of isoxazoline XXI with an appropriate arylmetallic reagent (for instance, an aryllithium such as 2,4-difluorophenyllithium, or the corresponding aryl Grignard reagent) at low temperature, e.g., −78° C., yields compounds of formula III, which can be converted into compounds of formula I according to the methods of Schemes 2 and 1.

Scheme 7

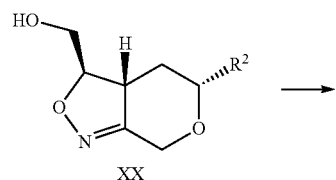

XX

Scheme 8 refers to the preparation of compounds XX. Compounds of formula XXII (formed in analogous fashion to Scheme 3) are subjected to standard ruthenium-catalyzed cross-metathesis conditions, for instance using Grubbs' second generation metathesis catalyst, in the presence of methyl prop-2-enoate, to afford compounds of formula XXIII. The acetal is cleaved under acidic conditions, aqueous HCl as an example, to give an aldehyde that is immediately condensed with a hydroxylamine salt, such as hydroxylamine sulfate, providing a geometric mixture of the corresponding oxime XXIV. Cycloaddition to form isoxazoline XXV may be carried out by treatment of oxime XXIV with an oxidizing agent, such as sodium hypochlorite or N-chlorosuccinimide. Reduction of the methyl ester of isoxazoline XXV can be effected through the use of an appropriate reducing agent, for instance sodium borohydride, to afford a compound of formula XX, which can be converted into compounds of formula I according to the methods of Schemes 7, 2, and 1.

Scheme 8

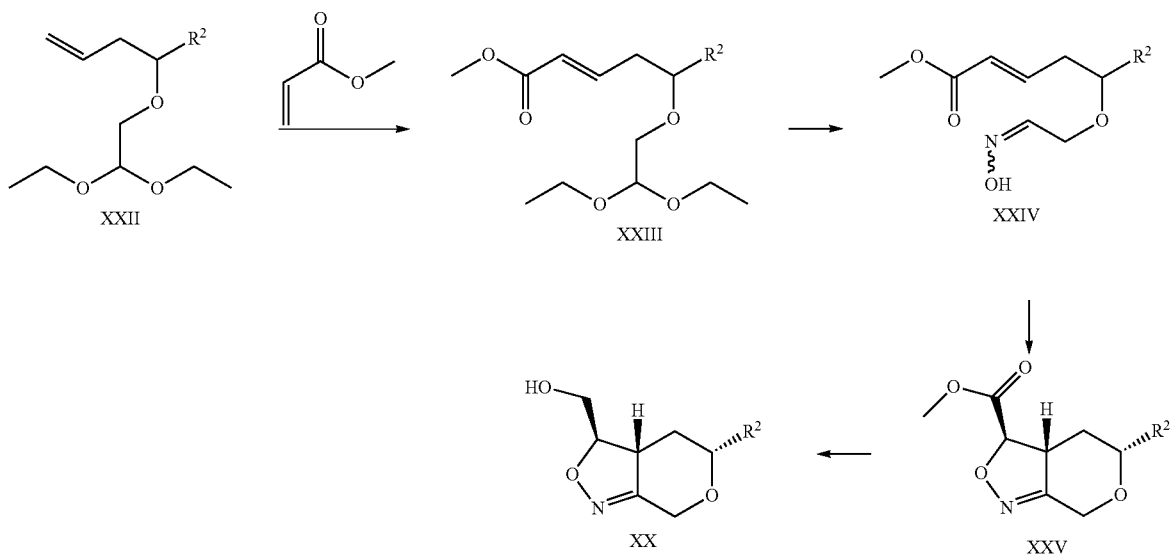

-continued

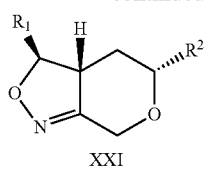

XXI

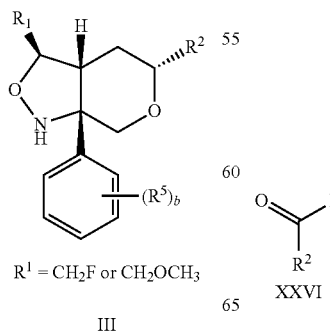

$R^1$ = $CH_2F$ or $CH_2OCH_3$

III

Scheme 9 refers to the preparation of homochiral compounds VIa wherein $R^1$ is methyl. Compounds of formula XXVI are subjected to a crotylation using a camphor-derived allylic alcohol (see J. Nokami et al., J. Am. Chem. Soc. 2001, 123, 9168-9169), resulting in stereochemically defined compounds of formula VIa, which can be converted to compounds of formula I via Schemes 3, 2, and 1.

Scheme 9

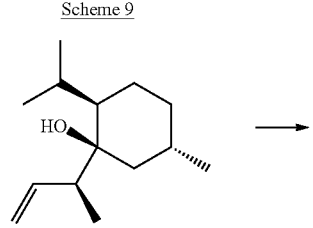

XXVI

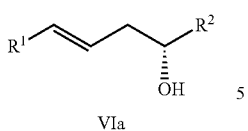

VIa

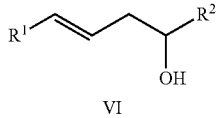

VI

Scheme 10 refers to the preparation of compounds VI wherein $R^2$ is alkyl. Acids of formula XXVII are converted to the corresponding Weinreb amide XXVIII and alkylated with an allylmetallic reagent (for instance allyl magnesium bromide). Reduction of the ketone can be effected through use of an appropriate reducing agent, for instance lithium aluminium hydride, to afford a compound of formula VI, which can be converted to compounds of formula I via Schemes 3, 2, and 1.

Scheme 10

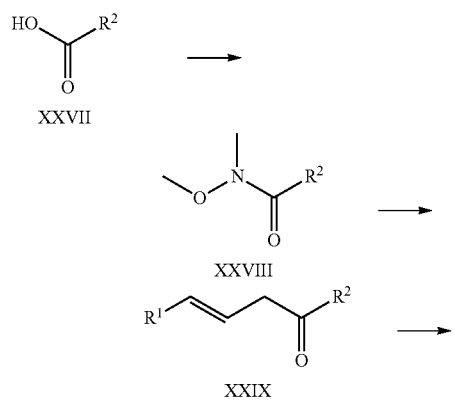

Experimental Procedures and Working Examples

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.).

Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

Preparation P1
N-[(4aR,6R,8aS)-8a-(2,4-Difluorophenyl)-6-formyl-4,4a,5,6,8,8a-hexahydropyrano[3,4-d][1,3]thiazin-2-yl]benzamide (P1)

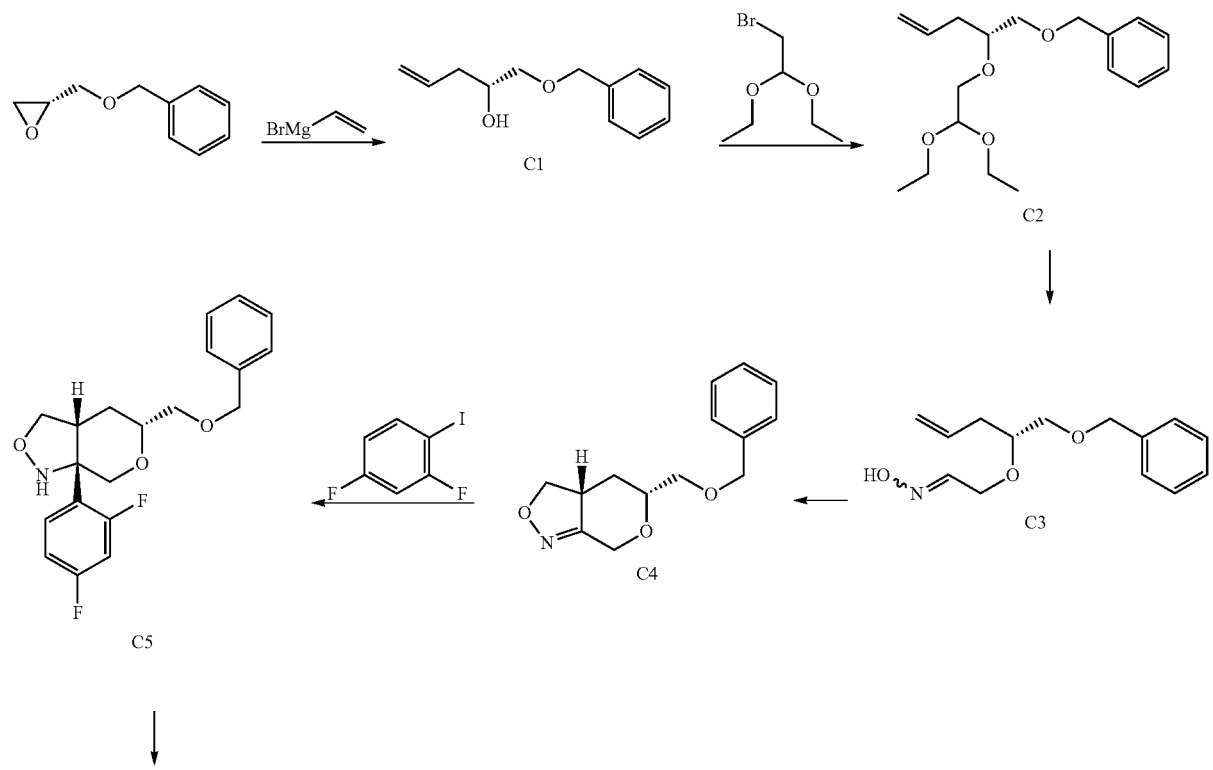

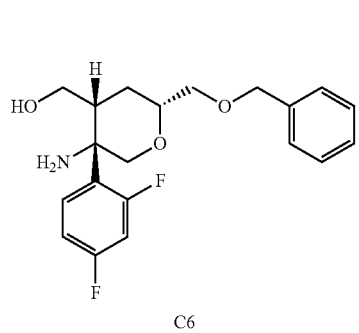
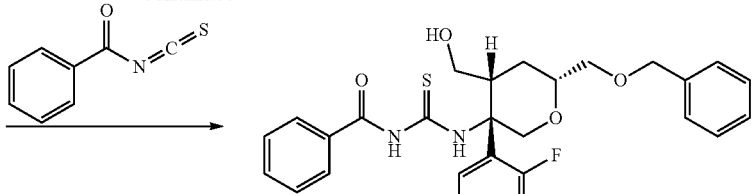
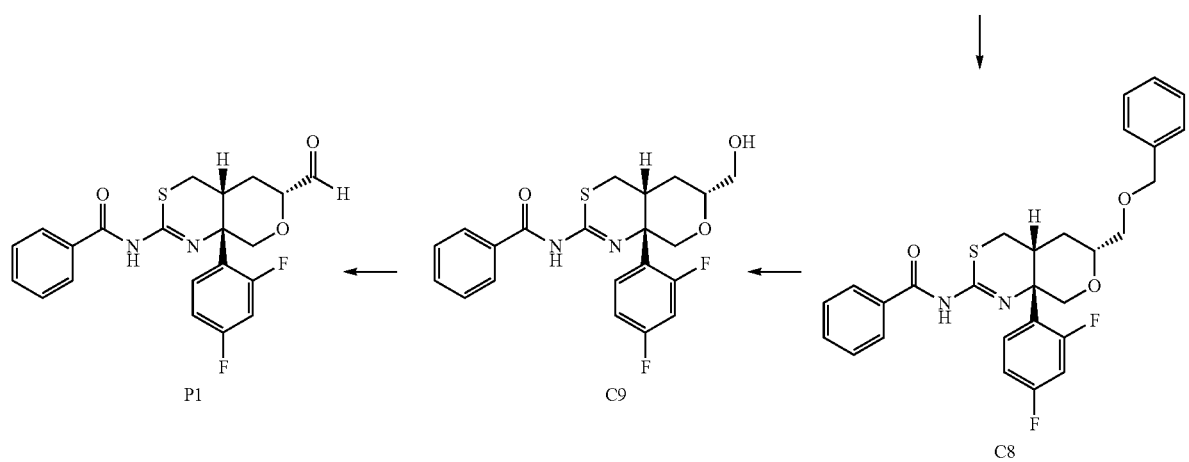

Step 1. Synthesis of (2R)-1-(benzyloxy)pent-4-en-2-ol (C1)

To a solution of (2R)-2-[(benzyloxy)methyl]oxirane (167 g, 1.02 mol) in tetrahydrofuran (2 L) was added copper(I) iodide (11.62 g, 61.02 mmol) at room temperature. The mixture was stirred for 5 minutes, then cooled to −78° C. A solution of vinylmagnesium bromide (1 M in tetrahydrofuran, 1.12 L, 1.12 mol) was added drop-wise over 1 hour while the reaction temperature was maintained below −70° C. Upon completion of the addition, the cooling bath was removed and the reaction mixture was left to stir at room temperature for 1 hour, then quenched by slow addition of aqueous ammonium chloride solution (200 mL). After dilution with additional aqueous ammonium chloride solution (1.5 L) and ethyl acetate (1.5 L), the aqueous layer was extracted with ethyl acetate (1 L) and the combined organic layers were washed with aqueous ammonium chloride solution (1.5 L), dried over magnesium sulfate, filtered, and concentrated in vacuo. Three batches of this reaction were carried out and combined to give the product as an orange oil. Yield: 600 g, 3.1 mmol, quantitative. $^1$H NMR (400 MHz, CDCl$_3$) δ 7.28-7.40 (m, 5H), 5.78-5.90 (m, 1H), 5.08-5.17 (m, 2H), 4.57 (s, 2H), 3.86-3.94 (m, 1H), 3.53 (dd, J=9.6, 3.3 Hz, 1H), 3.39 (dd, J=9.6, 7.4 Hz, 1H), 2.26-2.34 (m, 3H).

Step 2. Synthesis of ({[(2R)-2-(2,2-diethoxyethoxy)pent-4-en-1-yl]oxy}methyl)benzene (C2)

To a suspension of sodium hydride (60% in mineral oil, 98.8 g, 2.47 mol) in tetrahydrofuran (1 L) at room temperature was added drop-wise over 30 minutes a solution of (2R)-1-(benzyloxy)pent-4-en-2-ol (C1) (190 g, 0.988 mol) in tetrahydrofuran (500 mL), while the reaction temperature was maintained below 30° C. After 30 minutes, a solution of 2-bromo-1,1-diethoxyethane (390 g, 1.98 mol) in tetrahydrofuran (500 mL) was added drop-wise. The reaction mixture was stirred at room temperature for 1 hour, then the temperature was gradually increased to 70° C. and the reaction mixture was left to stir at 70° C. for 18 hours. It was then cooled to room temperature, subsequently cooled in an ice bath, and quenched by slow addition of ice/water (200 mL), while keeping the internal reaction temperature at approximately 18° C. The mixture was partitioned between saturated aqueous sodium chloride solution (1 L) and ethyl acetate (1 L), and the organic layer was washed with saturated aqueous sodium chloride solution (1 L), dried over magnesium sulfate, filtered, and concentrated under reduced pressure. Purification was effected by filtration through a pad of silica (Gradient: 0% to 20% ethyl acetate in heptane) to afford the product as an orange oil. Yield: 257 g of 60% purity, approximately 500 mmol, 51% yield and 57.76 g of 90% purity, approximately 170 mmol, 17% yield. $^1$H NMR (400 MHz, CDCl$_3$), product peaks only: δ 7.26-7.38 (m, 5H), 5.78-5.90 (m, 1H), 5.02-5.13 (m, 2H), 4.61 (t, J=5.3 Hz, 1H), 4.55 (s, 2H), 3.48-3.74 (m, 9H), 2.31-2.37 (m, 2H), 1.22 (t, J=7.1 Hz, 3H), 1.21 (t, J=7.1 Hz, 3H).

Step 3. Synthesis of 2-{[(2R)-1-(benzyloxy)pent-4-en-2-yl]oxy}-N-hydroxyethanimine (C3)

A solution of ({[(2R)-2-(2,2-diethoxyethoxy)pent-4-en-1-yl]oxy}methyl)benzene (C2) (234 g, 0.759 mol) in formic acid (400 mL) and water (100 mL) was stirred at room temperature for 2 hours. As LCMS analysis revealed a small amount of remaining starting material, formic acid (50 mL) was added and the reaction mixture was stirred for a further 30 minutes. The reaction mixture was diluted with ethanol (1

L) and water (400 mL). Hydroxylamine sulfate (435 g, 2.65 mol) and sodium acetate (217 g, 2.64 mol) were added and the reaction was stirred at room temperature for 18 hours. The reaction mixture was then filtered and concentrated in vacuo; the residue was partitioned between ethyl acetate (500 mL) and water (1 L), and the aqueous layer was extracted with ethyl acetate (3×500 mL). The combined organic layers were washed with saturated aqueous sodium chloride solution (2×500 mL), dried over magnesium sulfate, filtered, and concentrated under reduced pressure to provide the product as an orange oil (234 g), which was taken directly to the following step. By $^1$H NMR, this material consisted of a roughly 1:1 mixture of oxime isomers. LCMS m/z 250.1 [M+H$^+$]. $^1$H NMR (400 MHz, CDCl$_3$), characteristic peaks: δ [7.52 (t, J=5.5 Hz) and 6.96 (t, J=3.6 Hz), total 1H], 7.28-7.39 (m, 5H), 5.74-5.87 (m, 1H), 5.04-5.14 (m, 2H), 4.55 and 4.56 (2 s, total 2H), {4.45-4.55 (m) and [4.27 (dd, half of ABX pattern, J=13.2, 5.4 Hz) and 4.21 (dd, half of ABX pattern, J=13.2, 5.6 Hz)], total 2H}, 2.30-2.37 (m, 2H).

Step 4. Synthesis of (3aR,5R)-5-[(benzyloxy)methyl]-3,3a,4,5-tetrahydro-7H-pyrano[3,4-c][1,2]oxazole (C4)

An aqueous solution of sodium hypochlorite (14.5% solution, 600 mL) was added drop-wise to a 0° C. solution of 2-{[(2R)-1-(benzyloxy)pent-4-en-2-yl]oxy}-N-hydroxyethanimine (C3) (224 g from the previous step, ≤0.759 mol) in dichloromethane (1 L), while the internal temperature was maintained below 15° C. After completion of the addition, the reaction mixture was left to stir at 0° C. for 1.5 hours, then diluted with water (1 L) and dichloromethane (500 mL). The aqueous layer was extracted with dichloromethane (2×500 mL), and the combined organic layers were washed with saturated aqueous sodium chloride solution (500 mL), water (500 mL) and again with saturated aqueous sodium chloride solution (500 mL). They were subsequently dried over magnesium sulfate, filtered, and concentrated in vacuo. Purification via silica gel chromatography (Gradient: 0% to 25% ethyl acetate in heptane) afforded the product as a colorless oil. The indicated relative stereochemistry of compound C4 was assigned based on nuclear Overhauser enhancement studies, which revealed an interaction between the methine protons on carbons 3a and 5. Yield: 85.3 g, 345 mmol, 45% over 2 steps. LCMS m/z 248.1 [M+H$^+$]. $^1$H NMR (400 MHz, CDCl$_3$) δ 7.27-7.40 (m, 5H), 4.77 (d, J=13.5 Hz, 1H), 4.54-4.65 (m, 3H), 4.22 (dd, J=13.5, 1 Hz, 1H), 3.79 (dd, J=11.7, 8.0 Hz, 1H), 3.69-3.76 (m, 1H), 3.57 (dd, half of ABX pattern, J=10.1, 5.9 Hz, 1H), 3.49 (dd, half of ABX pattern, J=10.1, 4.3 Hz, 1H), 3.39-3.5 (m, 1H), 2.20 (ddd, J=12.9, 6.5, 1.6 Hz, 1H), 1.51-1.62 (m, 1H).

Step 5. Synthesis of (3aR,5R,7aS)-5-[(benzyloxy)methyl]-7a-(2,4-difluorophenyl)hexahydro-1H-pyrano[3,4-c][1,2]oxazole (C5)

Boron trifluoride diethyl etherate (60.1 mL, 474 mmol) was added to a solution of (3aR,5R)-5-[(benzyloxy)methyl]-3,3a,4,5-tetrahydro-7H-pyrano[3,4-c][1,2]oxazole (C4) (50.0 g, 202 mmol) in a 1:1 mixture of toluene and diisopropyl ether (2 L) at an internal temperature of −76° C. The reaction was stirred at this temperature for 30 minutes, then treated with 2,4-difluoro-1-iodobenzene (27.1 mL, 226 mmol). While the reaction temperature was maintained at −76 to −71° C., n-butyllithium (2.5 M in hexanes, 85.7 mL, 214 mmol) was slowly added. The reaction mixture was stirred at −76° C. for 1.5 hours, then was quenched with saturated aqueous ammonium chloride solution (1 L) and partitioned between water (1 L) and ethyl acetate (750 mL). After the heterogeneous mixture warmed to room temperature, the aqueous layer was extracted with ethyl acetate (3×250 mL), and the combined organic layers were washed with saturated aqueous sodium chloride solution (550 mL), dried over sodium sulfate, filtered, and concentrated in vacuo. Chromatography on silica gel (Gradient: 0% to 70% ethyl acetate in heptane) afforded the product as a yellow oil. The cis ring fusion was assigned to this and subsequent products from similar reactions on the basis of the expected attack of the organometallic reagent on the convex side of the bicyclic ring system. Yield: 48.14 g, 133.2 mmol, 66%. $^1$H NMR (400 MHz, CDCl$_3$) δ 7.94 (ddd, J=9, 9, 7 Hz, 1H), 7.28-7.40 (m, 5H), 6.87-6.93 (m, 1H), 6.80 (ddd, J=12.0, 8.6, 2.4 Hz, 1H), 4.60 (AB quartet, J$_{AB}$=12.1 Hz, Δν$_{AB}$=21.4 Hz, 2H), 4.14 (br dd, J=12.8, 1.3 Hz, 1H), 3.82-3.90 (m, 2H), 3.72 (d, J=7.2 Hz, 1H), 3.54-3.60 (m, 2H), 3.50 (dd, half of ABX pattern, J=10.3, 4.1 Hz, 1H), 3.04-3.13 (m, 1H), 1.86 (ddd, J=14.0, 7.0, 2.0 Hz, 1H), 1.49-1.61 (m, 1H).

Step 6. Synthesis of [(2R,4R,5S)-5-amino-2-[(benzyloxy)methyl]-5-(2,4-difluorophenyl)tetrahydro-2H-pyran-4-yl]methanol (C6)

(3aR,5R,7aS)-5-[(Benzyloxy)methyl]-7a-(2,4-difluorophenyl)hexahydro-1H-pyrano[3,4-c][1,2]oxazole (C5) (48.1 g, 133 mmol) was dissolved in acetic acid (444 mL) and treated with zinc powder (113 g, 1.73 mol). The reaction mixture, which had warmed to 40° C., was allowed to cool to room temperature and stir for 16 hours. Insoluble material was removed via filtration through a Celite pad, and the pad was washed with ethyl acetate (3×500 mL). The combined filtrates were neutralized with saturated aqueous sodium bicarbonate solution (2.5 L), and the aqueous layer was extracted with ethyl acetate (3×500 mL). The combined organic layers were washed with saturated aqueous sodium chloride solution (1 L), dried over sodium sulfate, filtered, and concentrated under reduced pressure to provide the product as a thick yellow oil, which was used in the following reaction without additional purification. Yield: 48.7 g, assumed quantitative. $^1$H NMR (400 MHz, CDCl$_3$), characteristic peaks: δ 7.62-7.80 (br m, 1H), 7.28-7.39 (m, 5H), 6.94-7.06 (m, 1H), 6.83 (ddd, J=12.7, 8.5, 2.6 Hz, 1H), 4.61 (AB quartet, upfield doublet is broadened, J$_{AB}$=12.2 Hz, Δν$_{AB}$=30.5 Hz, 2H), 4.22 (dd, J=11.6, 2.2 Hz, 1H), 3.83-3.92 (br m, 1H), 3.62-3.73 (br m, 1H), 3.56 (dd, J=10.2, 3.5 Hz, 1H), 3.34-3.41 (m, 1H), 2.26-2.43 (br m, 1H), 2.00-2.17 (br m, 1H), 1.65 (ddd, J=14.1, 4.5, 2.5 Hz, 1H).

Step 7. Synthesis of N-{[(3S,4R,6R)-6-[(benzyloxy)methyl]-3-(2,4-difluorophenyl)-4-(hydroxymethyl)tetrahydro-2H-pyran-3-yl]carbamothioyl}benzamide (C7)

Benzoyl isothiocyanate (17.8 mL, 132 mmol) was added to a solution of [(2R,4R,5S)-5-amino-2-[(benzyloxy)methyl]-5-(2,4-difluorophenyl)tetrahydro-2H-pyran-4-yl]methanol (C6) (48.7 g, 133 mmol) in dichloromethane (1.34 L), and the reaction mixture was allowed to stir at room temperature for 18 hours. Removal of solvent in vacuo afforded the product as a white solid, which was used without additional purification. Yield: 72.2 g, assumed quantitative. LCMS m/z 527.2 [M+H$^+$]. $^1$H NMR (400 MHz, CD$_3$OD), characteristic peaks: δ 7.89-7.93 (m, 2H), 7.62-7.67 (m, 1H), 7.50-7.56 (m, 2H), 7.42-7.54 (br m, 1H), 7.31-7.36 (m, 2H), 7.17-7.28 (m, 3H), 6.86-6.98 (m, 2H), 4.57 (AB quartet, J$_{AB}$=11.9 Hz, Δv$_{AB}$=11.8 Hz, 2H), 3.84-3.91 (m, 1H), 3.64 (br dd, half of ABX pattern, J=10.6, 6.0 Hz, 1H), 3.58 (dd, half of ABX pattern, J=10.6, 3.8 Hz, 1H), 3.44-3.54 (br m, 1H), 2.32-2.59 (br m, 1H), 1.82-2.06 (m, 2H).

Step 8. Synthesis of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8)

Pyridine (11.0 mL, 137 mmol) was added to a solution of N-{[(3S,4R,6R)-6-[(benzyloxy)methyl]-3-(2,4-difluorophenyl)-4-(hydroxymethyl)tetrahydro-2H-pyran-3-yl]carbamothioyl}benzamide (C7) (19.00 g, 36.08 mmol) in dichloromethane (150 mL), and the resulting solution was cooled to −50 to −60° C. Trifluoromethanesulfonic anhydride (12.1 mL, 71.9 mmol) in dichloromethane (50 mL) was added drop-wise, and the reaction mixture was gradually warmed to −5° C. over 3 hours. Water was added, and the aqueous layer was extracted with dichloromethane. The combined organic layers were washed with saturated aqueous sodium chloride solution, dried over magnesium sulfate, filtered, and concentrated in vacuo. Purification via silica gel chromatography (Gradient: 20% to 40% ethyl acetate in heptane) provided the product as a yellow foamy solid. Yield: 15.51 g, 30.50 mmol, 85%. LCMS m/z 509.2 [M+H$^+$]. $^1$H NMR (400 MHz, CDCl$_3$) δ 8.23 (br d, J=7 Hz, 2H), 7.37-7.57 (br m, 4H), 7.24-7.36 (m, 5H), 6.85-6.97 (m, 2H), 4.58 (AB quartet, upfield signals are slightly broadened, J$_{AB}$=11.9 Hz, Δv$_{AB}$=23.5 Hz, 2H), 4.17 (br d, J=12 Hz, 1H), 3.90-3.97 (m, 1H), 3.83 (br d, J=12 Hz, 1H), 3.64 (dd, half of ABX pattern, J=10.1, 6.4 Hz, 1H), 3.50 (dd, half of ABX pattern, J=10.2, 4.4 Hz, 1H), 3.11-3.21 (br m, 1H), 3.02 (dd, J=12.9, 4.1 Hz, 1H), 2.64 (br d, J=13 Hz, 1H), 1.92-2.05 (br m, 1H), 1.71 (br d, J=13 Hz, 1H).

Step 9. Synthesis of N-[(4aR,6R,8aS)-8a-(2,4-difluorophenyl)-6-(hydroxymethyl)-4,4a,5,6,8,8a-hexahydropyrano[3,4-d][1,3]thiazin-2-yl]benzamide (C9)

Boron trichloride (1 M solution in heptane, 89.7 mL, 89.7 mmol) was added to a 0° C. solution of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8) (15.20 g, 29.89 mmol) in dichloromethane (150 mL). After 15 minutes, the reaction mixture was allowed to warm to room temperature and stirred for 4 hours. Methanol (50 mL) was then added, first drop-wise {Caution: violent reaction} and then at a steady rate, while the interior of the flask was flushed with nitrogen gas. The mixture was heated at reflux for 30 minutes, cooled to room temperature and concentrated in vacuo. The residue was again dissolved in methanol, stirred, and concentrated in vacuo. The resulting material was taken up in dichloromethane and washed sequentially with 1 M aqueous sodium hydroxide solution, water, and saturated aqueous sodium chloride solution. The organic layer was dried over magnesium sulfate, filtered, and concentrated under reduced pressure. Chromatographic purification on silica gel (Gradient: 0% to 3% methanol in ethyl acetate) provided the product as a foamy yellow solid. Yield: 11.97 g, 28.60 mmol, 96%. LCMS m/z 419.2 [M+H$^+$]. $^1$H NMR (400 MHz, CD$_3$OD) δ 8.13 (d, J=7.4 Hz, 2H), 7.50-7.56 (m, 1H), 7.41-7.49 (m, 3H), 7.02-7.11 (m, 2H), 4.13 (dd, J=11.9, 1.8 Hz, 1H), 3.90 (d, J=12.1 Hz, 1H), 3.72-3.80 (m, 1H), 3.59 (d, J=5.1 Hz, 1H), 3.14-3.24 (br m, 1H), 2.96 (dd, half of ABX pattern, J=13.1, 4.1 Hz, 1H), 2.75 (dd, half of ABX pattern, J=13.1, 2.7 Hz, 1H), 1.80-1.92 (m, 1H), 1.70 (ddd, J=13.4, 4.2, 2.4 Hz, 1H).

Step 10. Synthesis of N-[(4aR,6R,8aS)-8a-(2,4-difluorophenyl)-6-formyl-4,4a,5,6,8,8a-hexahydropyrano[3,4-d][1,3]thiazin-2-yl]benzamide (P1)

Triethylamine (16.7 mL, 120 mmol) was added in one portion to a solution of N-[(4aR,6R,8aS)-8a-(2,4-difluorophenyl)-6-(hydroxymethyl)-4,4a,5,6,8,8a-hexahydropyrano[3,4-d][1,3]thiazin-2-yl]benzamide (C9) (4.18 g, 10.0 mmol) in dichloromethane (200 mL) that was immersed in a room temperature water bath. After 5 minutes, anhydrous dimethyl sulfoxide (9.94 mL, 140 mmol) was rapidly added, followed immediately by solid sulfur trioxide pyridine complex (98%, 13.0 g, 80.0 mmol) in a single portion. The resulting solution was stirred at ambient temperature for 6.5 hours, then diluted with a 1:1 mixture of water and saturated aqueous sodium chloride solution (200 mL) and stirred for 10 minutes. The aqueous layer was extracted with dichloromethane (2×200 mL), and the combined organic layers were washed with water (100 mL), washed with saturated aqueous sodium chloride solution (100 mL), dried over sodium sulfate, filtered, and concentrated in vacuo. Purification via silica gel chromatography (Gradient: 0% to 100% ethyl acetate in heptane) gave the product as a white solid. Yield: 2.81 g, 6.75 mmol, 67%. LCMS m/z 414.9 [M−H$^+$]. $^1$H NMR (400 MHz, CDCl$_3$) δ 9.71 (s, 1H), 8.20 (br d, J=7 Hz, 2H), 7.50-7.56 (m, 1H), 7.36-7.49 (m, 3H), 6.86-6.99 (m, 2H), 4.23 (br d, J=12.1 Hz, 1H), 4.12 (dd, J=12.1, 2.9 Hz, 1H), 3.94 (d, J=12.5 Hz, 1H), 3.13-3.22 (m, 1H), 3.04 (dd, J=13.1, 4.1 Hz, 1H), 2.69 (dd, J=13.1, 2.9 Hz, 1H), 2.02-2.14 (m, 1H), 1.92-1.99 (m, 1H).

Alternate conversion of ({[(2R)-2-(2,2-diethoxyethoxy)pent-4-en-1-yl]oxy}methyl)benzene (C2) to (3aR,5R)-5-[(benzyloxy)methyl]-3,3a,4,5-tetrahydro-7H-pyrano[3,4-c][1,2]oxazole (C4)

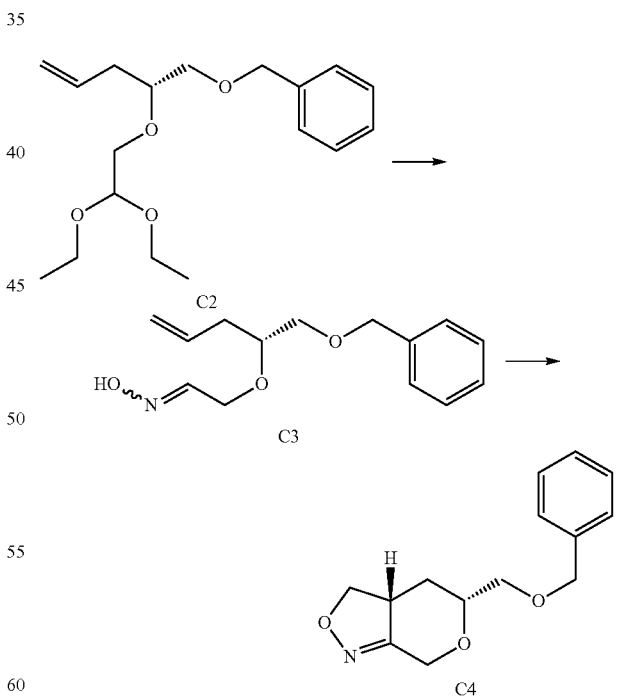

Step 1. Synthesis of 2-{[(2R)-1-(benzyloxy)pent-4-en-2-yl]oxy}-N-hydroxyethanimine (C3)

({[(2R)-2-(2,2-Diethoxyethoxy)pent-4-en-1-yl]oxy}methyl)benzene (C2) (12.4 g, 40.2 mmol) was dissolved in acetic acid (28 mL) and water (12 mL). Hydroxylamine hydrochloride (2.84 g, 40.9 mmol) was added as a solid. After 1 hour, additional hydroxylamine hydrochloride (2.84 g, 40.9 mmol) was added. After 1 more hour, the reaction mixture was diluted with tert-butyl methyl ether (100 mL) and washed with water (3×50 mL), then washed with aqueous potassium carbonate solution (0.5 M, 100 mL). The organic layer was concentrated to provide the product as a pale yellow oil, which consisted of a roughly equimolar mixture of oxime isomers, as assessed by $^1$H NMR. Yield: 9.60 g, 38.5 mmol, 96%. $^1$H NMR (400 MHz, CDCl$_3$) δ 7.98 and 7.67 (2 br s, total 1H), [7.50 (t, J=5.6 Hz) and 6.95 (t, J=3.6 Hz), total 1H], 7.28-7.39 (m, 5H), 5.74-5.87 (m, 1H), 5.04-5.14 (m, 2H), 4.55 and 4.56 (2 s, total 2H), 4.47-4.49 (m, 1H), 4.18-4.28 (m, 1H), 3.47-3.65 (m, 3H), 2.30-2.37 (m, 2H).

Step 2. Synthesis of (3aR,5R)-5-[(benzyloxy)methyl]-3,3a,4,5-tetrahydro-7H-pyrano[3,4-c][1,2]oxazole (C4)

Pyridine (23.1 mL, 286 mmol) was added to a solution of 2-{[(2R)-1-(benzyloxy)pent-4-en-2-yl]oxy}- N-hydroxyethanimine (C3) (35.6 g, 143 mmol) in dichloromethane (350 mL). N-Chlorosuccinimide (19.4 g, 145 mmol) was added in portions over roughly 2 hours. The reaction was stirred for 3 hours, then diluted with an aqueous solution of sodium sulfite (5 g in 100 mL water). The mixture was stirred for 20 minutes, and the aqueous layer was extracted with dichloromethane; the combined organic layers were washed with water, dried, and concentrated. Purification via silica gel chromatography (Eluent: 1:2 ethyl acetate/hexanes) afforded the product. Yield: 21.2 g, 85.7 mmol, 60%. $^1$H NMR (400 MHz, CDCl$_3$) δ 7.28-7.40 (m, 5H), 4.77 (d, J=13.4 Hz, 1H), 4.55-4.65 (m, 3H), 4.22 (dd, J=13.5, 1.3 Hz, 1H), 3.79 (dd, J=11.7, 8.0 Hz, 1H), 3.69-3.76 (m, 1H), 3.57 (dd, half of ABX pattern, J=10.2, 5.9 Hz, 1H), 3.49 (dd, half of ABX pattern, J=10.2, 4.3 Hz, 1H), 3.40-3.5 (m, 1H), 2.21 (ddd, J=12.9, 6.5, 1.8 Hz, 1H), 1.57 (ddd, J=13, 12, 11 Hz, 1H).

Example 1

(4aR,6R,8aS)-8a-(2,4-Difluorophenyl)-6-(tetrahydrofuran-2-yl)-4,4a,5,6,8,8a-hexahydropyrano[3,4-d][1,3]thiazin-2-amine, trifluoroacetate salt (1)

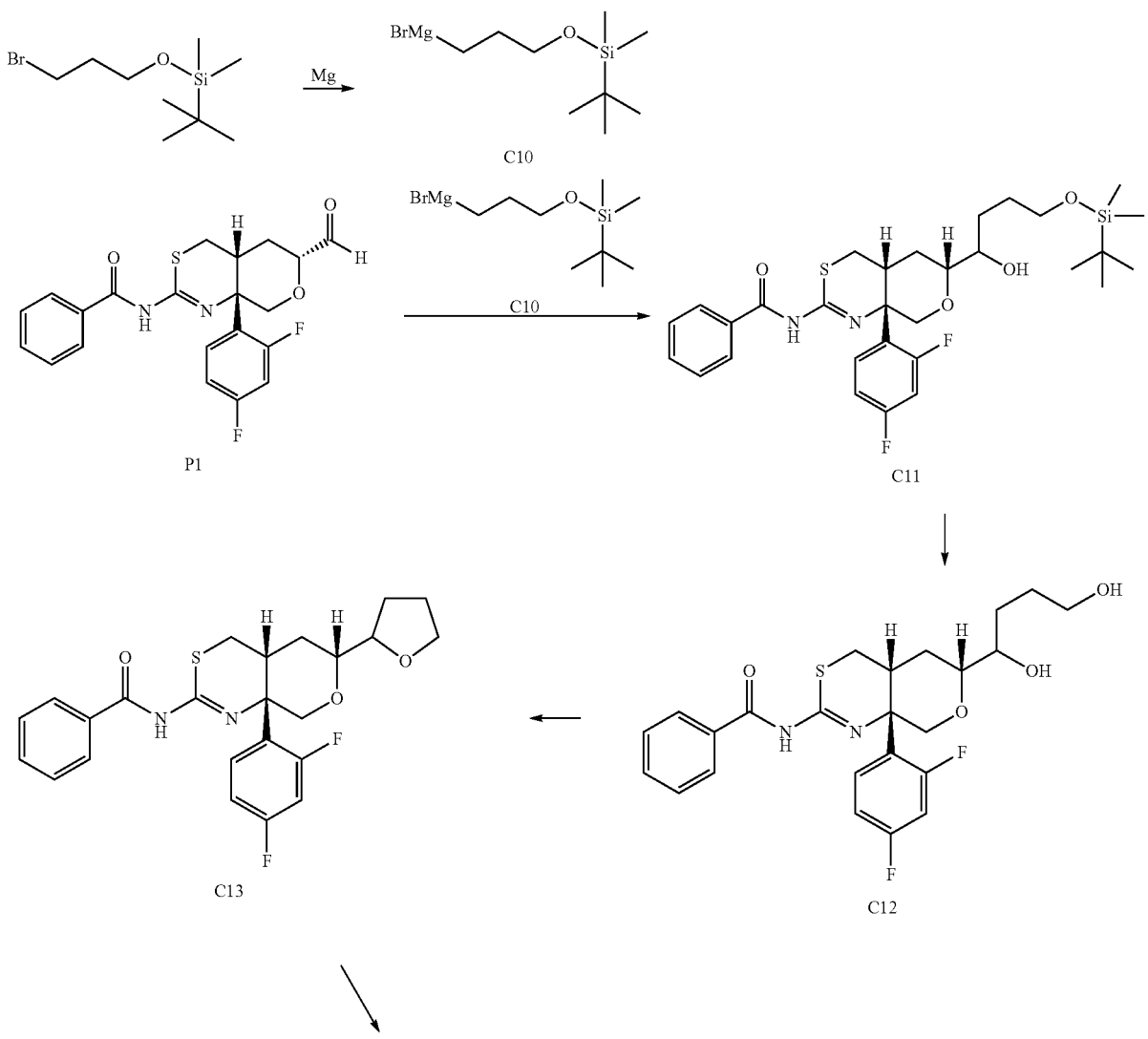

-continued

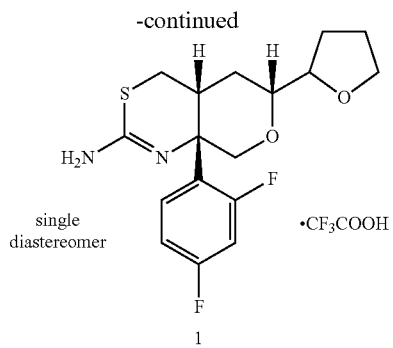

single diastereomer

·CF₃COOH 1
15

Step 1. Synthesis of (3-{[tert-butyl(dimethyl)silyl]oxy}propyl)magnesium bromide (C10)

(3-Bromopropoxy)(tert-butyl)dimethylsilane (97%, 3.52 g, 13.5 mmol) was dissolved in tetrahydrofuran (10 mL); 1 mL of this solution was added to a suspension of magnesium turnings (439 mg, 18.1 mmol) in tetrahydrofuran (13 mL), followed by a few crystals of iodine, and the mixture was stirred for 25 minutes, resulting in an exotherm to an internal temperature of 26° C. The remainder of the substrate solution was added drop-wise, at a rate that maintained the internal reaction temperature below 35° C. The reaction mixture was heated to 40° C. for 1 hour and then cooled to room temperature. The mixture was taken up in a syringe and filtered through a 0.45 µm nylon disc to provide a solution (approximately 26 mL), which was assumed to be 0.5 M in Grignard reagent C10.

Step 2. Synthesis of N-[(4aR,6R,8aS)-6-(4-{[tert-butyl(dimethyl)silyl]oxy}-1-hydroxybutyl)-8a-(2,4-difluorophenyl)-4,4a,5,6,8,8a-hexahydropyrano[3,4-d][1,3]thiazin-2-yl]benzamide (C11)

(3-{[tert-Butyl(dimethyl)silyl]oxy}propyl)magnesium bromide (C10) (0.5 M solution in tetrahydrofuran, 2 mL, 1 mmol) was slowly added to a −78° C. solution of N-[(4aR,6R,8aS)-8a-(2,4-difluorophenyl)-6-formyl-4,4a,5,6,8,8a-hexahydropyrano[3,4-d][1,3]thiazin-2-yl]benzamide (P1) (104 mg, 0.250 mmol) in tetrahydrofuran (3 mL), and the reaction mixture was slowly warmed to 0° C. over 1 hour, then to room temperature over 15 minutes. After an additional 45 minutes at room temperature, saturated aqueous ammonium chloride solution (3 mL) was added, and the mixture was extracted with ethyl acetate (2×10 mL). The combined organic layers were washed with saturated aqueous sodium chloride solution (5 mL), dried over sodium sulfate, filtered, and concentrated in vacuo. Silica gel chromatography (Gradient: 0% to 100% ethyl acetate in heptane) provided the product as an off-white solid. ¹H NMR analysis suggested that this material was a single diastereomer, of unknown configuration at the tetrahydrofuran center. Yield: 28 mg, 47 µmol, 19%. LCMS m/z 591.3 [M+H⁺]. ¹H NMR (400 MHz, CDCl₃), characteristic peaks: δ 8.23 (br d, J=7 Hz, 2H), 7.48-7.55 (m, 1H), 7.36-7.48 (m, 3H), 6.84-6.97 (m, 2H), 4.16 (dd, J=12.2, 1.5 Hz, 1H), 3.84 (d, J=12.1 Hz, 1H), 3.54-3.71 (m, 4H), 3.10-3.18 (m, 1H), 3.02 (dd, J=12.8, 4.0 Hz, 1H), 2.65 (dd, J=12.9, 2.7 Hz, 1H), 1.95-2.08 (m, 1H), 1.43-1.54 (m, 1H), 0.90 (s, 9H), 0.06 (s, 6H).

Step 3. Synthesis of N-[(4aR,6R,8aS)-8a-(2,4-difluorophenyl)-6-(1,4-dihydroxybutyl)-4,4a,5,6,8,8a-hexahydropyrano[3,4-d][1,3]thiazin-2-yl]benzamide (C12)

N-[(4aR,6R,8aS)-6-(4-{[tert-Butyl(dimethyl)silyl]oxy}-1-hydroxybutyl)-8a-(2,4-difluorophenyl)-4,4a,5,6,8,8a-hexahydropyrano[3,4-d][1,3]thiazin-2-yl]benzamide (C11) (28 mg, 47 µmol) was dissolved in tetrahydrofuran (0.3 mL) and cooled to 0° C. A solution of tetrabutylammonium fluoride in tetrahydrofuran (1 M, 61 µL, 61 µmol) was added drop-wise, and the reaction mixture was allowed to warm to room temperature and then stir for 1 hour. After addition of saturated aqueous ammonium chloride solution, the mixture was extracted with ethyl acetate (3×5 mL); the combined organic layers were dried over sodium sulfate, filtered, and concentrated in vacuo. Purification via chromatography on silica gel (Gradient: 35% to 100% ethyl acetate in heptane) provided the product as a white foam. Yield: 19 mg, 40 µmol, 85%. LCMS m/z 477.2 [M+H⁺]. ¹H NMR (400 MHz, CDCl₃) δ 8.22 (br d, J=7.4 Hz, 2H), 7.49-7.56 (m, 1H), 7.42-7.49 (m, 2H), 7.39 (ddd, J=9.0, 9.0, 6.3 Hz, 1H), 6.85-6.97 (m, 2H), 4.16 (dd, J=12.1, 1.4 Hz, 1H), 3.85 (br d, J=12.1 Hz, 1H), 3.53-3.74 (m, 4H), 3.10-3.19 (m, 1H), 3.02 (dd, J=12.9, 4.1 Hz, 1H), 2.65 (dd, J=12.9, 2.5 Hz, 1H), 1.94-2.06 (m, 1H), 1.63-1.80 (m, 4H), 1.49-1.60 (m, 1H).

Step 4. Synthesis of N-[(4aR,6R,8aS)-8a-(2,4-difluorophenyl)-6-(tetrahydrofuran-2-yl)-4,4a,5,6,8,8a-hexahydropyrano[3,4-d][1,3]thiazin-2-yl]benzamide (C13)

Trifluoromethanesulfonic anhydride (12.5 µL, 76 µmol) was added drop-wise to a −78° C. solution of N-[(4aR,6R,8aS)-8a-(2,4-difluorophenyl)-6-(1,4-dihydroxybutyl)-4,4a,5,6,8,8a-hexahydropyrano[3,4-d][1,3]thiazin-2-yl]benzamide (C12) (18 mg, 38 µmol) and 2,6-dimethylpyridine (17.6 µL, 152 µmol) in dichloromethane (0.65 mL), and the reaction mixture was allowed to gradually warm to 0° C. over 30 minutes. The reaction mixture was partitioned between dichloromethane (10 mL) and water (5 mL), and the organic layer was washed with water (2×5 mL) and with saturated aqueous sodium chloride solution (5 mL), then dried over sodium sulfate, filtered and concentrated in vacuo. Silica gel chromatography (Gradient: 0% to 60% ethyl acetate in heptane) afforded the product as an off-white foam. Yield: 14.7 mg, 32.1 µmol, 84%. LCMS m/z 459.2 [M+H⁺]. ¹H NMR (400 MHz, CDCl₃), characteristic peaks: δ 8.23 (br d, J=7.6 Hz, 2H), 7.36-7.55 (m, 4H), 6.84-6.97 (m, 2H), 4.17 (br d, J=12 Hz, 1H), 3.76-3.94 (m, 4H), 3.63-3.70 (m, 1H), 3.11-3.20 (m, 1H), 3.03 (dd, J=12.8, 4.2 Hz, 1H), 2.65 (br d, J=13 Hz, 1H), 1.83-2.06 (m, 4H).

Step 5. Synthesis of (4aR,6R,8aS)-8a-(2,4-difluorophenyl)-6-(tetrahydrofuran-2-yl)-4,4a,5,6,8,8a-hexahydropyrano[3,4-d][1,3]thiazin-2-amine, trifluoroacetate salt (1)

N-[(4aR,6R,8aS)-8a-(2,4-Difluorophenyl)-6-(tetrahydrofuran-2-yl)-4,4a,5,6,8,8a-hexahydropyrano[3,4-d][1,3]thiazin-2-yl]benzamide (C13) (14.5 mg, 31.6 µmol) was combined with methanol (0.3 mL) and 1,8-diazabicyclo[5.4.0]undec-7-ene (4.0 µL, 27 µmol) and heated at 80° C. in a sealed tube for 7 hours. The reaction mixture was cooled to room temperature and concentrated in vacuo, then partitioned between ethyl acetate (5 mL) and water (3 mL). The aqueous layer was extracted with ethyl acetate (5 mL) and the combined organic layers were dried over sodium sulfate, filtered, and concentrated under reduced pressure. Purification via reversed phase HPLC (Column: Waters Sunfire C18, 5 µm; Mobile phase A: 0.05% trifluoroacetic acid in water (v/v); Mobile phase B: 0.05% trifluoroacetic acid in acetonitrile (v/v); Gradient: 5% to 100% B) afforded the product as a solid, presumed to be a single diastereomer of unknown configuration at the tetrahydrofuran center. Yield: 12.1 mg, 25.8 µmol, 82%. LCMS m/z 355.1 [M+H$^+$]. $^1$H NMR (600 MHz, DMSO-d$_6$), characteristic peaks: δ 7.38 (ddd, J=12.7, 9.0, 2.4 Hz, 1H), 7.27-7.33 (m, 1H), 7.21-7.26 (m, 1H), 3.71-3.80 (m, 2H), 3.59-3.67 (m, 2H), 3.13-3.19 (m, 1H), 3.03 (dd, J=13.2, 2.6 Hz, 1H), 2.89 (dd, J=12.9, 3.7 Hz, 1H), 1.86-1.93 (m, 1H), 1.75-1.86 (m, 2H), 1.58-1.70 (m, 3H).

Example 2

(4aR,6R,8aS)-6-Cyclopropyl-8a-(2,4-difluorophenyl)-4,4a,5,6,8,8a-hexahydropyrano[3,4-d][1,3]thiazin-2-amine (2)

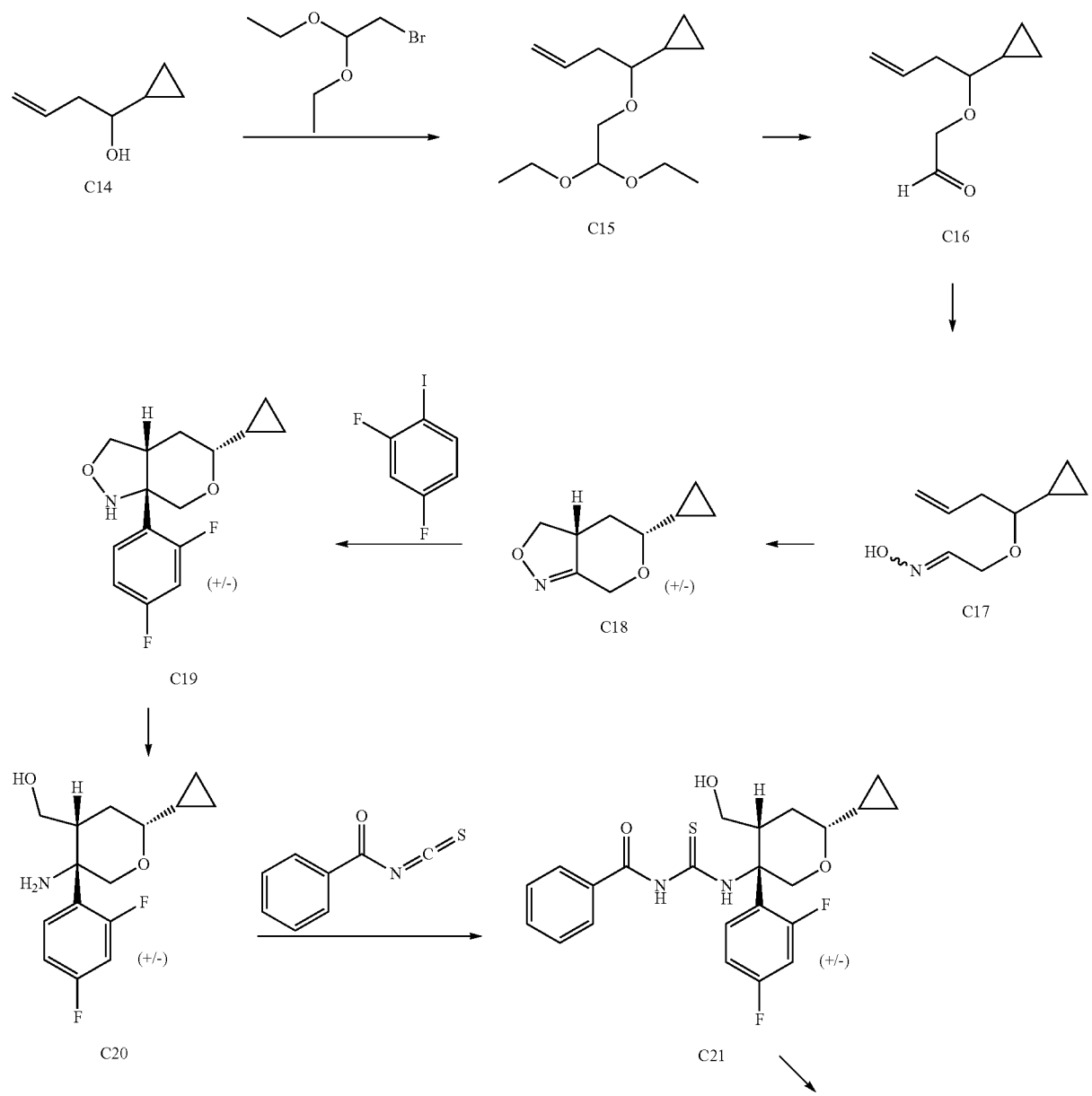

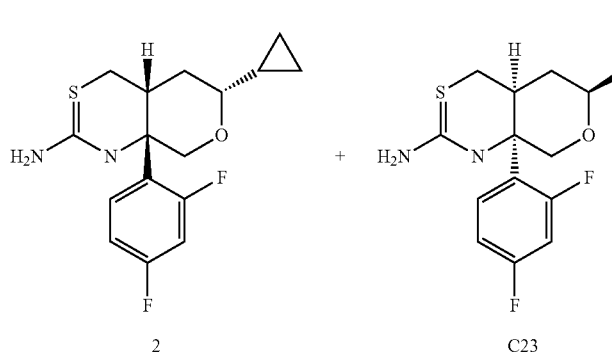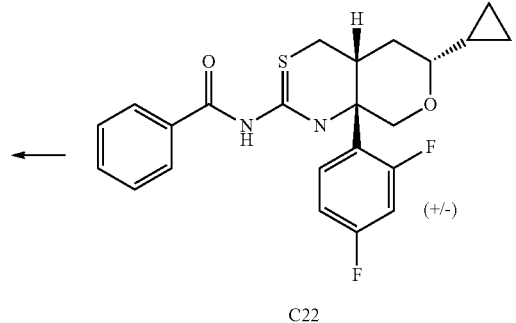

Step 1. Synthesis of [1-(2,2-diethoxyethoxy)but-3-en-1-yl]cyclopropane (C15)

1-Cyclopropylbut-3-en-1-ol (C14, see C. Tahtaoui et al., *J. Org. Chem.* 2010, 75, 3781-3785) (92%, 8.1 g, 66 mmol) was added to a 0° C. suspension of sodium hydride (60% in mineral oil, 8.25 g, 206 mmol) in tetrahydrofuran (105 mL). The cooling bath was removed and the suspension was stirred until the internal temperature reached 21° C. The reaction mixture was then cooled in an ice bath, and 2-bromo-1,1-diethoxyethane (97%, 18.5 mL, 119 mmol) was added drop-wise at a rate that maintained the internal temperature below 5° C. After warming to room temperature, the reaction mixture was heated to 58° C. for 27 hours. Sodium hydride (60% in mineral oil, 3.3 g, 83 mmol) and 2-bromo-1,1-diethoxyethane (97%, 10 mL, 64 mmol) were added again, and the reaction mixture was heated at mild reflux for 14 hours. It was then cooled to 0° C., slowly quenched with water (100 mL) and extracted with diethyl ether (3×200 mL). The combined organic layers were dried over sodium sulfate, filtered, and concentrated in vacuo; purification via silica gel chromatography (Gradient: 0% to 10% ethyl acetate in heptane) afforded the product as a colorless oil. Yield: 12.1 g, 53.0 mmol, 80%. $^1$H NMR (400 MHz, CDCl$_3$) δ 5.87-5.98 (m, 1H), 5.05-5.11 (m, 1H), 5.00-5.04 (m, 1H), 4.61 (t, J=5.3 Hz, 1H), 3.66-3.75 (m, 3H), 3.54-3.62 (m, 2H), 3.47 (dd, J=10.3, 5.5 Hz, 1H), 2.70 (dt, J=8.4, 6.0 Hz, 1H), 2.36-2.41 (m, 2H), 1.22 (t, J=7.0 Hz, 3H), 1.22 (t, J=7.0 Hz, 3H), 0.80-0.90 (m, 1H), 0.54-0.62 (m, 1H), 0.35-0.50 (m, 2H), 0.07-0.14 (m, 1H).

Step 2. Synthesis of [(1-cyclopropylbut-3-en-1-yl)oxy]acetaldehyde (C16)

A mixture of [1-(2,2-diethoxyethoxyl)but-3-en-1-yl]cyclopropane (C15) (2.97 g, 13.0 mmol), aqueous hydrochloric acid (1 M, 39 mL, 39 mmol) and tetrahydrofuran (39 mL) was stirred at room temperature for 12.5 hours, then heated to 40° C. for 3 hours. The reaction mixture was cooled to room temperature and slowly transferred into a stirring biphasic mixture of saturated aqueous sodium bicarbonate solution (200 mL) and diethyl ether (200 mL). The aqueous layer was extracted with diethyl ether (2×100 mL) and the combined organic extracts were dried over sodium sulfate, filtered, and concentrated in vacuo (900 mbar, 60° C.) to afford the product as a colorless oil (3.63 g), which contained residual diethyl ether and tetrahydrofuran by $^1$H NMR analysis. This material was taken directly into the following step. $^1$H NMR (400 MHz, CDCl$_3$) δ 9.76-9.78 (m, 1H), 5.86-5.98 (m, 1H), 5.04-5.15 (m, 2H), 4.15 (br AB quartet, $J_{AB}$=17.8 Hz, $\Delta v_{AB}$=22.8 Hz, 2H), 2.71 (dt, J=8.8, 5.9 Hz, 1H), 2.41-2.47 (m, 2H), 0.81-0.91 (m, 1H), 0.58-0.66 (m, 1H), 0.49-0.57 (m, 1H), 0.31-0.38 (m, 1H), 0.08-0.15 (m, 1H).

Step 3. Synthesis of 2-[(1-cyclopropylbut-3-en-1-yl)oxy]-N-hydroxyethanimine (C17)

[(1-Cyclopropylbut-3-en-1-yl)oxy]acetaldehyde (C16) (3.63 g from the previous step, ≤13.0 mmol) was dissolved in a 2:1 mixture of ethanol and water (39 mL). Sodium acetate (5.32 g, 64.9 mmol) was added; after the reaction mixture had been stirred for 15 minutes, hydroxylamine hydrochloride (98%, 2.76 g, 38.9 mmol) was added. The reaction mixture was heated to 60° C. for 5 minutes, at which time water (4×1 mL) was added until a solution formed. After 1 hour at 60° C., the reaction mixture was cooled, concentrated under reduced pressure to remove ethanol, and diluted with saturated aqueous sodium chloride solution (100 mL). The mixture was extracted with diethyl ether (3×100 mL), and the combined organic layers were dried over sodium sulfate, filtered, and concentrated in vacuo at 22° C. Silica gel chromatography (0% to 25% ethyl acetate in heptane) provided the product as a thick, opaque oil. By $^1$H NMR analysis, this material consisted of a roughly 1:1 mixture of E and Z oxime isomers. Yield: 1.771 g, 10.47 mmol, 81% over two steps. $^1$H NMR (400 MHz, CDCl$_3$) δ [7.50 (dd, J=5.7, 5.6 Hz) and 6.92-6.99 (m), total 1H], 5.84-5.97 (m, 1H), 5.03-5.15 (m, 2H), {[4.53 (dd, half of ABX pattern, J=16.4, 3.5 Hz) and 4.41 (dd, half of ABX pattern, J=16.4, 3.6 Hz)] and [4.27 (dd, half of ABX pattern, J=12.9, 5.5 Hz) and 4.16 (dd, half of ABX pattern, J=12.9, 5.8 Hz)], total 2H}, 2.65-2.74 (m, 1H), 2.37-2.44 (m, 2H), 0.81-0.91 (m, 1H), 0.59-0.68 (m, 1H), 0.47-0.56 (m, 1H), 0.35-0.44 (m, 1H), 0.07-0.15 (m, 1H).

Step 4. Synthesis of rel-(3aR,5R)-5-cyclopropyl-3,3a,4,5-tetrahydro-7H-pyrano[3,4-c][1,2]oxazole (C18)

An aqueous solution of sodium hypochlorite (6.15% solution, 27.1 mL, 22.4 mmol) was added drop-wise over 24 minutes to a solution of 2-[(1-cyclopropylbut-3-en-1-yl)oxy]-N-hydroxyethanimine (C17) (1.85 g, 10.9 mmol) and triethylamine (0.114 mL, 0.818 mmol) in dichloromethane (64 mL) that was immersed in a room temperature water bath. The rate of addition was adjusted to maintain the internal temperature of the reaction between 19.5° C. and 22.8° C. After completion of the addition, the reaction mixture was diluted with water (50 mL) and the aqueous layer was extracted with dichloromethane (3×50 mL). The combined organic layers were washed with saturated aqueous sodium chloride solution (50 mL), dried over sodium sulfate, filtered, and concentrated in vacuo (300 mbar, 40° C.) to provide the product as a pale yellow oil. The indicated relative stereochemistry of compound C18 was assigned based on nuclear Overhauser enhancement studies, which revealed an interaction between the methine protons on carbons 3a and 5. Yield: 1.73 g, 10.3 mmol, 94%. GCMS m/z 167 [M+]. $^1$H NMR (400 MHz, CDCl$_3$) δ 4.73 (d, J=13.5 Hz, 1H), 4.61 (dd, J=10.2, 8.0 Hz, 1H), 4.14 (dd, J=13.5, 1.0 Hz, 1H), 3.80 (dd, J=11.5, 8.0 Hz, 1H), 3.36-3.48 (m, 1H), 2.83 (ddd, J=11.0, 8.0, 1.8 Hz, 1H), 2.31 (ddd, J=13.0, 6.5, 1.5 Hz, 1H), 1.64 (ddd, J=12.8, 11.4, 11.3 Hz, 1H), 0.89-0.98 (m, 1H), 0.51-0.64 (m, 2H), 0.38-0.45 (m, 1H), 0.21-0.28 (m, 1H).

Step 5. Synthesis of rel-(3aR,5R,7aS)-5-cyclopropyl-7a-(2,4-difluorophenyl)hexahydro-1H-pyrano[3,4-c][1,2]oxazole (C19)

Boron trifluoride diethyl etherate (2.97 mL, 24.1 mmol) was added drop-wise to a solution of rel-(3aR,5R)-5-cyclopropyl-3,3a,4,5-tetrahydro-7H-pyrano[3,4-c][1,2]oxazole (C18) (1.67 g, 9.99 mmol) in toluene (150 mL) at an internal temperature of −72.5° C. The reaction mixture was stirred at −73° C. to −76° C. for 30 minutes, then treated with 2,4-difluoro-1-iodobenzene (98%, 1.37 mL, 11.2 mmol) in one portion. While the reaction temperature was maintained below −73° C., n-butyllithium (2.5 M in hexanes, 4.24 mL, 10.6 mmol) was added in a drop-wise manner over 15 minutes. The reaction mixture was stirred at −73° C. to −75° C. for 1 hour, then was quenched with saturated aqueous ammonium chloride solution (350 mL) at −74° C. and allowed to warm to room temperature. The resulting mixture was extracted with ethyl acetate (400 mL), and the aqueous layer was extracted with additional ethyl acetate (250 mL and 100 mL); the combined organic layers were dried over sodium sulfate, filtered, and concentrated in vacuo. Chromatography on silica gel (Gradient: 0% to 30% ethyl acetate in heptane) afforded the product as a white solid after azeotroping twice with dichloromethane. Yield: 2.16 g, 7.68 mmol, 77%. GCMS m/z 281 [M+]. $^1$H NMR (400 MHz, CDCl$_3$) δ 7.88-7.98 (m, 1H), 6.84-6.93 (m, 1H), 6.79 (ddd, J=11.9, 8.6, 2.4 Hz, 1H), 6.34 (br s, 1H), 4.04 (br d, J=12.7 Hz, 1H), 3.83 (d, J=12.5 Hz, 1H), 3.72 (d, J=7.0 Hz, 1H), 3.54 (dd, J=6.8, 5.1 Hz, 1H), 2.99-3.08 (m, 1H), 2.86-2.95 (m, 1H), 1.99 (br dd, J=13.8, 6.8 Hz, 1H), 1.56-1.68 (m, 1H), 0.88-1.00 (m, 1H), 0.51-0.64 (m, 2H), 0.37-0.47 (m, 1H), 0.24-0.33 (m, 1H).

Step 6. Synthesis of rel-[(2R,4R,5S)-5-amino-2-cyclopropyl-5-(2,4-difluorophenyl)tetrahydro-2H-pyran-4-yl]methanol (C20)

rel-(3aR,5R,7aS)-5-Cyclopropyl-7a-(2,4-difluorophenyl)hexahydro-1H-pyrano[3,4-c][1,2]oxazole (C19) (1.19 g, 4.23 mmol) was converted to the product according to the method described for the synthesis of [(2R,4R,5S)-5-amino-2-[(benzyloxy)methyl]-5-(2,4-difluorophenyl)tetrahydro-2H-pyran-4-yl]methanol (C6) in Preparation P1. The product was obtained as a thick, pale amber gum (1.22 g), which was taken directly to the following step without additional purification. LCMS m/z 284.1 [M+H+]. $^1$H NMR (400 MHz, CDCl$_3$) δ 7.61-7.77 (br m, 1H), 6.90-7.05 (br m, 1H), 6.82 (ddd, J=12.7, 8.6, 2.6 Hz, 1H), 4.13 (dd, J=11.5, 2.5 Hz, 1H), 3.55 (br dd, J=11, 2 Hz, 1H), 3.32-3.49 (br m, 2H), 2.89 (ddd, J=11.3, 8.2, 2.5 Hz, 1H), 2.03-2.34 (br m, 2H), 1.81 (ddd, J=14.0, 4.0, 2.6 Hz, 1H), 1.01-1.13 (br m, 1H), 0.53-0.65 (m, 2H), 0.41-0.48 (m, 1H), 0.24-0.32 (m, 1H).

Step 7. Synthesis of rel-N-{[(3S,4R,6R)-6-cyclopropyl-3-(2,4-difluorophenyl)-4-(hydroxymethyl)tetrahydro-2H-pyran-3-yl]carbamothioyl}benzamide (C21)

Benzoyl isothiocyanate (0.540 mL, 4.02 mmol) was added drop-wise to a solution of rel-[(2R,4R,5S)-5-amino-2-cyclopropyl-5-(2,4-difluorophenyl)tetrahydro-2H-pyran-4-yl]methanol (C20) (1.20 g, 4.23 mmol) in dichloromethane (45 mL). After the reaction mixture had stirred at room temperature for 15 hours, it was partitioned between aqueous hydrochloric acid (0.1 M, 20 mL) and dichloromethane (35 mL). The organic layer was washed with saturated aqueous sodium bicarbonate solution (25 mL) and with saturated aqueous sodium chloride solution (25 mL), then dried over sodium sulfate, filtered, and concentrated in vacuo. Purification via silica gel chromatography (Gradient: 0% to 45% ethyl acetate in heptane) provided the product as a white solid. Yield: 1.69 g, 3.78 mmol, 89%. LCMS m/z 447.2 [M+H+]. $^1$H NMR (400 MHz, CD$_3$CN) δ 11.64 (br s, 1H), 9.28 (br s, 1H), 7.89-7.93 (m, 2H), 7.64-7.69 (m, 1H), 7.52-7.58 (m, 2H), 7.44-7.58 (br m, 1H), 6.86-6.99 (m, 2H), 3.48-3.86 (br m, 2H), 3.35-3.47 (m, 1H), 3.01 (ddd, J=11.3, 7.6, 2.7 Hz, 1H), 2.89-3.0 (br m, 1H), 2.3-2.6 (br m, 1H), 1.96-2.03 (m, 1H), 1.7-1.9 (br m, 1H), 0.90-1.00 (m, 1H), 0.44-0.53 (m, 2H), 0.34-0.40 (m, 1H), 0.26-0.31 (m, 1H).

Step 8. Synthesis of rel-N-[(4aR,6R,8aS)-6-cyclopropyl-8a-(2,4-difluorophenyl)-4,4a,5,6,8,8a-hexahydropyrano[3,4-d][1,3]thiazin-2-yl]benzamide (C22)

rel-N-{[(3S,4R,6R)-6-Cyclopropyl-3-(2,4-difluorophenyl)-4-(hydroxymethyl)tetrahydro-2H-pyran-3-yl]carbamothioyl}benzamide (C21) was converted to the product using the method described for synthesis of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8) in Preparation P1. The product was obtained as a solid. Yield: 1.42 g, 3.31 mmol, 88%. LCMS m/z 429.1 [M+H+]. $^1$H NMR (400 MHz, CDCl$_3$) δ 11.7-12.5 (v br s, 1H), 8.24 (br d, J=7.6 Hz, 2H), 7.48-7.54 (m, 1H), 7.38-7.48 (m, 3H), 6.82-6.97 (m, 2H), 4.08 (br dd, J=12.4, 1.3 Hz, 1H), 3.80 (d, J=12.3 Hz, 1H), 3.05-3.13 (m, 1H), 2.93-3.04 (m, 2H), 2.64 (dd, J=12.8, 2.6 Hz, 1H), 2.05-2.18 (m, 1H), 1.75-1.83 (m, 1H), 0.96-1.06 (m, 1H), 0.50-0.62 (m, 2H), 0.40-0.46 (m, 1H), 0.22-0.29 (m, 1H).

Step 9. Synthesis of (4aR,6R,8aS)-6-cyclopropyl-8a-(2,4-difluorophenyl)-4,4a,5,6,8,8a-hexahydropyrano[3,4-d][1,3]thiazin-2-amine (2)

rel-N-[(4aR,6R,8aS)-6-Cyclopropyl-8a-(2,4-difluorophenyl)-4,4a,5,6,8,8a-hexahydropyrano[3,4-d][1,3]thiazin-2-yl]benzamide (C22) (480 mg, 1.12 mmol) was combined with methanol (20 mL) and 1,8-diazabicyclo[5.4.0]undec-7-ene (95%, 130 μL, 0.83 mmol) and heated at 80° C. for 9 hours. The reaction mixture was cooled and concentrated in vacuo, then partitioned between dichloromethane (100 mL) and water (40 mL). The organic layer was dried over sodium sulfate, filtered, and concentrated under reduced pressure. The residue was purified via silica gel chromatography (Gradient: 0% to 15% methanol in dichloromethane) to provide the racemic product, which was separated into its enantiomers using supercritical fluid chromatography (Column: Phenomenex Lux® Cellulose-4, 5 μm; Eluent: 7:3 carbon dioxide/methanol containing 0.2% isopropylamine). The first-eluting enantiomer provided the product as a pale yellow solid. The indicated absolute stereochemistry was assigned to compound 2 on the basis of this compound's biological activity; its enantiomer C23 (below) proved essentially inactive (see Table 3). Yield: 147 mg, 0.453 mmol, 40%. LCMS m/z 325.2 [M+H$^+$]. $^1$H NMR (400 MHz, CDCl$_3$) δ 7.36 (ddd, J=9, 9, 6.7 Hz, 1H), 6.82-6.89 (m, 1H), 6.78 (ddd, J=12.4, 8.6, 2.6 Hz, 1H), 4.01 (dd, J=11.0, 2.4 Hz, 1H), 3.79 (d, J=11.2 Hz, 1H), 2.95 (dd, J=12.2, 4.2 Hz, 1H), 2.79-2.90 (m, 2H), 2.60 (dd, J=12.3, 2.7 Hz, 1H), 1.88-2.00 (m, 1H), 1.61 (ddd, J=13.4, 4.1, 2.2 Hz, 1H), 0.95-1.05 (m, 1H), 0.48-0.60 (m, 2H), 0.39-0.46 (m, 1H), 0.19-0.26 (m, 1H).

The second-eluting enantiomer, also obtained as a pale yellow solid, was assigned as (4aS,6S,8aR)-6-cyclopropyl-8a-(2,4-difluorophenyl)-4,4a,5,6,8,8a-hexahydropyrano[3,4-d][1,3]thiazin-2-amine (C23). Yield: 144 mg, 0.444 mmol, 40%. LCMS m/z 325.2 [M+H$^+$]. $^1$H NMR (400 MHz, CDCl$_3$) δ 7.36 (ddd, J=9.0, 9.0, 6.6 Hz, 1H), 6.83-6.90 (m, 1H), 6.78 (ddd, J=12.5, 8.6, 2.5 Hz, 1H), 4.01 (dd, J=11.1, 2.2 Hz, 1H), 3.80 (d, J=11.2 Hz, 1H), 2.95 (dd, J=12.3, 4.1 Hz, 1H), 2.80-2.91 (m, 2H), 2.61 (dd, J=12.3, 2.7 Hz, 1H), 1.88-2.00 (m, 1H), 1.62 (ddd, J=13.3, 4.0, 2.2 Hz, 1H), 0.95-1.05 (m, 1H), 0.48-0.60 (m, 2H), 0.38-0.46 (m, 1H), 0.19-0.26 (m, 1H).

Example 3

(4R,4aR,6R,8aS)-6-Cyclopropyl-8a-(2,4-difluorophenyl)-4-methyl-4,4a,5,6,8,8a-hexahydropyrano[3,4-d][1,3]thiazin-2-amine, trifluoroacetate salt (3)

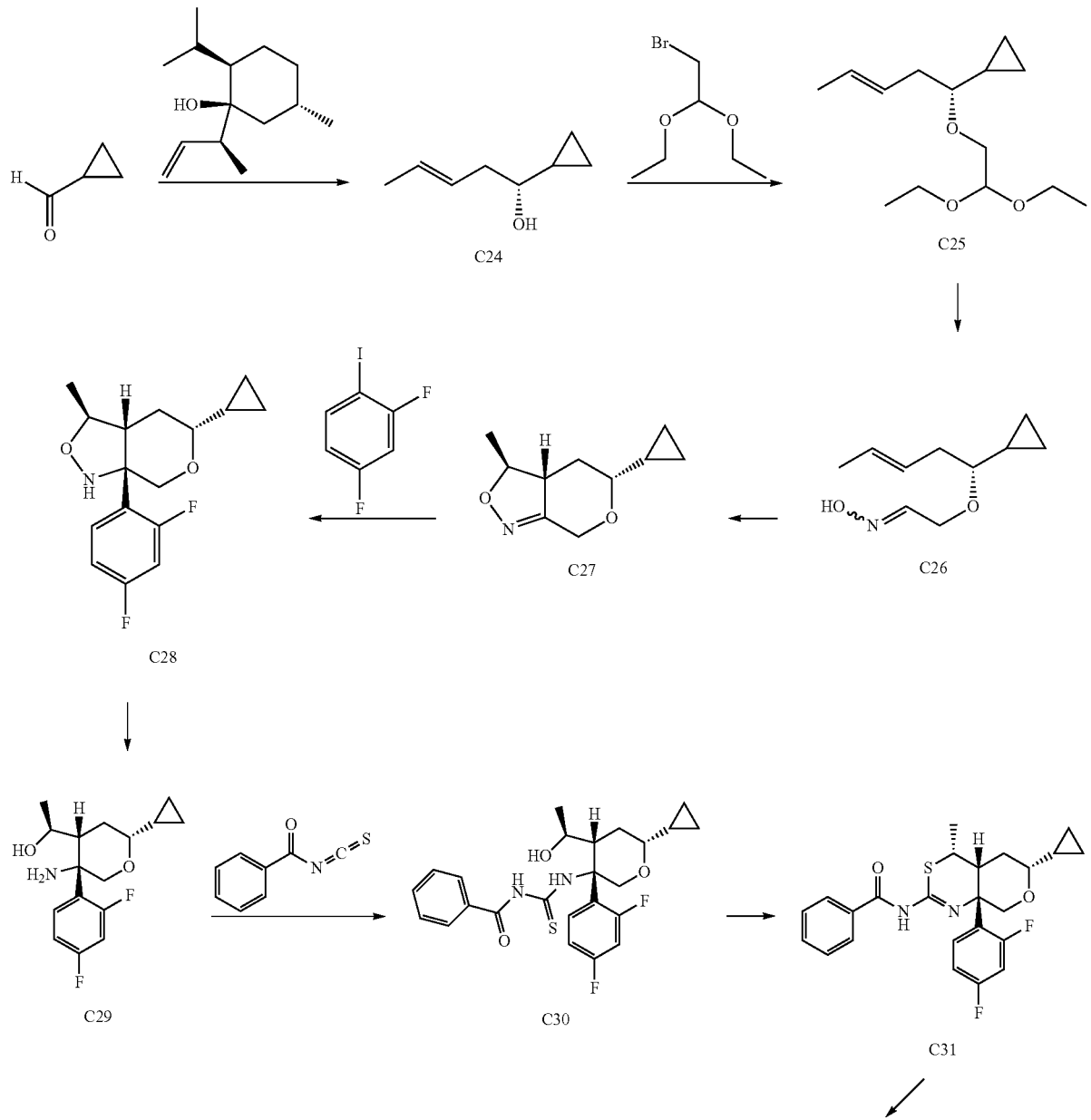

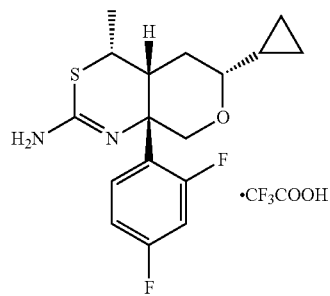

Step 1. Synthesis of (1R,3E)-1-cyclopropylpent-3-en-1-ol (C24)

Using the method described by J. Nokami et al., *J. Am. Chem. Soc.* 2001, 123, 9168-9169, cyclopropanecarbaldehyde was reacted with (1S,2R,5S)-1-[(2S)-but-3-en-2-yl]-5-methyl-2-(propan-2-yl)cyclohexanol [this crotylation reagent was derived from (+)-menthol] to afford the product as an oil. Yield: 600 mg, 4.75 mmol, 100%. $^1$H NMR (400 MHz, CDCl$_3$), characteristic peaks: δ 5.45-5.63 (m, 2H), 2.86-2.92 (m, 1H), 2.33-2.41 (m, 1H), 2.20-2.29 (m, 1H), 1.69-1.72 (m, 3H), 0.47-0.56 (m, 2H), 0.27-0.37 (m, 1H), 0.16-0.26 (m, 1H).

Step 2. Synthesis of [(1R,3E)-1-(2,2-diethoxyethoxyl)pent-3-en-1-yl]cyclopropane (C25)

(1R,3E)-1-Cyclopropylpent-3-en-1-ol (C24) was converted to the product according to the method used for the synthesis of ({[(2R)-2-(2,2-diethoxyethoxyl)pent-4-en-1-yl]oxy}methyl)benzene (C2) in Preparation P1, except that all reagents were combined at 0° C. The product was obtained as a colorless oil. Yield: 550 mg, 2.27 mmol, 48%. $^1$H NMR (400 MHz, CDCl$_3$) δ 5.44-5.59 (m, 2H), 4.62 (dd, J=5.3, 5.3 Hz, 1H), 3.66-3.76 (m, 3H), 3.54-3.63 (m, 2H), 3.47 (dd, J=10.3, 5.5 Hz, 1H), 2.65 (dt, J=8.5, 5.9 Hz, 1H), 2.28-2.33 (m, 2H), 1.65-1.68 (m, 3H), 1.23 (t, J=7.1 Hz, 3H), 1.23 (t, J=7.0 Hz, 3H), 0.79-0.88 (m, 1H), 0.53-0.60 (m, 1H), 0.42-0.50 (m, 1H), 0.34-0.41 (m, 1H), 0.06-0.13 (m, 1H).

Step 3. Synthesis of 2-{[(1R,3E)-1-cyclopropylpent-3-en-1-yl]oxy}-N-hydroxyethanimine (C26)

[(1R,3E)-1-(2,2-Diethoxyethoxyl)pent-3-en-1-yl]cyclopropane (C25) was converted to the product using the method described for synthesis of 2-{[(2R)-1-(benzyloxy)pent-4-en-2-yl]oxy}-N-hydroxyethanimine (C3) in the section "Alternate conversion of C2 to C4." In this case, purification was carried out using silica gel chromatography (Gradient: 0% to 80% ethyl acetate in heptane) to provide the product as a colorless oil. By $^1$H NMR, this was assigned as a roughly 1:1 mixture of oxime isomers. Yield: 200 mg, 1.09 mmol, 48%. $^1$H NMR (400 MHz, CDCl$_3$), characteristic peaks: δ [7.50 (dd, J=5.8, 5.6 Hz) and 6.93 (dd, J=3.6, 3.6 Hz), total 1H], 7.46 and 7.21 (2 br s, total 1H), 5.45-5.63 (m, 2H), {[4.50 (dd, half of ABX pattern, J=16.3, 3.6 Hz) and 4.40 (dd, half of ABX pattern, J=16.3, 3.7 Hz)] and [4.25 (dd, half of ABX pattern, J=12.8, 5.6 Hz) and 4.15 (dd, half of ABX pattern, J=12.9, 5.8 Hz)], total 2H}, 2.59-2.68 (m, 1H), 1.66-1.72 (m, 3H), 0.45-0.54 (m, 1H), 0.29-0.43 (m, 1H), 0.18-0.24 and 0.06-0.14 (2 m, total 1H).

Step 4. Synthesis of (3S,3aR,5R)-5-cyclopropyl-3-methyl-3,3a,4,5-tetrahydro-7H-pyrano[3,4-c][1,2]oxazole (C27)

An aqueous solution of sodium hypochlorite (6.15% solution, 0.7 mL, 0.6 mmol) was added drop-wise to a solution of 2-{[(1R,3E)-1-cyclopropylpent-3-en-1-yl]oxy}-N-hydroxyethanimine (C26) (200 mg, 1.09 mmol) in dichloromethane (10 mL), followed by addition of triethylamine (11 μL, 79 μmol). The reaction mixture was stirred for 1 hour, then treated with a drop of triethylamine and additional aqueous sodium hypochlorite solution (6.15%, 0.5 mL, 0.4 mmol). After 20 minutes, the reaction mixture was partitioned between water (10 mL) and dichloromethane (20 mL); the organic layer was dried over sodium sulfate, filtered, and concentrated in vacuo. Purification via silica gel chromatography (Gradient: 0% to 100% ethyl acetate in heptane) provided the product as an oil. The indicated relative stereochemistry of compound C27 was assigned based on nuclear Overhauser enhancement studies, which revealed interactions of the methine proton on carbon 3a with both the protons of the methyl group on carbon 3 and the methine proton on carbon 5. Yield: 150 mg, 0.828 mmol, 76%. $^1$H NMR (400 MHz, CDCl$_3$) δ 4.64 (d, J=13.5 Hz, 1H), 4.17-4.25 (m, 1H), 4.08 (dd, J=13.6, 1.3 Hz, 1H), 2.84-2.93 (m, 1H), 2.76 (ddd, J=11.0, 7.9, 1.9 Hz, 1H), 2.21 (dddd, J=12.9, 6.6, 1.9, 0.5 Hz, 1H), 1.57 (ddd, J=12.9, 11.4, 11.4 Hz, 1H), 1.45 (d, J=6.2 Hz, 3H), 0.86-0.96 (m, 1H), 0.48-0.61 (m, 2H), 0.35-0.42 (m, 1H), 0.19-0.26 (m, 1H).

Step 5. Synthesis of (3S,3aR,5R,7aS)-5-cyclopropyl-7a-(2,4-difluorophenyl)-3-methylhexahydro-1H-pyrano[3,4-c][1,2]oxazole (C28)

(3S,3aR,5R)-5-Cyclopropyl-3-methyl-3,3a,4,5-tetrahydro-7H-pyrano[3,4-c][1,2]oxazole (C27) was converted to the product according to the method described for synthesis of rel-(3aR,5R,7aS)-5-cyclopropyl-7a-(2,4-difluorophenyl)hexahydro-1H-pyrano[3,4-c][1,2]oxazole (C19) in Example 2. The product was obtained as a gum. Yield: 60 mg, 0.20 mmol, 40%. $^1$H NMR (400 MHz, CDCl$_3$) δ 7.99 (ddd, J=9.2, 9.0, 6.8 Hz, 1H), 6.90 (dddd, J=8.9, 7.9, 2.6, 1.0 Hz, 1H), 6.79 (ddd, J=11.9, 8.7, 2.5 Hz, 1H), 6.31 (br s, 1H), 4.03-4.10 (m, 1H), 3.89 (dd, half of ABX pattern, J=12.8, 2.0 Hz, 1H), 3.80 (br dd, half of ABX pattern, J=12.8, 1.5 Hz, 1H), 2.79-2.91 (m, 2H), 2.16 (ddd, J=14.3, 7.5, 2.5 Hz, 1H), 1.64 (dddd, J=14.2, 10.7, 10.7, 1.7 Hz, 1H), 0.90-0.99 (m, 1H), 0.79 (d, J=6.5 Hz, 3H), 0.52-0.64 (m, 2H), 0.39-0.45 (m, 1H), 0.24-0.31 (m, 1H).

Step 6. Synthesis of (1S)-1-[(2R,4R,5S)-5-amino-2-cyclopropyl-5-(2,4-difluorophenyl)tetrahydro-2H-pyran-4-yl]ethanol (C29)

(3S,3aR,5R,7aS)-5-Cyclopropyl-7a-(2,4-difluorophenyl)-3-methyl hexahydro-1H-pyrano[3,4-c][1,2]oxazole (C28) was converted to the product using the method described for synthesis of [(2R,4R,5S)-5-amino-2-[(benzyloxy)methyl]-5-(2,4-difluorophenyl)tetrahydro-2H-pyran-4-yl]methanol (C6) in Preparation P1. The resulting oil was used in the next step without additional purification. Yield: 0.11 g, 0.37 mmol, 87%. LCMS m/z 298.2 [M+H$^+$].

Step 7. Synthesis of N-({(3S,4R,6R)-6-cyclopropyl-3-(2,4-difluorophenyl)-4-[(1S)-1-hydroxyethyl]tetrahydro-2H-pyran-3-yl}carbamothioyl)benzamide (C30)

Benzoyl isothiocyanate (47 µL, 0.35 mmol) was slowly added to a 0° C. solution of (1S)-1-[(2R,4R,5S)-5-amino-2-cyclopropyl-5-(2,4-difluorophenyl)tetrahydro-2H-pyran-4-yl]ethanol (C29) (0.11 g, 0.37 mmol) in dichloromethane (6 mL), and the reaction mixture was allowed to stir in the ice bath for 18 hours. After removal of solvent in vacuo, the residue was purified via chromatography on silica gel (Gradient: 0% to 100% ethyl acetate in heptane) to provide the product as an off-white foam. Yield: 94 mg, 0.20 mmol, 54%. LCMS m/z 461.2 [M+H$^+$]. $^1$H NMR (400 MHz, CDCl$_3$), characteristic peaks: δ 11.85 (v br s, 1H), 8.90 (br s, 1H), 7.91 (br d, J=7 Hz, 2H), 7.63-7.68 (m, 1H), 7.52-7.58 (m, 2H), 6.84-6.91 (m, 1H), 6.68-6.82 (br m, 1H), 3.84-3.96 (br m, 1H), 2.90-2.99 (br m, 1H), 1.84-1.94 (br m, 1H), 1.02-1.14 (br m, 1H), 0.47-0.65 (m, 3H), 0.28-0.38 (br m, 1H).

Step 8. Synthesis of N-[(4R,4aR,6R,8aS)-6-cyclopropyl-8a-(2,4-difluorophenyl)-4-methyl-4,4a,5,6,8,8a-hexahydropyrano[3,4-d][1,3]thiazin-2-yl]benzamide (C31)

Diethyl azodicarboxylate (92 µL, 0.59 mmol) was added to a 0° C. solution of triphenylphosphine (153 mg, 0.583 mmol) in tetrahydrofuran (7 mL), and the mixture was stirred for 10 minutes in the ice bath. A solution of N-({(3S,4R,6R)-6-cyclopropyl-3-(2,4-difluorophenyl)-4-[(1S)-1-hydroxyethyl]tetrahydro-2H-pyran-3-yl}carbamothioyl)benzamide (C30) (90 mg, 0.20 mmol) in tetrahydrofuran (2 mL) was added drop-wise to the reaction mixture, which was then stirred for 1 hour under ice cooling. The reaction mixture was concentrated in vacuo; purification via silica gel chromatography (Gradient: 0% to 80% ethyl acetate in heptane) afforded the product as a gum. Yield: 45 mg, 0.10 mmol, 50%. LCMS m/z 441.1 [M–H$^+$].

Step 9. Synthesis of (4R,4aR,6R,8aS)-6-cyclopropyl-8a-(2,4-difluorophenyl)-4-methyl-4,4a,5,6,8,8a-hexahydropyrano[3,4-d][1,3]thiazin-2-amine, trifluoroacetate salt (3)

N-[(4R,4aR,6R,8aS)-6-Cyclopropyl-8a-(2,4-difluorophenyl)-4-methyl-4,4a,5,6,8,8a-hexahydropyrano[3,4-d][1,3]thiazin-2-yl]benzamide (C31) was converted to the product according to the method described for the synthesis of the racemate of (4aR,6R,8aS)-6-cyclopropyl-8a-(2,4-difluorophenyl)-4,4a,5,6,8,8a-hexahydropyrano[3,4-d][1,3]thiazin-2-amine (2) in Example 2. After the chromatography on silica gel (Gradient: 0% to 15% methanol in dichloromethane), the sample (a white solid) was purified using reversed phase HPLC (Column: Waters Sunfire C18, 5 µm; Mobile phase A: 0.05% trifluoroacetic acid in water (v/v); Mobile phase B: 0.05% trifluoroacetic acid in acetonitrile (v/v); Gradient: 5% to 100% B). Yield: 12.2 mg, 36.0 µmol, 36%. LCMS m/z 339.1 [M+H$^+$]. $^1$H NMR (600 MHz, DMSO-d$_6$), characteristic peaks: δ 7.34-7.40 (m, 1H), 7.21-7.31 (m, 2H), 3.83-3.89 (m, 2H), 3.01-3.07 (m, 1H), 2.92-2.98 (m, 1H), 1.87 (br d, J=13 Hz, 1H), 1.32-1.40 (m, 1H), 1.25 (d, J=7.0 Hz, 3H), 0.92-0.99 (m, 1H), 0.44-0.52 (m, 2H), 0.33-0.38 (m, 1H), 0.29-0.33 (m, 1H).

Example 4

(4aR,6R,8aS)-8a-(2,4-Difluorophenyl)-6-(oxetan-2-yl)-4,4a,5,6,8,8a-hexahydropyrano[3,4-d][1,3]thiazin-2-amine (4)

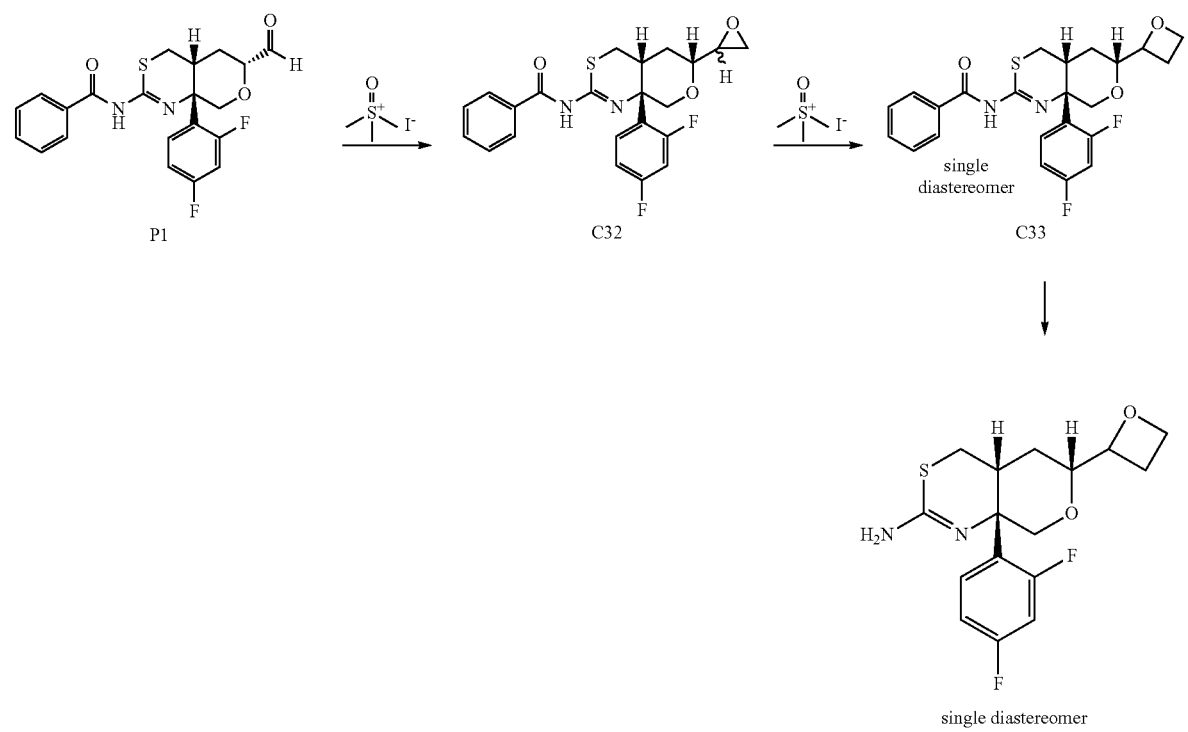

single diastereomer

Step 1. Synthesis of N-[(4aR,6R,8aS)-8a-(2,4-difluorophenyl)-6-(oxiran-2-yl)-4,4a,5,6,8,8a-hexahydropyrano[3,4-d][1,3]thiazin-2-yl]benzamide (C32)

Sodium hydride (60% in mineral oil, 295 mg, 7.38 mmol) was added to a solution of trimethylsulfoxonium iodide (97%, 1.83 g, 8.07 mmol) in dimethyl sulfoxide (15 mL). After 30 minutes, the mixture was cooled in an ice bath, and a solution of N-[(4aR,6R,8aS)-8a-(2,4-difluorophenyl)-6-formyl-4,4a,5,6,8,8a-hexahydropyrano[3,4-d][1,3]thiazin-2-yl]benzamide (P1) (1.12 g, 2.69 mmol) in dimethyl sulfoxide (5 mL) was added. The reaction mixture was allowed to warm to room temperature and stir for 2 hours, at which time saturated aqueous ammonium chloride solution was added, followed by dichloromethane, and the mixture was washed twice with water and with saturated aqueous sodium chloride solution. The organic layer was dried over magnesium sulfate, filtered, and concentrated in vacuo. The product was obtained as a white foamy solid, estimated to be a roughly 4:3 mixture of diastereomers by LCMS analysis; this material was used without additional purification. Yield: 1.19 g, quantitative. LCMS m/z 431.1 [M+H$^+$].

Step 2. Synthesis of N-[(4aR,6R,8aS)-8a-(2,4-difluorophenyl)-6-(oxetan-2-yl)-4,4a,5,6,8,8a-hexahydropyrano[3,4-d][1,3]thiazin-2-yl]benzamide (C33)

Sodium hydride (60% in mineral oil, 225 mg, 5.62 mmol) was added to a solution of trimethylsulfoxonium iodide (97%, 1.45 g, 6.39 mmol) in dimethyl sulfoxide (7 mL). After 30 minutes, a solution of N-[(4aR,6R,8aS)-8a-(2,4-difluorophenyl)-6-(oxiran-2-yl)-4,4a,5,6,8,8a-hexahydropyrano[3,4-d][1,3]thiazin-2-yl]benzamide (C32) (1.10 g, 2.56 mmol) in dimethyl sulfoxide (3 mL) was added, and the reaction mixture was heated to 45° C. for 18 hours. After cooling to room temperature, the reaction mixture was quenched with saturated aqueous ammonium chloride solution, diluted with ethyl acetate, washed twice with water, and then with saturated aqueous sodium chloride solution. The organic layer was dried over magnesium sulfate, filtered, and concentrated under reduced pressure. Purification was carried out first by reversed phase chromatography (Column: Zymor HA-Dipyridyl, 5 µm; Gradient: 10% to 100% ethanol in heptane), then via supercritical fluid chromatography (Column: Chiral Technologies Chiralcel OJ-H, 5 µm; Eluent: 3:1 carbon dioxide/methanol) to afford the product. Yield: 19 mg, 0.043 mmol, 2%. This compound was assigned as a single diastereomer, of unknown absolute stereochemistry at the oxetane, by LCMS and $^1$H NMR analysis. LCMS m/z 445.2 [M+H$^+$]. $^1$H NMR (400 MHz, CDCl$_3$) δ 8.19-8.25 (m, 2H), 7.49-7.54 (m, 1H), 7.37-7.48 (m, 3H), 6.85-6.97 (m, 2H), 4.80 (ddd, J=7.9, 6.7, 6.5 Hz, 1H), 4.69 (ddd, J=8.5, 7.2, 6.0 Hz, 1H), 4.57 (ddd, J=9.1, 6.1, 6.0 Hz, 1H), 4.18 (dd, J=12.3, 1.8 Hz, 1H), 3.92 (ddd, J=11.6, 6.5, 2.1 Hz, 1H), 3.85 (d, J=12.2 Hz, 1H), 3.14-3.22 (m, 1H), 3.04 (dd, J=12.9, 4.1 Hz, 1H), 2.62-2.72 (m, 2H), 2.47-2.57 (m, 1H), 1.90-2.01 (m, 1H), 1.62 (ddd, J=13.4, 4.2, 2.4 Hz, 1H).

Step 3. Synthesis of (4aR,6R,8aS)-8a-(2,4-difluorophenyl)-6-(oxetan-2-yl)-4,4a,5,6,8,8a-hexahydropyrano[3,4-d][1,3]thiazin-2-amine (4)

1,8-Diazabicyclo[5.4.0]undec-7-ene (95%, 7.5 mg, 47 µmol) was added to a solution of N-[(4aR,6R,8aS)-8a-(2,4-difluorophenyl)-6-(oxetan-2-yl)-4,4a,5,6,8,8a-hexahydropyrano[3,4-d][1,3]thiazin-2-yl]benzamide (C33) (19 mg, 43 µmol) in methanol (0.5 mL), and the reaction mixture was heated at 80° C. for 3.5 hours. After cooling and removal of solvent in vacuo, purification was carried out via reversed phase HPLC (Column: Waters XBridge C18, 5 µm; Mobile phase A: 0.03% ammonium hydroxide in water (v/v); Mobile phase B: 0.03% ammonium hydroxide in acetonitrile (v/v); Gradient: 20% to 60% B), providing the product as a gum. Yield: 11.7 mg, 34.4 µmol, 73%. LCMS m/z 341.2 [M+H$^+$]. $^1$H NMR (600 MHz, DMSO-d$_6$) δ 7.35 (ddd, J=9.2, 9.2, 7.0 Hz, 1H), 7.16-7.22 (m, 1H), 7.07-7.11 (m, 1H), 4.55-4.60 (m, 1H), 4.46-4.51 (m, 1H), 4.34-4.38 (m, 1H), 3.90 (dd, J=10.5, 2.2 Hz, 1H), 3.64-3.69 (m, 1H), 3.59 (d, J=10.1 Hz, 1H), 2.46-2.75 (m, 5H), 1.54-1.62 (m, 1H), 1.36-1.41 (m, 1H).

Example 5 rel-(4S,4aR,6R,8aS)-6-Cyclopropyl-8a-(2,4-difluorophenyl)-4-(methoxymethyl)-4,4a,5,6,8,8a-hexahydropyrano[3,4-d][1,3]thiazin-2-amine, hydrochloride salt (5)

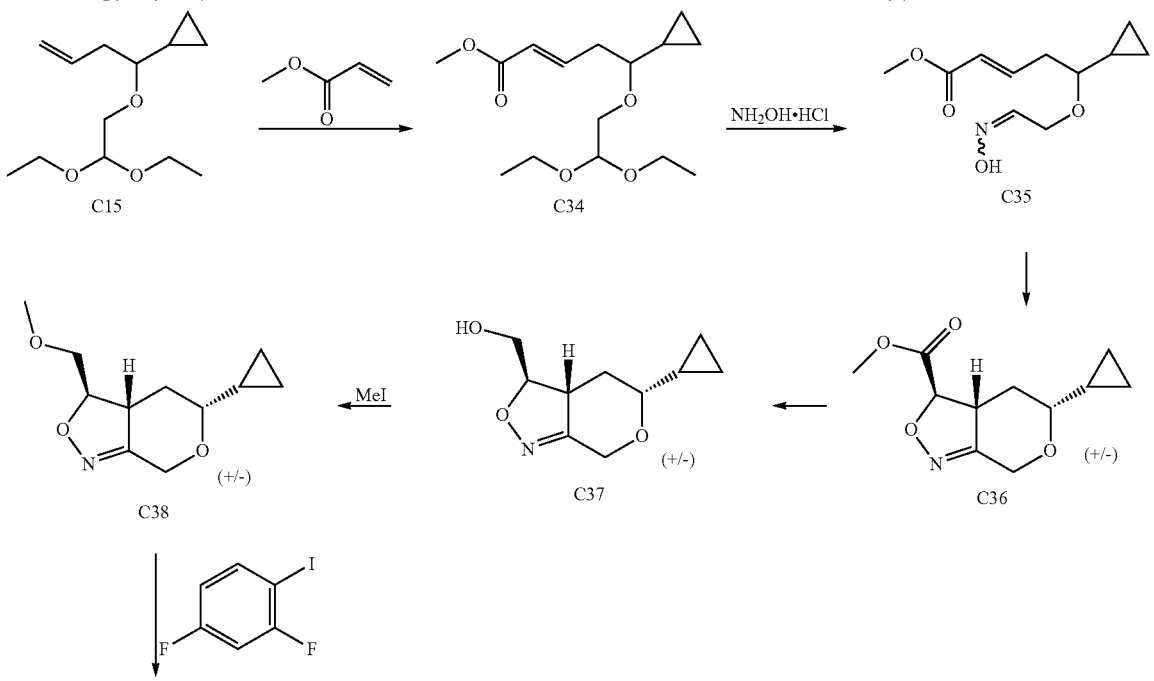

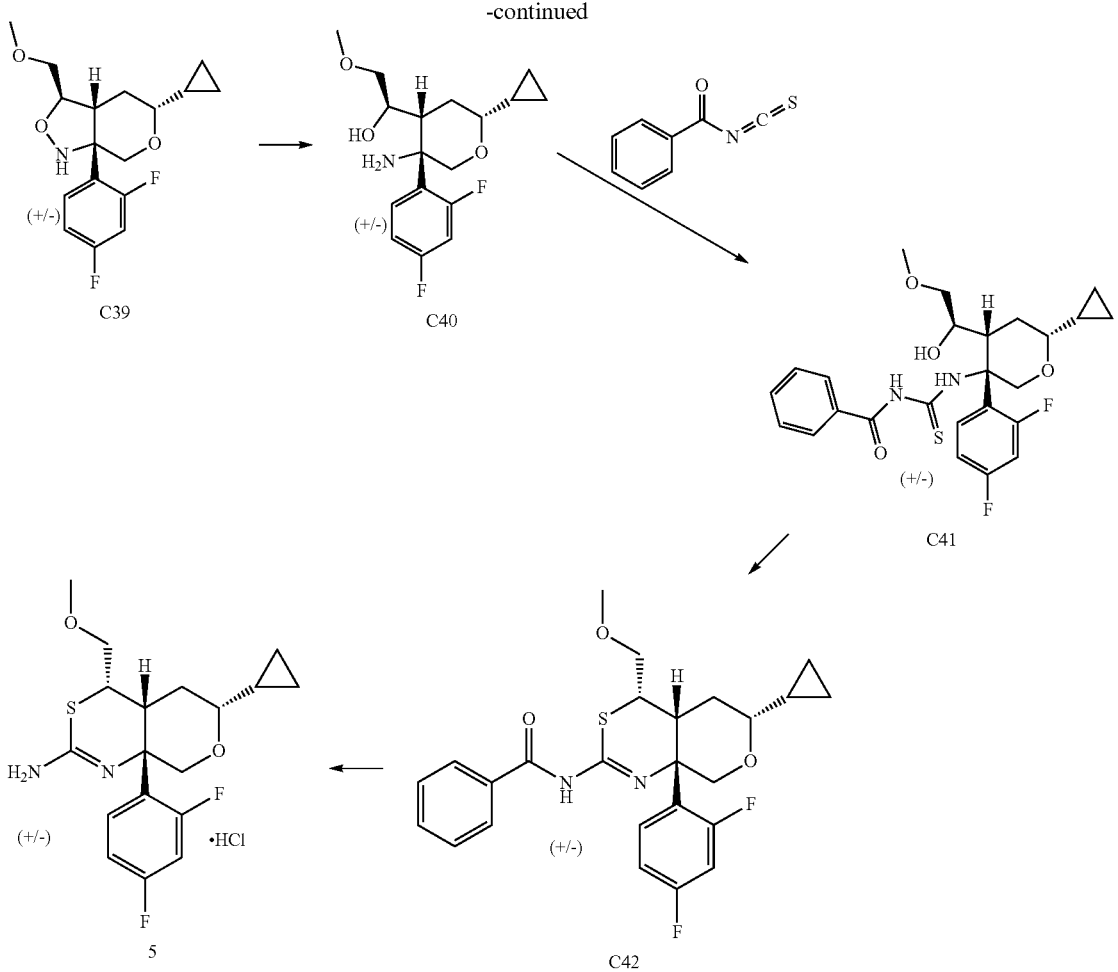

Step 1. Synthesis of methyl (2E)-5-cyclopropyl-5-(2,2-diethoxyethoxyl)pent-2-enoate (C34)

A solution of methyl prop-2-enoate (69.5 mL, 767 mmol) and benzylidene[1,3-bis(2,4,6-trimethylphenyl)imidazolidin-2-ylidene]dichloro(tricyclohexylphosphine)ruthenium (Grubbs catalyst, second generation) (1.30 g, 1.53 mmol) in dichloromethane (102 mL) was added to a solution of [1-(2,2-diethoxyethoxyl)but-3-en-1-yl]cyclopropane (C15) (7.00 g, 30.7 mmol) in dichloromethane (102 mL), and the reaction mixture was stirred at room temperature for 3 hours. After removal of solvent under reduced pressure, the residue was mixed with diethyl ether and filtered through Celite. The filter pad was washed with additional diethyl ether, and the combined filtrates were concentrated in vacuo. Purification using silica gel chromatography (Gradient: 0% to 30% ethyl acetate in heptane) afforded the product as an oil. Yield: 6.0 g, 21 mmol, 68%. $^1$H NMR (400 MHz, CDCl$_3$) δ 7.04 (dt, J=15.7, 7.4 Hz, 1H), 5.85-5.91 (m, 1H), 4.59 (dd, J=5.4, 5.2 Hz, 1H), 3.64-3.74 (m, 6H), 3.52-3.61 (m, 2H), 3.44 (dd, J=10.3, 5.5 Hz, 1H), 2.76 (dt, J=8.5, 5.9 Hz, 1H), 2.51 (ddd, J=7.3, 5.9, 1.4 Hz, 2H), 1.19-1.24 (m, 6H), 0.78-0.89 (m, 1H), 0.57-0.66 (m, 1H), 0.37-0.52 (m, 2H), 0.03-0.11 (m, 1H).

Step 2. Synthesis of methyl (2E)-5-cyclopropyl-5-{[2-(hydroxyimino)ethyl]oxy}pent-2-enoate (C35)

Methyl (2E)-5-cyclopropyl-5-(2,2-diethoxyethoxyl)pent-2-enoate (C34) was converted to the product using the method described for synthesis of 2-{[(2R)-1-(benzyloxy)pent-4-en-2-yl]oxy}-N-hydroxyethanimine (C3) in the section "Alternate conversion of C2 to C4." The product was obtained as an oil: $^1$H NMR analysis indicated a roughly 1:1 mixture of geometric isomers around the oxime. Yield: 3.50 g, 15.4 mmol, 73%. $^1$H NMR (400 MHz, CDCl$_3$) δ 7.73 and 7.47 (2 br s, total 1H), [7.49 (dd, J=5.8, 5.6 Hz) and 6.90 (dd, J=3.7, 3.6 Hz), total 1H], 6.99-7.09 (m, 1H), 5.87-5.93 (m, 1H), [4.54 (dd, half of ABX pattern, J=16.1, 3.6 Hz), 4.37 (dd, half of ABX pattern, J=16.0, 3.7 Hz), 4.28 (dd, half of ABX pattern, J=12.8, 5.5 Hz) and 4.14 (dd, half of ABX pattern, J=12.7, 5.8 Hz), total 2H], 3.74 and 3.74 (2 s, total 3H), 2.71-2.81 (m, 1H), 2.51-2.57 (m, 2H), 0.80-0.90 (m, 1H), 0.63-0.72 (m, 1H), 0.48-0.57 (m, 1H), 0.38-0.47 (m, 1H), 0.06-0.13 (m, 1H).

Step 3. Synthesis of methyl rel-(3R,3aR,5R)-5-cyclopropyl-3,3a,4,5-tetrahydro-7H-pyrano[3,4-c][1,2]oxazole-3-carboxylate (C36)

Methyl (2E)-5-cyclopropyl-5-{[2-(hydroxyimino)ethyl]oxy}pent-2-enoate (C35) was converted to the product using the method described for synthesis of rel-(3aR,5R)-5-cyclopropyl-3,3a,4,5-tetrahydro-7H-pyrano[3,4-c][1,2]oxazole (C18) in Example 2. The product was obtained as a solid; the indicated relative stereochemistry was assigned by analogy with C27 in Example 3. Yield: 3.30 g, 14.7 mmol, 95%. $^1$H NMR (400 MHz, CDCl₃) δ 4.70 (br d, J=13.3 Hz, 1H), 4.61 (d, J=10.2 Hz, 1H), 4.13 (dd, J=13.3, 1.2 Hz, 1H), 3.83 (s, 3H), 3.55-3.64 (m, 1H), 2.84 (ddd, J=11.0, 7.9, 1.9 Hz, 1H), 2.39 (ddd, J=12.9, 6.6, 1.7 Hz, 1H), 1.75 (ddd, J=12.9, 11.5, 11.3 Hz, 1H), 0.89-0.98 (m, 1H), 0.51-0.64 (m, 2H), 0.38-0.45 (m, 1H), 0.22-0.29 (m, 1H).

Step 4. Synthesis of rel-[(3R,3aR,5R)-5-cyclopropyl-3,3a,4,5-tetrahydro-7H-pyrano[3,4-c][1,2]oxazol-3-yl]methanol (C37)

A solution of methyl rel-(3R,3aR,5R)-5-cyclopropyl-3,3a,4,5-tetrahydro-7H-pyrano[3,4-c][1,2]oxazole-3-carboxylate (C36) (3.30 g, 14.6 mmol) in ethanol (30 mL) and tetrahydrofuran (29 mL) was cooled to 0° C. and treated with sodium borohydride (831 mg, 22.0 mmol). The reaction mixture was allowed to warm to room temperature and stir for 20 minutes at that temperature, then was poured into saturated aqueous ammonium chloride solution. The mixture was extracted with ethyl acetate, and the combined organic layers were washed with saturated aqueous sodium chloride solution, dried over sodium sulfate, filtered, and concentrated in vacuo. Chromatographic purification on silica gel (Eluent: 60% ethyl acetate in heptane) afforded the product as an oil. Yield: 1.95 g, 9.89 mmol, 68%. LCMS m/z 198.1 [M+H⁺]. ¹H NMR (400 MHz, CDCl₃) δ 4.67 (br d, J=13.3 Hz, 1H), 4.24-4.31 (m, 1H), 4.13 (d, J=13.3 Hz, 1H), 3.96-4.04 (m, 1H), 3.72 (ddd, J=12.3, 8.8, 3.5 Hz, 1H), 3.38 (ddd, J=10.9, 10.9, 6.6 Hz, 1H), 2.79-2.87 (m, 1H), 2.25 (dd, J=12.9, 6.6 Hz, 1H), 1.80-1.95 (m, 1H), 1.63-1.74 (m, 1H), 0.88-0.99 (m, 1H), 0.50-0.68 (m, 2H), 0.38-0.46 (m, 1H), 0.21-0.29 (m, 1H).

Step 5. Synthesis of rel-(3R,3aR,5R)-5-cyclopropyl-3-(methoxymethyl)-3,3a,4,5-tetrahydro-7H-pyrano[3,4-c][1,2]oxazole (C38)

Sodium hydride (60% in oil, 395 mg, 9.88 mmol) was slurried in N,N-dimethylformamide (30 mL) and cooled in an ice bath. A solution of rel-[(3R,3aR,5R)-5-cyclopropyl-3,3a,4,5-tetrahydro-7H-pyrano[3,4-c][1,2]oxazol-3-yl]methanol (C37) (1.30 g, 6.59 mmol) in minimal N,N-dimethylformamide was added drop-wise, and the reaction mixture was stirred at 0° C. for 30 minutes. Iodomethane (0.45 mL, 7.2 mmol) was then added in a drop-wise manner, and the reaction was allowed to proceed for an additional 30 minutes at 0° C. Water was added, and the mixture was warmed to room temperature and extracted twice with ethyl acetate. The combined organic layers were washed with saturated aqueous sodium chloride solution, dried over sodium sulfate, filtered, and concentrated in vacuo. Chromatography on silica gel (Gradient: 0% to 60% ethyl acetate in heptane) provided the product as an oil. Yield: 1.0 g, 4.7 mmol, 71%. LCMS m/z 212.1 [M+H⁺].

Step 6. Synthesis of rel-(3R,3aR,5R,7aS)-5-cyclopropyl-7a-(2,4-difluorophenyl)-3-(methoxymethyl)hexahydro-1H-pyrano[3,4-c][1,2]oxazole (C39)

rel-(3R,3aR,5R)-5-Cyclopropyl-3-(methoxymethyl)-3,3a,4,5-tetrahydro-7H-pyrano[3,4-c][1,2]oxazole (C38) was converted to the product using the method described for synthesis of rel-(3aR,5R,7aS)-5-cyclopropyl-7a-(2,4-difluorophenyl)hexahydro-1H-pyrano[3,4-c][1,2]oxazole (C19) in Example 2. The product was obtained as an oil. Yield: 0.85 g, 2.6 mmol, 55%. LCMS m/z 326.2 [M+H⁺].

Step 7. Synthesis of rel-(1R)-1-[(2R,4R,5S)-5-amino-2-cyclopropyl-5-(2,4-difluorophenyl)tetrahydro-2H-pyran-4-yl]-2-methoxyethanol (C40)

Zinc powder (2.22 g, 34.0 mmol) was added to a solution of rel-(3R,3aR,5R,7aS)-5-cyclopropyl-7a-(2,4-difluorophenyl)-3-(methoxymethyl)hexahydro-1H-pyrano[3,4-c][1,2]oxazole (C39) (850 mg, 2.61 mmol) in acetic acid (9 mL), and the resulting mixture was allowed to cool to room temperature and stir for 5 hours. The mixture was filtered through Celite, and the filtrate was concentrated in vacuo to afford the product as an oil. Yield: 845 mg, 2.58 mmol, 99%. LCMS m/z 328.2 [M+H⁺].

Step 8. Synthesis of rel-N-({(3S,4R,6R)-6-cyclopropyl-3-(2,4-difluorophenyl)-4-[(1R)-1-hydroxy-2-methoxyethyl]tetrahydro-2H-pyran-3-yl}carbamothioyl)benzamide (C41)

Conversion of rel-(1R)-1-[(2R,4R,5S)-5-amino-2-cyclopropyl-5-(2,4-difluorophenyl)tetrahydro-2H-pyran-4-yl]-2-methoxyethanol (C40) to the product was carried out via the method described for synthesis of N-{[(3S,4R,6R)-6-[(benzyloxy)methyl]-3-(2,4-difluorophenyl)-4-(hydroxymethyl)tetrahydro-2H-pyran-3-yl]carbamothioyl}benzamide (C7) in Preparation P1. In this case, purification was effected via silica gel chromatography (Gradient: 0% to 60% ethyl acetate in heptane), affording the product as a solid. Yield: 0.55 g, 1.1 mmol, 43%.

Step 9. Synthesis of rel-N-[(4S,4aR,6R,8aS)-6-cyclopropyl-8a-(2,4-difluorophenyl)-4-(methoxymethyl)-4,4a,5,6,8,8a-hexahydropyrano[3,4-d][1,3]thiazin-2-yl]benzamide (C42)

rel-N-({(3S,4R,6R)-6-Cyclopropyl-3-(2,4-difluorophenyl)-4-[(1R)-1-hydroxy-2-methoxyethyl]tetrahydro-2H-pyran-3-yl}carbamothioyl)benzamide (C41) was converted to the product using the method described for synthesis of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8) in Preparation P1, except that the reaction was warmed to room temperature and allowed to proceed for 18 hours before work-up. The product was obtained as a solid. Yield: 17 mg, 36 μmol, 51%. LCMS m/z 473.3 [M+H⁺]. ¹H NMR (400 MHz, CDCl₃), characteristic peaks: δ 8.24 (br d, J=7 Hz, 2H), 7.49-7.54 (m, 1H), 7.36-7.48 (m, 3H), 6.83-6.95 (m, 2H), 4.09 (br d, J=12 Hz, 1H), 3.82 (d, J=12.1 Hz, 1H), 3.62-3.69 (m, 1H), 3.37-3.45 (m, 2H), 3.34 (s, 3H), 3.09-3.16 (m, 1H), 2.94 (ddd, J=10.9, 8.2, 2.3 Hz, 1H), 1.80-1.92 (m, 1H), 1.68-1.76 (m, 1H), 0.50-0.61 (m, 2H), 0.40-0.47 (m, 1H), 0.24-0.31 (m, 1H).

Step 10. Synthesis of rel-(4S,4aR,6R,8aS)-6-cyclopropyl-8a-(2,4-difluorophenyl)-4-(methoxymethyl)-4,4a,5,6,8,8a-hexahydropyrano[3,4-d][1,3]thiazin-2-amine, hydrochloride salt (5)

Conversion of rel-N-[(4S,4aR,6R,8aS)-6-cyclopropyl-8a-(2,4-difluorophenyl)-4-(methoxymethyl)-4,4a,5,6,8,8a-hexahydropyrano[3,4-d][1,3]thiazin-2-yl]benzamide (C42) to the free base of the product was carried out via the method described for synthesis of (4aR,6R,8aS)-8a-(2,4-difluorophenyl)-6-(oxetan-2-yl)-4,4a,5,6,8,8a-hexahydropyrano[3,4-d][1,3]thiazin-2-amine (4) in Example 4. In this case, purification was effected using silica gel chromatography (Gradient: 0% to 15% methanol in dichloromethane), affording an oil. This was dissolved in dichloromethane and treated with a 1 M solution of hydrogen chloride in diethyl ether; removal of volatiles under reduced pressure provided the product as a solid. Yield: 8.6 mg, 21 μmol, 58%. LCMS m/z 369.2 [M+H⁺]. ¹H NMR, free base of 5: (400 MHz, CDCl₃) δ 7.33 (ddd, J=9.0, 9.0, 6.6 Hz, 1H), 6.74-6.87 (m, 2H), 4.03 (dd, J=10.9, 2.3 Hz, 1H), 3.80 (d, J=11.3 Hz, 1H), 3.58-3.65 (m, 1H), 3.32-3.39 (m, 2H), 3.30 (s, 3H), 2.79-2.87 (m, 2H), 1.63-1.74 (m, 1H), 1.50-1.57 (m, 1H), 0.91-1.04 (m, 1H), 0.47-0.61 (m, 2H), 0.38-0.46 (m, 1H), 0.19-0.27 (m, 1H).

Example 6

(4S,4aR,6R,8aS)-6-Cyclopropyl-8a-(2,4-difluorophenyl)-4-(fluoromethyl)-4,4a,5,6,8,8a-hexahydropyrano[3,4-d][1,3]thiazin-2-amine, hydrochloride salt (6)

Step 1. Synthesis of rel-(3R,3aR,5R)-5-cyclopropyl-3-(fluoromethyl)-3,3a,4,5-tetrahydro-7H-pyrano[3,4-c][1,2]oxazole (C43)

N-(Difluoro-λ⁴-sulfanylidene)-N-ethylethanaminium tetrafluoroborate (XtalFluor-E, 766 mg, 3.35 mmol) was added to a solution of triethylamine trihydrofluoride (727 μL, 4.46 mmol) in dichloromethane (11 mL). rel-[(3R,3aR,5R)-5-Cyclopropyl-3,3a,4,5-tetrahydro-7H-pyrano[3,4-c][1,2]oxazol-3-yl]methanol (C37) (440 mg, 2.23 mmol) was added, and the reaction mixture was stirred for 2 hours at room temperature. Aqueous sodium bicarbonate solution was added, and the mixture was stirred for 15 minutes, then extracted twice with dichloromethane. The combined organic layers were dried over sodium sulfate, filtered, and concentrated in vacuo. Purification via silica gel chromatography (Gradient: 0% to 50% ethyl acetate in heptane) afforded the product as an oil. Yield: 180 mg, 0.904 mmol, 41%. ¹H NMR

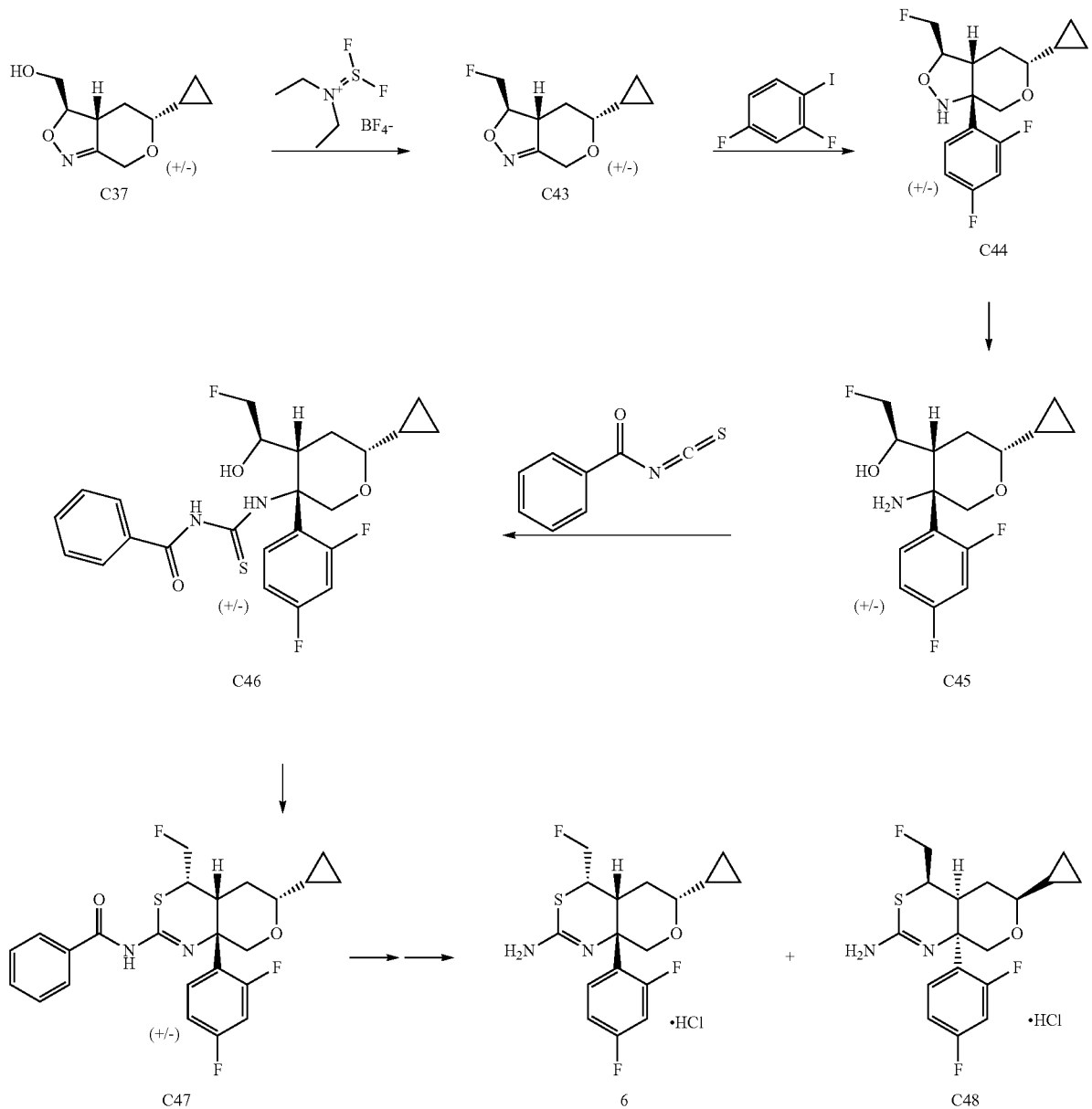

(400 MHz, CDCl₃) δ 4.63 (ddd, half of ABX pattern, J=47.4, 10.4, 3.5 Hz, 1H), 4.62 (br d, J=13.3 Hz, 1H), 4.54 (ddd, half of ABX pattern, J=46.7, 10.3, 4.2 Hz, 1H), 4.32 (dddd, J=20.2, 10.3, 3.9, 3.8 Hz, 1H), 4.10 (dd, J=13.4, 1.2 Hz, 1H), 3.28 (br ddd, J=11, 11, 6.5 Hz, 1H), 2.81 (ddd, J=11.0, 7.9, 1.9 Hz, 1H), 2.25 (ddd, J=12.8, 6.5, 1.7 Hz, 1H), 1.61-1.72 (m, 1H), 0.85-0.94 (m, 1H), 0.47-0.59 (m, 2H), 0.34-0.41 (m, 1H), 0.18-0.25 (m, 1H).

Step 2. Synthesis of rel-(3R,3aR,5R,7aS)-5-cyclopropyl-7a-(2,4-difluorophenyl)-3-(fluoromethyl)hexahydro-1H-pyrano[3,4-c][1,2]oxazole (C44)

Conversion of rel-(3R,3aR,5R)-5-cyclopropyl-3-(fluoromethyl)-3,3a,4,5-tetrahydro-7H-pyrano[3,4-c][1,2]oxazole (C43) to the product was carried out using the method described for synthesis of rel-(3aR,5R,7aS)-5-cyclopropyl-7a-(2,4-difluorophenyl)hexahydro-1H-pyrano[3,4-c][1,2]oxazole (C19) in Example 2. The product was obtained as an oil. Yield: 0.10 g, 0.32 mmol, 64%. ¹H NMR (400 MHz, CDCl₃) δ 7.93 (ddd, J=9, 9, 7 Hz, 1H), 6.90 (br ddd, J=9, 8, 2 Hz, 1H), 6.80 (ddd, J=12, 8.6, 2.5 Hz, 1H), 6.45 (s, 1H), 4.12-4.21 (m, 1H), 3.60-3.95 (m, 4H), 3.09 (br dd, J=9, 9 Hz, 1H), 2.88 (br dd, J=10, 9 Hz, 1H), 2.18 (br dd, J=14, 7.5 Hz, 1H), 1.63-1.75 (m, 1H), 0.88-0.98 (m, 1H), 0.52-0.64 (m, 2H), 0.37-0.46 (m, 1H), 0.24-0.33 (m, 1H).

Step 3. Synthesis of rel-(1R)-1-[(2R,4R,5S)-5-amino-2-cyclopropyl-5-(2,4-difluorophenyl)tetrahydro-2H-pyran-4-yl]-2-fluoroethanol (C45)

rel-(3R,3aR,5R,7aS)-5-Cyclopropyl-7a-(2,4-difluorophenyl)-3-(fluoromethyl)hexahydro-1H-pyrano[3,4-c][1,2]oxazole (C44) was converted to the product using the chemistry described for synthesis of [(2R,4R,5S)-5-amino-2-[(benzyloxy)methyl]-5-(2,4-difluorophenyl)tetrahydro-2H-pyran-4-yl]methanol (C6) in Preparation P1. The product was obtained as an oil. Yield: 0.17 g, 0.54 mmol, 99%. LCMS m/z 316.2 [M+H⁺].

Step 4. Synthesis of rel-N-({(3S,4R,6R)-6-cyclopropyl-3-(2,4-difluorophenyl)-4-[(1R)-2-fluoro-1-hydroxyethyl]tetrahydro-2H-pyran-3-yl}carbamothioyl)benzamide (C46)

Conversion of rel-(1R)-1-[(2R,4R,5S)-5-amino-2-cyclopropyl-5-(2,4-difluorophenyl)tetrahydro-2H-pyran-4-yl]-2-fluoroethanol (C45) to the product was carried out according to the method described for synthesis of N-({(3S,4R,6R)-6-cyclopropyl-3-(2,4-difluorophenyl)-4-[(1S)-1-hydroxyethyl]tetrahydro-2H-pyran-3-yl}carbamothioyl)benzamide (C30) in Example 3. The product was obtained as a solid. Yield: 155 mg, 0.324 mmol, 60%. LCMS m/z 479.2 [M+H⁺].

Step 5. Synthesis of rel-N-[(4S,4aR,6R,8aS)-6-cyclopropyl-8a-(2,4-difluorophenyl)-4-(fluoromethyl)-4,4a,5,6,8,8a-hexahydropyrano[3,4-d][1,3]thiazin-2-yl]benzamide (C47)

rel-N-({(3S,4R,6R)-6-Cyclopropyl-3-(2,4-difluorophenyl)-4-[(1R)-2-fluoro-1-hydroxyethyl]tetrahydro-2H-pyran-3-yl}carbamothioyl)benzamide (C46) was converted to the product using the chemistry described for synthesis of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8) in Preparation P1. The product was obtained as an oil. Yield: 36 mg, 78 μmol, 65%. LCMS m/z 461.2 [M+H⁺]. ¹H NMR (400 MHz, CDCl₃) δ 8.21 (br d, J=7.2 Hz, 2H), 7.50-7.56 (m, 1H), 7.43-7.49 (m, 2H), 7.39 (ddd, J=9.0, 9.0, 6.3 Hz, 1H), 6.86-6.96 (m, 2H), 4.61 (ddd, half of ABX pattern, J=46.9, 9.5, 7.8 Hz, 1H), 4.44 (ddd, half of ABX pattern, J=46.2, 9.5, 6.6 Hz, 1H), 4.10 (dd, J=12.1, 1.8 Hz, 1H), 3.82 (d, J=12.3 Hz, 1H), 3.47-3.56 (m, 1H), 3.16-3.23 (m, 1H), 2.94 (ddd, J=11.0, 8.0, 2.5 Hz, 1H), 1.81-1.93 (m, 1H), 1.75-1.81 (m, 1H), 0.95-1.04 (m, 1H), 0.51-0.62 (m, 2H), 0.40-0.47 (m, 1H), 0.24-0.31 (m, 1H).

Step 6. Synthesis of (4S,4aR,6R,8aS)-6-cyclopropyl-8a-(2,4-difluorophenyl)-4-(fluoromethyl)-4,4a,5,6,8,8a-hexahydropyrano[3,4-d][1,3]thiazin-2-amine, hydrochloride salt (6)

Hydrazine monohydrate (69 μL, 1.4 mmol) was added to a solution of rel-N-[(4S,4aR,6R,8aS)-6-cyclopropyl-8a-(2,4-difluorophenyl)-4-(fluoromethyl)-4,4a,5,6,8,8a-hexahydropyrano[3,4-d][1,3]thiazin-2-yl]benzamide (C47) (60 mg, 0.13 mmol) in ethanol (2.6 mL), and the reaction mixture was allowed to stir at room temperature for 1 hour. Volatiles were removed under reduced pressure, and the residue was purified via silica gel chromatography (Gradient: 0% to 10% methanol in dichloromethane), then separated into its enantiomers via supercritical fluid chromatography (Column: Chiral Technologies Chiralcel OJ-H, 5 μm; Eluent: 85:15 carbon dioxide/methanol containing 0.2% ammonia). The first-eluting enantiomer was the free base of compound 6. This material was dissolved in dichloromethane and treated with 1 M hydrogen chloride in diethyl ether; concentration in vacuo provided hydrochloride salt 6 as a solid. The indicated absolute stereochemistry was assigned on the basis of the biological activity of compound 6; its enantiomer C48 (below) proved inactive upon similar testing (see Table 3). Yield: 28 mg, assumed 65 μmol, 50%. Free base of 6: LCMS m/z 357.1 [M+H⁺]. ¹H NMR (400 MHz, CDCl₃) δ 7.33 (ddd, J=9.0, 9.0, 6.7 Hz, 1H), 6.86 (dddd, J=8.8, 7.7, 2.7, 0.8 Hz, 1H), 6.80 (ddd, J=12.4, 8.6, 2.6 Hz, 1H), 4.57 (ddd, J=46.8, 9.4, 7.1 Hz, 1H), 4.36 (ddd, J=46.6, 9.4, 6.9 Hz, 1H), 4.03 (dd, J=11.0, 2.5 Hz, 1H), 3.81 (br d, J=11.1 Hz, 1H), 3.42-3.51 (m, 1H), 2.93 (br ddd, J=12.0, 4.0, 4.0 Hz, 1H), 2.83 (ddd, J=11.0, 8.3, 2.5 Hz, 1H), 1.63-1.75 (m, 1H), 1.57 (ddd, J=13.1, 4.2, 2.7 Hz, 1H), 0.93-1.03 (m, 1H), 0.48-0.61 (m, 2H), 0.39-0.46 (m, 1H), 0.20-0.27 (m, 1H). Compound 6: ¹H NMR (600 MHz, DMSO-d₆) δ 7.92 (br s, 3H), 7.30-7.40 (m, 2H), 7.22-7.27 (m, 1H), 4.79 (ddd, J=46, 10, 5 Hz, 1H), 4.61-4.73 (m, 1H), 3.82-3.91 (m, 2H), 3.51-3.59 (m, 1H), 3.19-3.24 (m, 1H), 3.00-3.05 (m, 1H), 1.77-1.82 (m, 1H), 1.43-1.51 (m, 1H), 0.90-0.97 (m, 1H), 0.44-0.51 (m, 2H), 0.33-0.38 (m, 1H), 0.27-0.31 (m, 1H).

The second-eluting enantiomer was converted to its hydrochloride salt in the same manner, and the resulting solid was assigned as (4R,4aS,6S,8aR)-6-cyclopropyl-8a-(2,4-difluorophenyl)-4-(fluoromethyl)-4,4a,5,6,8,8a-hexahydropyrano[3,4-d][1,3]thiazin-2-amine, hydrochloride salt (C48). Yield: 29 mg, assumed 65 μmol, 50%. Free base of C48: ¹H NMR (400 MHz, CDCl₃) δ 7.33 (ddd, J=9.0, 9.0, 6.6 Hz, 1H), 6.83-6.89 (m, 1H), 6.80 (ddd, J=12.4, 8.6, 2.5 Hz, 1H), 4.57 (ddd, J=46.8, 9.4, 7.0 Hz, 1H), 4.36 (ddd, J=46.7, 9.4, 6.9 Hz, 1H), 4.03 (dd, J=11.0, 2.5 Hz, 1H), 3.81 (d, J=11.1 Hz, 1H), 3.42-3.51 (m, 1H), 2.92 (br ddd, J=12.0, 4, 4 Hz, 1H), 2.83 (ddd, J=11.1, 8.3, 2.5 Hz, 1H), 1.63-1.75 (m, 1H), 1.57 (ddd, J=13.2, 4.2, 2.6 Hz, 1H), 0.93-1.03 (m, 1H), 0.48-0.61 (m, 2H), 0.38-0.46 (m, 1H), 0.20-0.27 (m, 1H). Compound C48: ¹H NMR (600 MHz, DMSO-d₆) δ 7.93 (br s, 3H), 7.30-7.40 (m, 2H), 7.22-7.27 (m, 1H), 4.73-4.85 (m, 1H), 4.61-4.73 (m, 1H), 3.81-3.91 (m, 2H), 3.51-3.58 (m, 1H), 3.18-3.23 (m, 1H), 2.99-3.04 (m, 1H), 1.76-1.82 (m, 1H), 1.44-1.51 (m, 1H), 0.90-0.97 (m, 1H), 0.44-0.50 (m, 2H), 0.33-0.37 (m, 1H), 0.27-0.31 (m, 1H).

Example 7
(4aR,6R,8aS)-8a-(2,4-Difluorophenyl)-6-(1-methylcyclopropyl)-4,4a,5,6,8,8a-hexahydropyrano[3,4-d][1,3]thiazin-2-amine (7)
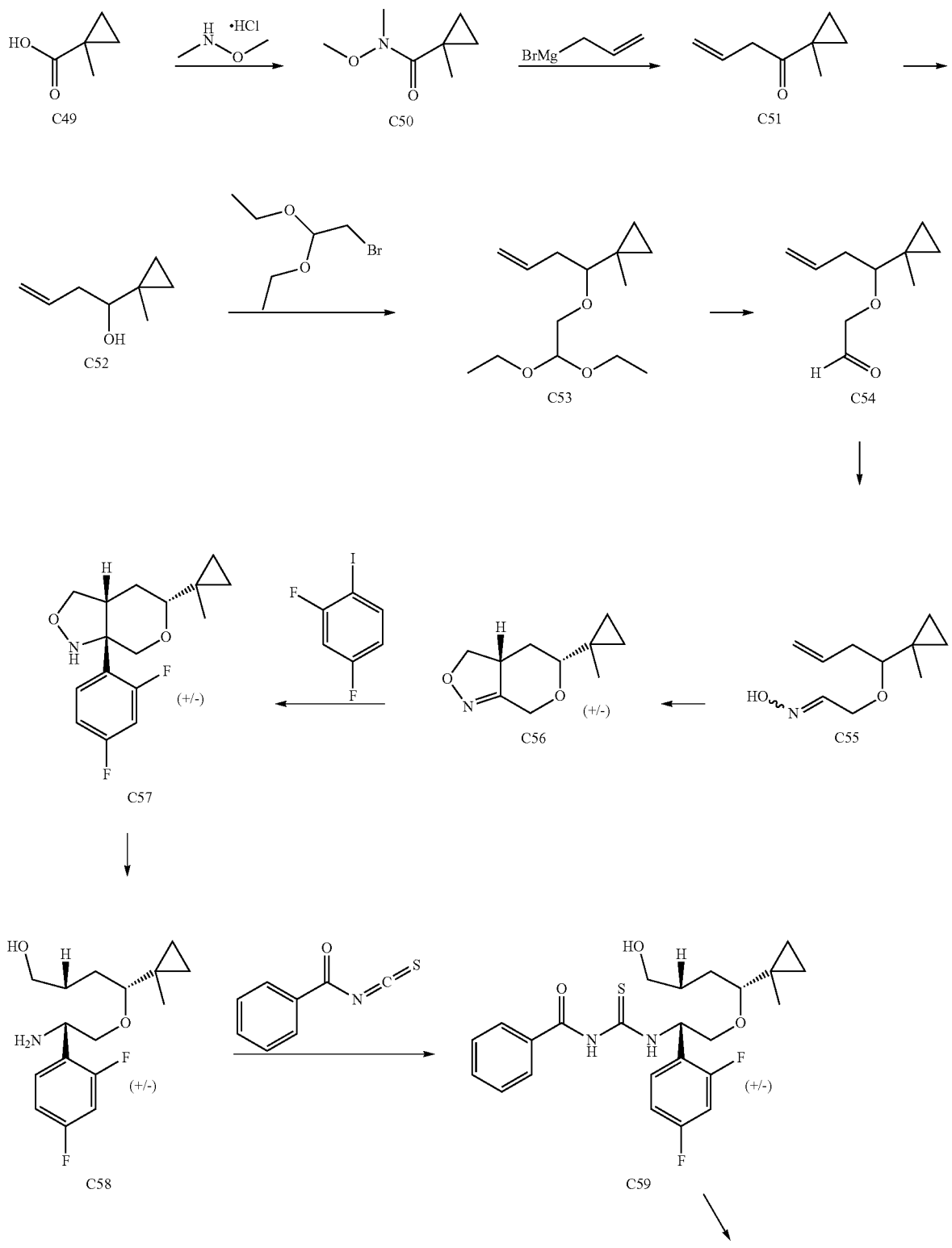

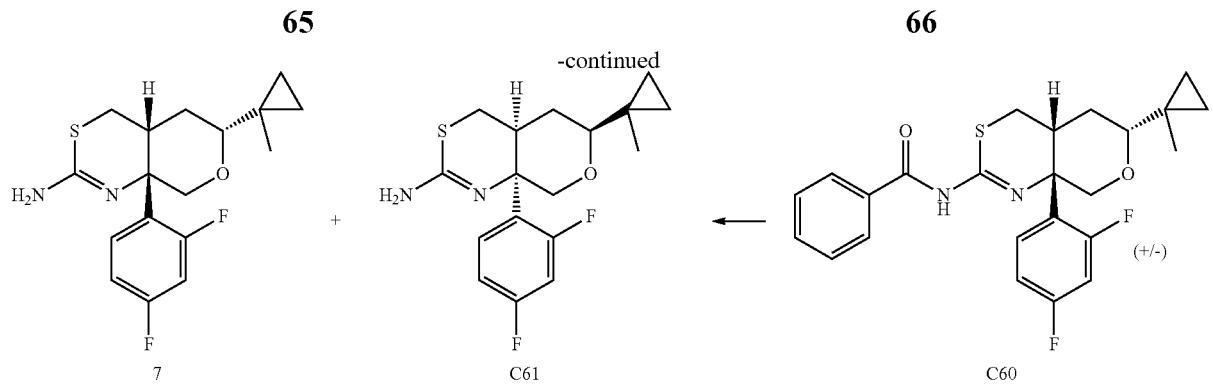

Step 1. Synthesis of N-methoxy-N,1-dimethylcyclopropanecarboxamide (C50)

To a solution of 1-methylcyclopropanecarboxylic acid (C49) (30 g, 300 mmol) in dichloromethane (500 mL) was added 1,1'-carbonyldiimidazole (51 g, 315 mmol) portion-wise, not allowing the temperature to exceed 25° C. The mixture was stirred at room temperature for 2 hours. N,O-Dimethylhydroxylamine hydrochloride (34.8 g, 357 mmol) was added in one portion and stirred at room temperature for 12 hours. The mixture was washed with water (2×200 mL) and saturated aqueous sodium chloride solution (100 mL), dried over sodium sulfate and concentrated to give crude product as a colorless oil, which was directly used in the next step. Yield: 49 g, 342 mmol, 114%. $^1$H NMR (400 MHz, CDCl$_3$) δ 3.69 (s, 3H), 3.20 (s, 3H), 1.34 (s, 3H), 1.01 (dd, J=6.4, 4.4 Hz, 2H), 0.53 (dd, J=6.4, 4.4 Hz, 2H).

Step 2. Synthesis of 1-(1-methylcyclopropyl)but-3-en-1-one (C51)

To a solution of N-methoxy-N,1-dimethylcyclopropanecarboxamide (C50) (18 g, 0.126 mol) in tetrahydrofuran (360 mL) was added a solution of allylmagnesium bromide (1.0 M in diethyl ether, 500 mL, 0.5 mol) drop-wise at −60° C. The mixture was stirred at −60° C. for 1 hour, then was quenched with saturated aqueous ammonium chloride solution (50 mL). The reaction was extracted with dichloromethane (2×500 mL), the organic layers were washed with saturated aqueous sodium chloride solution (200 mL), dried, and concentrated in vacuo to give the product as a yellow oil, which was used directly in the next step.

Step 3. Synthesis of 1-(1-methylcyclopropyl)but-3-en-1-ol (C52)

To a suspension of lithium aluminum hydride (7.17 g, 189 mmol) in tetrahydrofuran (200 mL) at −78° C. was added drop-wise a solution of 1-(1-methylcyclopropyl)but-3-en-1-one (C51) (15.6 g, 126 mmol) in tetrahydrofuran (100 mL). After the addition, the mixture was stirred at −78° C. for 0.5 hours. The reaction mixture was quenched with water (7 mL) at −78° C., then dichloromethane (100 mL) was added and the mixture was stirred at room temperature for 0.5 hours. The mixture was filtered, the filter cake was washed with dichloromethane (2×150 mL), and the combined filtrates were dried and concentrated in vacuo to give crude product; purification via silica gel chromatography (Gradient: 4% to 10% ethyl acetate in petroleum ether) afforded the product as a yellow oil. Yield: 12 g, 95 mmol, 76% over 2 steps. $^1$H NMR (400 MHz, CDCl$_3$) δ 5.68-5.90 (m, 1H), 5.07-5.17 (m, 2H), 2.92 (dd, J=13.2, 4.4 Hz, 1H), 2.25-2.40 (m, 2H), 1.06 (s, 3H), 0.38-0.45 (m, 2H), 0.30-0.36 (m, 2H).

Step 4. Synthesis of 1-[1-(2,2-diethoxyethoxyl)but-3-en-1-yl]-1-methylcyclopropane (C53)

A solution of 1-(1-methylcyclopropyl)but-3-en-1-ol (C52) (6.0 g, 47.6 mmol) in tetrahydrofuran (50 mL) was added to a 0° C. suspension of sodium hydride (60% in mineral oil, 7.7 g, 190.5 mmol) in tetrahydrofuran (200 mL). After stirring at room temperature for 10 minutes, 2-bromo-1,1-diethoxyethane (97%, 37.5 g, 190.5 mmol) was added drop-wise at room temperature. The reaction mixture was heated to 75° C. for 24 hours. It was then cooled to 0° C., slowly quenched with water (200 mL) and extracted with dichloromethane (3×500 mL). The combined organic layers were dried over sodium sulfate, filtered, and concentrated in vacuo; purification via silica gel chromatography (Gradient: 0% to 10% ethyl acetate in petroleum ether) afforded the product as a yellow oil.

Step 5. Synthesis of {[1-(1-methylcyclopropyl)but-3-en-1-yl]oxy}acetaldehyde (C54)

A mixture of 1-[1-(2,2-diethoxyethoxyl)but-3-en-1-yl]-1-methylcyclopropane (C53) (30%, 37.2 g, 154 mmol), aqueous hydrochloric acid (2 M, 116 mL, 232 mmol) and tetrahydrofuran (220 mL) was stirred at 55° C. for 1.5 hours. The reaction mixture was cooled to room temperature and concentrated to remove tetrahydrofuran. The aqueous phase was extracted with ethyl acetate (2×100 mL). The combined organic extracts were washed with saturated aqueous sodium chloride solution (3×50 mL), dried over sodium sulfate, filtered, and concentrated in vacuo (900 mbar, 60° C.) to afford the product as a colorless oil (27.7 g), which contained residual diethyl ether and tetrahydrofuran by $^1$H NMR analysis. This material was taken directly into the following step.

Step 6. Synthesis of N-hydroxy-2-{[1-(1-methylcyclopropyl)but-3-en-1-yl]oxy}ethanamine (C55)

{[1-(1-Methylcyclopropyl)but-3-en-1-yl]oxy}acetaldehyde (C54) (27.7 g from the previous step, ≤165 mmol) was dissolved in a 2:1 mixture of ethanol and water (39 mL). Sodium acetate (63.1 g, 770 mmol) was added; after the reaction mixture had been stirred for 15 minutes, hydroxylamine hydrochloride (98%, 32.1 g, 462 mmol) was added. The reaction mixture was heated to 60° C. for 24 hours. The reaction mixture was concentrated under reduced pressure to remove ethanol and extracted with dichloromethane (2×140 mL). The combined organic layers were dried over sodium sulfate, filtered, and concentrated in vacuo at 22° C. Silica gel chromatography (Gradient: 0% to 12% ethyl acetate in petroleum ether) provided the product as a colorless oil. By $^1$H NMR analysis, this material consisted of a roughly 1:1 mixture of E and Z oxime isomers. Yield: 4.1 g, 22.4 mmol, 48% over two steps. $^1$H NMR (400 MHz, CDCl$_3$) δ [7.49 (t, J=5.6 Hz) and 6.91 (t, J=3.6 Hz), total 1H], 5.82-5.92 (m, 1H), 5.00-5.10 (m, 2H), {[4.52 (dd, half of ABX pattern, J=16.4, 3.2 Hz) and 4.35 (dd, half of ABX pattern, J=16.4, 3.6 Hz)] and [4.27 (dd, half of ABX pattern, J=13.2, 5.6 Hz) and 4.09 (dd, half of ABX pattern, J=12.8, 6.0 Hz)], total 2H}, 2.59-2.64 (m, 1H), 2.25-2.45 (m, 2H), 1.02 (s, 3H), 0.42-0.56 (m, 2H), 0.18-0.29 (m, 2H).

Step 7. Synthesis of rel-(3aR,5R)-5-(1-methylcyclopropyl)-3,3a,4,5-tetrahydro-7H-pyrano[3,4-c][1,2] oxazole (C56)

An aqueous solution of sodium hypochlorite (6.15% solution, 65 mL, 51 mmol) was added drop-wise over 24 minutes to a solution of N-hydroxy-2-{[1-(1-methylcyclopropyl)but-3-en-1-yl]oxy}ethanimine (C55) (6.54 g, 36 mmol) and triethylamine (280 mg, 2.7 mmol) in dichloromethane (64 mL) that was immersed in a room temperature water bath. The rate of addition was adjusted to maintain the internal temperature of the reaction between 19.5° C. and 22.8° C. After completion of the addition, the reaction mixture was diluted with water (50 mL) and the aqueous layer was extracted with dichloromethane (3×50 mL). The combined organic layers were washed with saturated aqueous sodium chloride solution (50 mL), dried over sodium sulfate, filtered, and concentrated in vacuo (300 mbar, 40° C.). Silica gel chromatography (Gradient: 0% to 10% ethyl acetate in petroleum ether) provided the product as a white solid. Yield: 3.84 g, 21.2 mmol, 57%. The indicated relative stereochemistry of compound C56 was assigned based on nuclear Overhauser enhancement studies, which revealed an interaction between the methine protons on carbons 3a and 5. LCMS m/z 182 [M+H$^+$]. $^1$H NMR (400 MHz, CDCl$_3$) δ 4.73 (d, J=13.2 Hz, 1H), 4.64 (dd, J=10.4, 8.0 Hz, 1H), 4.14 (d, J=14.1 Hz, 1H), 3.81 (dd, J=11.6, 8.0 Hz, 1H), 3.44-3.39 (m, 1H), 2.82 (d, J=12.8 Hz, 1H), 2.21-2.15 (m, 1H), 1.76 (q, J=11.9 Hz, 1H), 1.05 (s, 3H), 0.55-0.51 (m, 1H), 0.44-0.41 (m, 2H), 0.40-0.39 (m, 1H).

Step 8. Synthesis of rel-(3aR,5R,7aS)-7a-(2,4-difluorophenyl)-5-(1-methylcyclopropyl)hexahydro-1H-pyrano[3,4-c][1,2]oxazole (C57)

Boron trifluoride diethyl etherate (7.86 g, 25.9 mmol) was added drop-wise to a solution of rel-(3aR,5R)-5-(1-methylcyclopropyl)-3,3a,4,5-tetrahydro-7H-pyrano[3,4-c][1,2]oxazole (C56) (4.255 g, 23.5 mmol) in toluene (500 mL) at an internal temperature of −72.5° C. The reaction mixture was stirred at −73° C. to −76° C. for 30 minutes, then treated with 2,4-difluoro-1-iodobenzene (98%, 6.22 g, 25.9 mmol) in one portion. While the reaction temperature was maintained below −73° C., n-butyllithium (2.5 M in hexanes, 9.9 mL, 24.8 mmol) was added in a drop-wise manner over 15 minutes. The reaction mixture was stirred at −73° C. to −75° C. for 1.5 hours, then was quenched with saturated aqueous ammonium chloride solution (350 mL) at −74° C. and allowed to warm to room temperature. The resulting mixture was extracted with ethyl acetate (400 mL), and the aqueous layer was extracted with additional ethyl acetate (250 mL and 100 mL); the combined organic layers were dried over sodium sulfate, filtered, and concentrated in vacuo. Chromatography on silica gel (Gradient: 0% to 10% ethyl acetate in petroleum ether) afforded the product as a white solid. Yield: 3.2 g, 10.8 mmol, 46%. LCMS m/z 296 [M+H$^+$]. $^1$H NMR (400 MHz, CDCl$_3$) δ 7.92 (q, J=8.3 Hz, 1H), 6.88 (dt, J=8.4, 2.4 Hz, 1H), 6.78 (ddd, J=11.6, 8.8, 2.4 Hz, 1H), 6.28 (br s, 1H), 4.04 (dd, J=12.4, 1.6 Hz, 1H), 3.82 (d, J=12.8 Hz, 1H), 3.72 (d, J=6.8 Hz, 1H), 3.53 (dd, J=6.8, 4.8 Hz, 1H), 3.01-3.06 (m, 1H), 2.95 (d, J=12.0 Hz, 1H), 1.83 (dd, J=13.2, 6.0 Hz, 1H), 1.62 (q, J=12.4 Hz, 1H), 1.09 (s, 3H), 0.52-0.56 (m, 1H), 0.43-0.48 (m, 1H), 0.36-0.41 (m, 1H), 0.28-0.33 (m, 1H).

Step 9. Synthesis of rel-[(2R,4R,5S)-5-amino-5-(2,4-difluorophenyl)-2-(1-methylcyclopropyl)tetrahydro-2H-pyran-4-yl]methanol (C58)

rel-(3aR,5R,7aS)-7a-(2,4-Difluorophenyl)-5-(1-methylcyclopropyl)hexahydro-1H-pyrano[3,4-c][1,2]oxazole (C57) (1.48 g, 5.00 mmol) was converted to the product according to the method described for the synthesis of [(2R,4R,5S)-5-amino-2-[(benzyloxy)methyl]-5-(2,4-difluorophenyl)tetrahydro-2H-pyran-4-yl]methanol (C6) in Preparation P1. The product was obtained as a dark oil (2.2 g), which was taken directly to the following step without additional purification.

Step 10. Synthesis of rel-N-{[(3S,4R,6R)-3-(2,4-difluorophenyl)-4-(hydroxymethyl)-6-(1-methylcyclopropyl)tetrahydro-2H-pyran-3-yl]carbamothioyl}benzamide (C59)

Benzoyl isothiocyanate (0.98 g, 6.00 mmol) was added drop-wise to a solution of rel-[(2R,4R,5S)-5-amino-5-(2,4-difluorophenyl)-2-(1-methylcyclopropyl)tetrahydro-2H-pyran-4-yl]methanol (C58) (2.20 g, 5.00 mmol) in dichloromethane (60 mL). After the reaction mixture had stirred at room temperature for 15 hours, it was partitioned between aqueous hydrochloric acid (0.1 M, 20 mL) and dichloromethane (35 mL). The organic layer was washed with saturated aqueous sodium bicarbonate solution (25 mL) and with saturated aqueous sodium chloride solution (25 mL), then dried over sodium sulfate, filtered, and concentrated in vacuo. Purification via silica gel chromatography (Gradient: 0% to 15% ethyl acetate in petroleum ether) provided the product as a brown solid. Yield: 1.1 g, 2.39 mmol, 48%.

Step 11. Synthesis of rel-N-[(4aR,6R,8aS)-8a-(2,4-difluorophenyl)-6-(1-methylcyclopropyl)-4,4a,5,6,8,8a-hexahydropyrano[3,4-d][1,3]thiazin-2-yl]benzamide (C60)

rel-N-{[(3S,4R,6R)-3-(2,4-Difluorophenyl)-4-(hydroxymethyl)-6-(1-methylcyclopropyl)tetrahydro-2H-pyran-3-yl]carbamothioyl}benzamide (C59) was converted to the product using the method described for synthesis of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8) in Preparation P1. The product was obtained as a white solid. Yield: 1.1 g, 16.8 mmol. LCMS m/z 443 [M+H$^+$].

Step 12. Synthesis of (4aR,6R,8aS)-8a-(2,4-difluorophenyl)-6-(1-methylcyclopropyl)-4,4a,5,6,8,8a-hexahydropyrano[3,4-d][1,3]thiazin-2-amine (7)

rel-N-[(4aR,6R,8aS)-8a-(2,4-Difluorophenyl)-6-(1-methylcyclopropyl)-4,4a,5,6,8,8a-hexahydropyrano[3,4-d][1,3]thiazin-2-yl]benzamide (C60) (1.1 g, 2.4 mmol) was combined with ethanol (60 mL) and hydrazine (50% in water, 1.1 g, 16.8 mmol) and stirred at room temperature for 20 hours. The reaction mixture was concentrated in vacuo and purified by recrystallization from methanol to provide the racemic product, which was separated into its enantiomers using supercritical fluid chromatography (Column: Chiralcel OD-H, 5 μm; Eluent: 9:1 carbon dioxide/methanol). The first-eluting enantiomer provided the product as a pale yellow solid. The indicated absolute stereochemistry was assigned to compound 7 on the basis of this compound's biological activity; its enantiomer C61 (below) proved essentially inactive (see Table 3). Yield: 230 mg, 0.678 mmol, 28%. LCMS m/z 339 [M+H$^+$]. $^1$H NMR (400 MHz, CD$_3$OD) δ 7.30-7.36 (m, 1H), 6.91-6.97 (m, 2H), 4.02 (dd, J=10.9, 2.3 Hz, 1H), 3.67 (d, J=11.3 Hz, 1H), 3.02 (dd, J=11.5, 2.1 Hz, 1H), 2.82-2.88 (m, 2H), 2.64-2.68 (m, 1H), 1.88-1.98 (m, 1H), 1.49-1.54 (m, 1H), 1.06 (s, 3H), 0.46-0.54 (m, 2H), 0.29-0.33 (m, 1H), 0.22-0.26 (m, 1H).

The second-eluting enantiomer, also obtained as a pale yellow solid, was assigned as (4aS,6S,8aR)-8a-(2,4-difluorophenyl)-6-(1-methylcyclopropyl)-4,4a,5,6,8,8a-hexahydropyrano[3,4-d][1,3]thiazin-2-amine (C61). Yield: 230 mg, 0.678 mmol, 28%. LCMS m/z 339 [M+H$^+$]. $^1$H NMR (400 MHz, CD$_3$OD) δ 7.31-7.37 (m, 1H), 6.93-6.98 (m, 2H), 4.02 (dd, J=10.9, 2.3 Hz, 1H), 3.68 (d, J=10.9 Hz, 1H), 3.03 (dd, J=11.7, 2.3 Hz, 1H), 2.83-2.89 (m, 2H), 2.67 (dd, J=12.3, 3.7 Hz, 1H), 1.89-1.99 (m, 1H), 1.50-1.55 (m, 1H), 1.07 (s, 3H), 0.47-0.57 (m, 2H), 0.29-0.34 (m, 1H), 0.23-0.27 (m, 1H).

Example 8

(4aR,6S,8aS)-6-(Cyclopropylmethyl)-8a-(2,4-difluorophenyl)-4,4a,5,6,8,8a-hexahydropyrano[3,4-d][1,3]thiazin-2-amine (8)

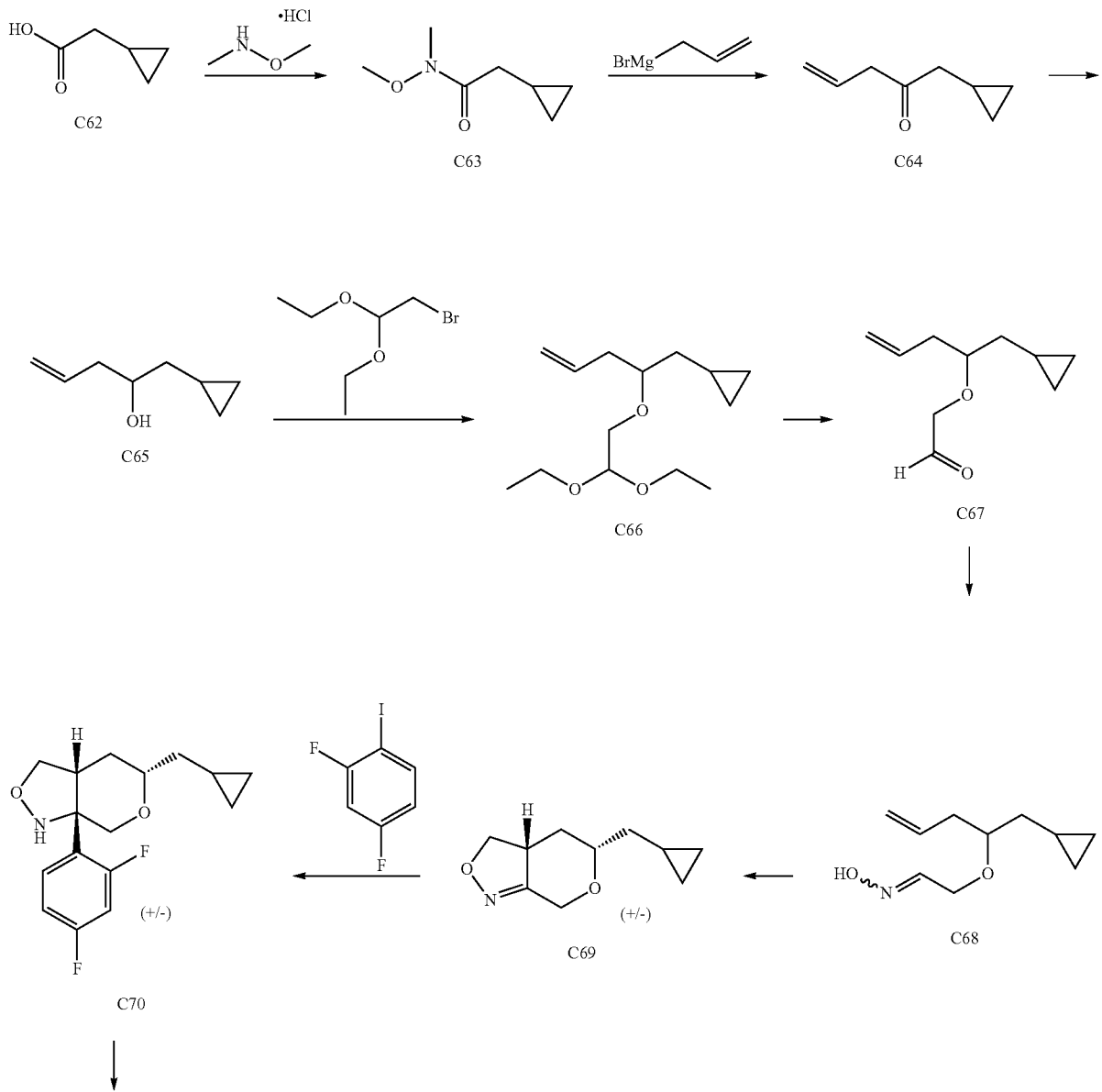

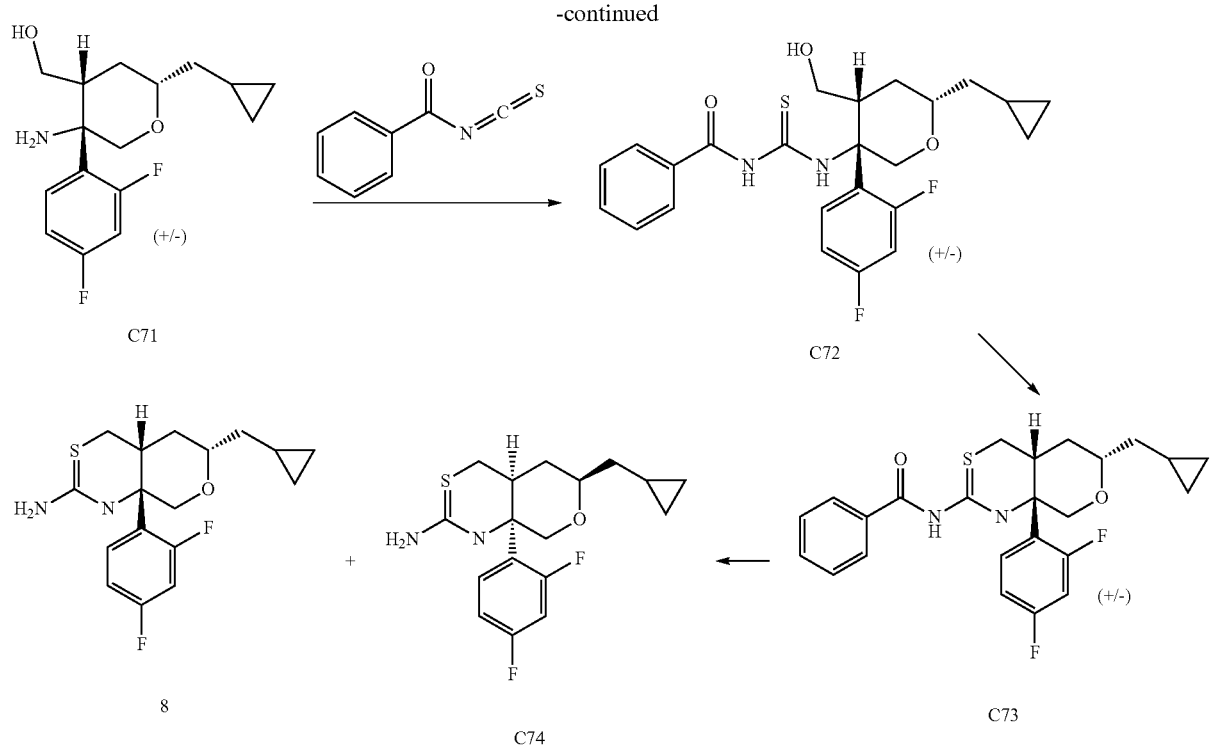

Step 1. Synthesis of 2-cyclopropyl-N-methoxy-N-methylacetamide (C63)

To a solution of 2-cyclopropylacetic acid (C62) (30 g, 300 mmol) in dichloromethane (800 mL) was added 1,1'-carbonyldiimidazole (54 g, 333 mmol) portion-wise, not allowing the temperature to exceed 25° C. The mixture was stirred at room temperature for 2 hours. N,O-Dimethylhydroxylamine hydrochloride (30 g, 308 mmol) was added in one portion and stirred at room temperature for 18 hours. The mixture was washed with water (2×200 mL) and saturated aqueous sodium chloride solution (100 mL), dried over sodium sulfate and concentrated to give crude product as a yellow oil, which was directly used in the next step. Yield: 48 g, 336 mmol, 112%. $^1$H NMR (400 MHz, CDCl$_3$) δ 3.62 (s, 3H), 3.12 (s, 3H), 2.30 (d, J=7.2 Hz, 2H), 1.03-1.06 (m, 1H), 0.48-0.52 (m, 2H), 0.11-0.13 (m, 2H).

Step 2. Synthesis of 1-cyclopropylpent-4-en-2-one (C64)

To a solution of 2-cyclopropyl-N-methoxy-N-methylacetamide (C63) (48 g, 0.3 mol) in tetrahydrofuran (900 mL) was added a solution of allylmagnesium bromide (1.0 M in diethyl ether, 1.5 L, 1.5 mol) drop-wise at −60° C. The mixture was stirred at −60° C. for 1 hour, then was quenched with saturated aqueous ammonium chloride solution (120 mL). The reaction was extracted with dichloromethane (2×500 mL), and the organic layers were washed with saturated aqueous sodium chloride solution (500 mL), dried and concentrated in vacuo to give the product as a yellow oil, which was used directly in the following step.

Step 3. Synthesis of 1-cyclopropylpent-4-en-2-ol (C65)

To a suspension of lithium aluminium hydride (17.1, 0.45 mol) in tetrahydrofuran (700 mL) at −78° C. was added drop-wise a solution of 1-cyclopropylpent-4-en-2-one (C64) (38 g, 0.3 mol) in tetrahydrofuran (100 mL). After the addition, the mixture was stirred at −78° C. for 1 hour. The reaction mixture was quenched with water (20 mL) at −78° C., then dichloromethane (200 mL) was added and the mixture was stirred at room temperature for 0.5 hours. The mixture was filtered, the filter cake was washed with dichloromethane (2×200 mL), and the combined filtrates were dried and concentrated in vacuo to give crude product; purification via silica gel chromatography (Gradient: 0% to 10% ethyl acetate in petroleum ether) afforded the product as a yellow oil. Yield: 16 g, 127 mmol, 43% over 2 steps. $^1$H NMR (400 MHz, CDCl$_3$) δ 5.81-5.87 (m, 1H), 5.01-5.14 (m, 2H), 3.75 (m, 1H), 2.30-2.34 (m, 1H), 2.18-2.23 (m, 1H), 1.34-1.43 (m, 2H), 0.68-0.80 (m, 1H), 0.39-0.49 (m, 2H), 0.02-0.15 (m, 2H).

Step 4. Synthesis of [2-(2,2-diethoxyethoxy)pent-4-en-1-yl]cyclopropane (C66)

A solution of 1-cyclopropylpent-4-en-2-ol (C65) (16 g, 0.127 mmol) in tetrahydrofuran (200 mL) was added to a 0° C. suspension of sodium hydride (60% in mineral oil, 15.2 g, 0.38 mol) in tetrahydrofuran (400 mL). After stirring at room temperature for 10 minutes, 2-bromo-1,1-diethoxyethane (97%, 75 g, 0.38 mol) was added drop-wise at room temperature. The reaction mixture was heated to 70° C. for 24 hours. It was then cooled to 0° C., slowly quenched with water (200 mL) and extracted with dichloromethane (3×500 mL). The combined organic layers were dried over sodium sulfate, filtered, and concentrated in vacuo; purification via silica gel chromatography (Gradient: 0% to 10% ethyl acetate in petroleum ether) afforded the product as a yellow oil. Yield: 20 g, 83 mmol, 65%. $^1$H NMR (400 MHz, CDCl$_3$) δ 5.79-5.89 (m, 1H), 5.04 (dt, J=14.0, 1.6 Hz, 2H), 4.60 (t, J=5.2 Hz, 1H), 3.64-3.73 (m, 2H), 3.51-3.62 (m, 4H), 3.45 (quintet, J=6.0

Hz, 1H), 2.31 (t, J=6.4 Hz, 1H), 1.50 (quintet, J=6.8 Hz, 1H), 1.20-1.30 (m, 2H), 1.21 (dt, J=6.8, 1.2 Hz, 6H), 0.72-0.80 (m, 1H), 0.38-0.49 (m, 2H), −0.02-0.10 (m, 2H).

Step 5. Synthesis of [(1-cyclopropylpent-4-en-2-yl)oxy]acetaldehyde (C67)

A mixture of [2-(2,2-diethoxyethoxy)pent-4-en-1-yl]cyclopropane (C66) (20 g, 83 mmol), aqueous hydrochloric acid (2 M, 83 mL, 166 mmol) and tetrahydrofuran (250 mL) was stirred at reflux for 1 hour. The reaction mixture was cooled to room temperature and concentrated to remove tetrahydrofuran. The aqueous phase was extracted with ethyl acetate (2×100 mL). The combined organic extracts were washed with saturated aqueous sodium chloride solution (3×50 mL), dried over sodium sulfate, filtered, and concentrated in vacuo to afford the product as a colorless oil (17 g). This material was taken directly into the following step.

Step 6. Synthesis of (1E)-2-[(1-cyclopropylpent-4-en-2-yl)oxy]-N-hydroxyethanimine (C68)

[(1-Cyclopropylpent-4-en-2-yl)oxy]acetaldehyde (C67) (17 g from the previous step, ≤83 mmol) was dissolved in a 2:1 mixture of ethanol and water (450 mL). Sodium acetate (41 g, 500 mmol) was added; after the reaction mixture had been stirred for 15 minutes, hydroxylamine hydrochloride (98%, 21 g, 300 mmol) was added. The reaction mixture was heated to 60° C. for 24 hours. The reaction mixture was concentrated under reduced pressure to remove ethanol and extracted with dichloromethane (3×140 mL). The combined organic layers were dried over sodium sulfate, filtered, and concentrated in vacuo at 22° C. Silica gel chromatography (Gradient: 0% to 20% ethyl acetate in petroleum ether) provided the product as a colorless oil. By $^1$H NMR analysis, this material consisted of a roughly 1:1 mixture of E and Z oxime isomers. Yield: 10 g, 55 mmol, 49.6% over two steps.

Step 7. Synthesis of rel-(3aR,5S)-5-(cyclopropylmethyl)-3,3a,4,5-tetrahydro-7H-pyrano[3,4-c][1,2]oxazole (C69)

An aqueous solution of sodium hypochlorite (6.15% solution, 100 mL, 78.6 mmol) was added drop-wise to a solution of (1E)-2-[(1-cyclopropylpent-4-en-2-yl)oxy]-N-hydroxyethanimine (C68) (10 g, 55 mmol) and triethylamine (0.47 mL, 3.4 mmol) in dichloromethane (200 mL) that was immersed in a room temperature water bath. The rate of addition was adjusted to maintain the internal temperature of the reaction between 19.5° C. and 22.8° C. After completion of the addition, the reaction mixture was diluted with water (50 mL) and the aqueous layer was extracted with dichloromethane (3×50 mL). The combined organic layers were washed with saturated aqueous sodium chloride solution (50 mL), dried over sodium sulfate, filtered, and concentrated in vacuo. Silica gel chromatography (Gradient: 0% to 20% ethyl acetate in petroleum ether) provided the product as a yellow oil. Yield: 3.8 g, 21 mmol, 39%. The indicated relative stereochemistry of compound C69 was assigned based on nuclear Overhauser enhancement studies, which revealed an interaction between the methine protons on carbons 3a and 5. LCMS m/z 182 [M+H$^+$]. $^1$H NMR (400 MHz, CDCl$_3$) δ 4.69 (d, J=13.6 Hz, 1H), 4.62 (dd, J=10.0, 8.0 Hz, 1H), 4.19 (d, J=12.8 Hz, 1H), 3.73-3.80 (m, 1H), 3.54-3.58 (m, 1H), 3.47-3.40 (m, 1H), 2.30 (dd, J=12.8, 6.4 Hz, 1H), 1.64 (quintet, J=6.8 Hz, 1H), 1.49 (q, J=11.7 Hz, 1H), 1.20-1.29 (m, 1H), 0.75-0.79 (m, 1H), 0.44-0.51 (m, 2H), 0.03-0.11 (m, 2H).

Step 8. Synthesis of rel-(3aR,5S,7aS)-5-(cyclopropylmethyl)-7a-(2,4-difluorophenyl)hexahydro-1H-pyrano[3,4-c][1,2]oxazole (C70)

Boron trifluoride diethyl etherate (5.4 g, 17.9 mmol) was added drop-wise to a solution of rel-(3aR,5S)-5-(cyclopropylmethyl)-3,3a,4,5-tetrahydro-7H-pyrano[3,4-c][1,2]oxazole (C69) (2.7 g, 14.9 mmol) in toluene (100 mL) at an internal temperature of −72.5° C. The reaction mixture was stirred at −73° C. to −76° C. for 30 minutes, then treated with 2,4-difluoro-1-iodobenzene (98%, 4.3 g, 17.9 mmol) in one portion. While the reaction temperature was maintained below −73° C., n-butyllithium (2.5 M in hexanes, 6.0 mL, 14.9 mmol) was added in a drop-wise manner over 15 minutes. The reaction mixture was stirred at −73° C. to −75° C. for 1.5 hours, then was quenched with saturated aqueous ammonium chloride solution (10 mL) at −74° C. and allowed to warm to room temperature. The resulting mixture was extracted with ethyl acetate (300 mL), and the aqueous layer was extracted with additional ethyl acetate (250 mL and 100 mL); the combined organic layers were dried over sodium sulfate, filtered, and concentrated in vacuo. Chromatography on silica gel (Gradient: 0% to 10% ethyl acetate in petroleum ether) afforded the product as a yellow oil. Yield: 1.85 g, 6.25 mmol, 42%. LCMS m/z 296 [M+H$^+$]. $^1$H NMR (400 MHz, CDCl$_3$) δ 7.92 (q, J=8.3 Hz, 1H), 6.88 (dt, J=8.2, 2.4 Hz, 1H), 6.80 (dt, J=10.4, 2.4 Hz, 1H), 6.31 (br s, 1H), 4.11 (dd, J=12.8, 1.6 Hz, 1H), 3.80 (d, J=12.8 Hz, 1H), 3.70 (d, J=7.2 Hz, 1H), 3.61-3.67 (m, 1H), 3.52-3.55 (m, 1H), 3.04-3.09 (m, 1H), 1.94 (dd, J=14.0, 6.8 Hz, 1H), 1.59-1.67 (m, 2H), 1.45 (q, J=15.1 Hz, 1H), 1.25 (quintet, J=6.9 Hz, 1H), 0.74-0.85 (m, 1H), 0.45-0.53 (m, 2H), 0.08-0.13 (m, 2H).

Step 9. Synthesis of rel-[(2S,4R,5S)-5-amino-2-(cyclopropylmethyl)-5-(2,4-difluorophenyl)tetrahydro-2H-pyran-4-yl]methanol (C71)

rel-(3aR,5S,7aS)-5-(Cyclopropylmethyl)-7a-(2,4-difluorophenyl) hexahydro-1H-pyrano[3,4-c][1,2]oxazole (C70) (1.1 g, 4.09 mmol) was converted to the product according to the method described for the synthesis of [(2R,4R,5S)-5-amino-2-[(benzyloxy)methyl]-5-(2,4-difluorophenyl)tetrahydro-2H-pyran-4-yl]methanol (C6) in Preparation P1. The product was obtained as a dark oil (1.1 g), which was taken directly to the following step without additional purification.

Step 10. Synthesis of rel-N-{[(3S,4R,6S)-6-(cyclopropylmethyl)-3-(2,4-difluorophenyl)-4-(hydroxymethyl)tetrahydro-2H-pyran-3-yl]carbamothioyl}benzamide (C72)

Benzoyl isothiocyanate (0.6 g, 3.7 mmol) was added drop-wise to a solution of rel-[(2S,4R,5S)-5-amino-2-(cyclopropylmethyl)-5-(2,4-difluorophenyl)tetrahydro-2H-pyran-4-yl]methanol (C71) (1.10 g, 3.7 mmol) in dichloromethane (30 mL). After the reaction mixture had stirred at room temperature for 15 hours, it was concentrated in vacuo. Purification via silica gel chromatography (Gradient: 0% to 20% ethyl acetate in petroleum ether) provided the product as a brown solid. Yield: 1.14 g, 2.47 mmol, 67%. LCMS m/z 461 [M+H$^+$].

Step 11. Synthesis of rel-N-[(4aR,6S,8aS)-6-(cyclopropylmethyl)-8a-(2,4-difluorophenyl)-4,4a,5,6,8,8a-hexahydropyrano[3,4-d][1,3]thiazin-2-yl]benzamide (C73)

rel-N-{[(3S,4R,6S)-6-(Cyclopropylmethyl)-3-(2,4-difluorophenyl)-4-(hydroxymethyl)tetrahydro-2H-pyran-3-yl]carbamothioyl}benzamide (C72) was converted to the product using the method described for synthesis of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8) in Preparation P1. The product was obtained as a white solid. Yield: 430 mg, 0.97 mmol, 39%. LCMS m/z 443 [M+H$^+$]. $^1$H NMR (400 MHz, CDCl$_3$) δ 8.22 (br d, J=7.2 Hz, 2H), 7.50 (t, J=7.2 Hz, 1H), 7.37-7.45 (m, 3H), 6.85-6.94 (m, 2H), 4.13 (q, J=8.5 Hz, 1H), 3.77 (d, J=12.0 Hz, 1H), 3.67-3.73 (m, 1H), 3.10-3.17 (m, 1H), 3.00 (dd, J=12.8, 3.0, 1H), 2.64 (dd, J=12.8, 2.8 Hz, 1H), 1.93 (q, J=12.4 Hz, 1H), 1.67-1.77 (m, 2H), 0.84-0.90 (m, 1H), 0.72-0.82 (m, 1H), 0.41-0.48 (m, 2H), 0.04-0.12 (m, 2H).

Step 12. Synthesis of (4aR,6S,8aS)-6-(cyclopropylmethyl)-8a-(2,4-difluorophenyl)-4,4a,5,6,8,8a-hexahydropyrano[3,4-d][1,3]thiazin-2-amine (8)

rel-N-[(4aR,6S,8aS)-6-(Cyclopropylmethyl)-8a-(2,4-difluorophenyl)-4,4a,5,6,8,8a-hexahydropyrano[3,4-d][1,3]thiazin-2-yl]benzamide (C73) (400 mg, 0.9 mmol) was combined with ethanol (10 mL) and hydrazine (50% in water, 224 g, 7.0 mmol) and stirred at room temperature for 20 hours. The reaction mixture was concentrated in vacuo and purified by preparative HPLC (Column: Phenomenex Gemini C18, 8 μm; Mobile phase: from 46% acetonitrile in water [Ammonia (pH 10)] to 66% acetonitrile in water [Ammonia (pH 10)]. The racemic product was separated into its enantiomers using supercritical fluid chromatography (Column: Cellulose-4; Eluent: 7:3 carbon dioxide/methanol). The first-eluting enantiomer provided the product as a white solid. The indicated absolute stereochemistry was assigned to compound 8 on the basis of this compound's biological activity; its enantiomer C74 (below) proved essentially inactive (see Table 3). Yield: 55 mg, 0.47 mmol, 35%. LCMS m/z 339 [M+H$^+$]. $^1$H NMR (400 MHz, CD$_3$OD) δ 7.30-7.37 (m, 1H), 6.92-6.99 (m, 2H), 4.08 (dd, J=11.1, 2.1 Hz, 1H), 3.65-3.70 (m, 2H), 2.84-2.91 (m, 2H), 2.63-2.67 (m, 1H), 1.74 (dq, J=11.8, 2.8 Hz, 1H), 1.58-1.64 (m, 2H), 1.23 (ddd, J=13.8, 7.7, 5.9 Hz, 1H), 0.79-0.87 (m, 1H), 0.43-0.48 (m, 2H), 0.06-0.12 (m, 2H).

The second-eluting enantiomer, also obtained as a pale yellow solid, was assigned as (4aS,6R,8aR)-6-(cyclopropylmethyl)-8a-(2,4-difluorophenyl)-4,4a,5,6,8,8a-hexahydropyrano[3,4-d][1,3]thiazin-2-amine (C74). Yield: 55 mg, 0.47 mmol, 35%. LCMS m/z 339 [M+H$^+$]. $^1$H NMR (400 MHz, CD$_3$OD) δ 7.33 (td, J=9.1, 6.8 Hz, 1H), 6.91-6.98 (m, 2H), 4.08 (dd, J=10.9, 2.3 Hz, 1H), 3.64-3.70 (m, 2H), 2.84-2.91 (m, 2H), 2.63-2.67 (m, 1H), 1.74 (dq, J=11.8, 2.8 Hz, 1H), 1.57-1.64 (m, 2H), 1.22 (ddd, J=13.9, 7.8, 5.7 Hz, 1H), 0.79-0.87 (m, 1H), 0.43-0.48 (m, 2H), 0.06-0.12 (m, 2H).

Examples 9-18

(4aR,6R,8aS)-6-Cyclopropyl-8a-substituted-4,4a,5,6,8,8a-hexahydropyrano[3,4-d][1,3]thiazin-2-amines and (4aS,6S,8aR)-6-Cyclopropyl-8a-substituted-4,4a,5,6,8,8a-hexahydropyrano[3,4-d][1,3]thiazin-2-amines

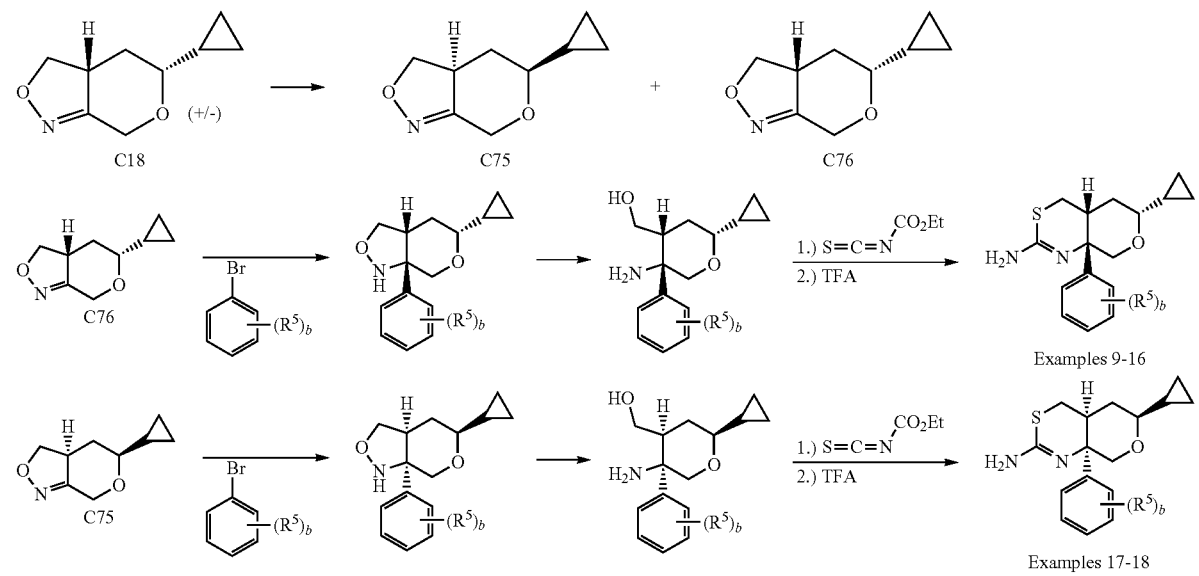

Synthesis of Examples 9-18

Step 1. Preparation of (3aS,5S)-5-cyclopropyl-3,3a,4,5-tetrahydro-7H-pyrano[3,4-c][1,2]oxazole (C75) and (3aR,5R)-5-cyclopropyl-3,3a,4,5-tetrahydro-7H-pyrano[3,4-c][1,2]oxazole (C76)

Racemic rel-(3aR,5R)-5-cyclopropyl-3,3a,4,5-tetrahydro-7H-pyrano[3,4-c][1,2]oxazole (C18) (20 g, 0.12 mol) was separated into its enantiomers using supercritical fluid chromatography (Column: ChiralPAK® AS-H, 5 μm; Eluent: 9:1 carbon dioxide/methanol). The first-eluting enantiomer provided (3aS,5S)-5-cyclopropyl-3,3a,4,5-tetrahydro-7H-pyrano[3,4-c][1,2]oxazole (C75) as a pale yellow solid. The indicated absolute stereochemistry was assigned to compound C75 on the basis of the biological activity of this compound's final targets, which proved to have very poor activity (see Examples 17-18, Table 3); the final targets of its enantiomer C76 (below) proved active (see Examples 9-16, Table 3). Yield: 8.97 g, 0.053 mol, 44%. GCMS m/z 167 [M$^+$]. $^1$H NMR (400 MHz, CDCl$_3$) δ 4.69 (d, J=13.5 Hz, 1H), 4.57 (ddd, J=10.2, 7.9, 0.7 Hz, 1H), 4.14 (dt, J=13.4, 1.0 Hz, 1H), 3.77 (dd, J=11.8, 7.7 Hz, 1H), 3.39 (qd, J=11.1, 6.7, 1H), 2.81 (ddd, J=10.3, 8.7, 1.4 Hz, 1H), 2.28 (ddd, J=13.1, 6.5, 1.6 Hz, 1H), 1.64 (ddd, J=12.8, 11.4, 11.3 Hz, 1H), 0.86-0.95 (m, 1H), 0.49-0.61 (m, 2H), 0.36-0.42 (m, 1H), 0.19-0.25 (m, 1H).

The second-eluting enantiomer provided (3aR,5R)-5-cyclopropyl-3,3a,4,5-tetrahydro-7H-pyrano[3,4-c][1,2]oxazole (C76) as a pale yellow solid. Yield: 8.75 g, 52.3 mmol, 44%. GCMS m/z 167 [M$^+$]. $^1$H NMR (400 MHz, CDCl$_3$) δ 4.72 (d, J=13.7 Hz, 1H), 4.50 (dd, J=10.3, 8 Hz, 1H), 4.13 (dd, J=13.7, 1.2 Hz, 1H), 3.79 (dd, J=11.7, 8.2 Hz, 1H), 3.40 (qd, J=11.1, 6.4 Hz, 1H), 2.82 (ddd, J=11.1, 8, 1.6 Hz, 1H), 2.29 (ddd, J=13, 6.5, 1.6 Hz, 1H), 1.59-1.67 (m, 1H), 0.93 (qt, J=8.1, 4.9 Hz, 1H), 0.52-0.63 (m, 2H), 0.38-0.44 (m, 1H), 0.21-0.27 (m, 1H).

Step 2. Synthesis of (3aR,5R,7aS)-5-cyclopropyl-7a-substituted-hexahydro-1H-pyrano[3,4-c][1,2]oxazoles and (3aS,5S,7aR)-5-cyclopropyl-7a-substituted-hexahydro-1H-pyrano[3,4-c][1,2]oxazoles Boron trifluoride diethyl etherate (0.134 mL, 0.053 mmol) was added drop-wise to a solution of (3aR,5R)-5-cyclopropyl-3,3a,4,5-tetrahydro-7H-pyrano[3,4-c][1,2]oxazole (C76) or (3aS,5S)-5-cyclopropyl-3,3a,4,5-tetrahydro-7H-pyrano[3,4-c][1,2]oxazole (C75) (75 mg, 0.45 mmol) in toluene (4 mL) cooled in a dry ice/acetone bath. The reaction mixture was stirred at −78° C. for 15 minutes, then treated with the appropriate aryl halide (0.50 mmol) dissolved in toluene (1 mL) in one portion. The reaction mixture was allowed to stir at −78° C. for 5 minutes followed by addition of tert-butyllithium (1.7 M in pentanes, 0.581 mL, 0.988 mmol) in a drop-wise manner over 5 minutes. The reaction mixture was stirred at −78° C. for 1.5 hours, then was quenched with saturated aqueous ammonium chloride solution (5 mL) at −78° C. and allowed to warm to room temperature. Water (5 mL) was added and the resulting mixture was extracted with ethyl acetate (2×40 mL); the combined organic layers were dried over magnesium sulfate, filtered, and concentrated in vacuo. The resulting residue was carried forward into the next step without purification.

Step 3. Synthesis of [(2R,4R,5S)-5-amino-2-cyclopropyl-5-substituted-tetrahydro-2H-pyran-4-yl]methanols and [(2S,4S,5R)-5-amino-2-cyclopropyl-5-substituted-tetrahydro-2H-pyran-4-yl]methanols A (3aR,5R,7aS)-5-cyclopropyl-7a-substituted-hexahydro-1H-pyrano[3,4-c][1,2]oxazole or (3aS,5S,7aR)-5-cyclopropyl-7a-substituted-hexahydro-1H-pyrano[3,4-c][1,2]oxazole was dissolved in acetic acid (3 mL) and treated with zinc powder (626 mg, 9.58 mmol). The reaction mixture was stirred at room temperature for 18 hours. Insoluble material was removed via filtration through an empty Bakerbond 6 mL polypropylene filtration column, and the column was washed with ethyl acetate (3×15 mL). The combined filtrates were then concentrated in vacuo. The residue was dissolved in methanol (1 mL) and the solution was loaded onto an Oasis® MCX (mix-mode polymeric strong cation-exchange) solid-phase extraction cartridge (Waters, 6 mL, 500 mg bed weight). The cartridge was rinsed with dichloromethane (1×4 mL) and methanol (1×4 mL). The filtrate was then loaded onto an Oasis® MCX solid-phase extraction cartridge (Waters, 6 mL, 500 mg bed weight). The cartridge was rinsed with dichloromethane (1×4 mL) and methanol (1×4 mL). The crude product was then eluted from each cartridge with a solution of ammonia in methanol (3 N, 8.0 mL). The filtrates were combined and concentrated in vacuo. The resulting residue was carried forward without further purification. Yield: 29-76% over two steps.

Step 4. Synthesis of (4aR,6R,8aS)-6-cyclopropyl-8a-substituted-4,4a,5,6,8,8a-hexahydropyrano[3,4-d][1,3]thiazin-2-amines (9-16) and (4aS,6S,8aR)-6-cyclopropyl-8a-substituted-4,4a,5,6,8,8a-hexahydropyrano [3,4-d][1,3]thiazin-2-amines (17,18)

To [(2R,4R,5S)-5-amino-2-cyclopropyl-5-substituted-tetrahydro-2H-pyran-4-yl]methanols or [(2S,4S,5R)-5-amino-2-cyclopropyl-5-substituted-tetrahydro-2H-pyran-4-yl]methanols (0.088 to 0.338 mmol, 1 eq) in 2-dram vials was added tetrahydrofuran (5 mL). Ethoxycarbonyl isothiocyanate (0.011-0.4 mL, 0.092-0.332, 1.05 eq) was added neat and the vials were shaken at room temperature for 50 minutes. The solutions were loaded onto a SilaMetS® diamine (Si-dia) solid-phase extraction cartridge (Silicycle, 6 mL, 500 mg bed weight) and the cartridges were rinsed with tetrahydrofuran (4 mL). The filtrates were concentrated in vacuo. The residues were dissolved in a 1:1:1 2-methyltetrahydrofuran/water/trifluoroacetic acid mixture (5 mL) and the vials were shaken at 65° C. for 1.5 hours. Trifluoroacetic acid (1 mL) was then added and the vials were shaken at 120° C. for 6 hours. Solvents were removed in vacuo and the residues were partitioned between aqueous half-saturated sodium bicarbonate solution (1.5 mL) and ethyl acetate (2.5 mL). The organic layers were removed and the aqueous layers were extracted with ethyl acetate (2×2.5 mL). The organics for each individual reaction were combined and passed through solid phase extraction cartridges containing sodium sulfate (6 mL cartridge, approximately 1 g bed weight). The filtrates were concentrated in vacuo. The residues were dissolved in a 1:1:1 2-methyltetrahydrofuran/water/trifluoroacetic acid mixture (5 mL) and the vials were shaken at 120° C. for 12 hours. The solvent was removed in vacuo and the residues were partitioned between aqueous half-saturated sodium bicarbonate (1.5 mL) and ethyl acetate (2.5 mL). The organic layers were removed and the aqueous layers were extracted with ethyl acetate (2×2.5 mL). The organics from each individual reaction were combined and passed through solid phase extraction cartridges containing sodium sulfate (6 mL cartridge, approximately 1 g bed weight). After concentration in vacuo, dissolution in dimethyl sulfoxide (1 mL) and filtration through a Waters Oasis® filter plate to remove particulates, purification was carried out via reversed phase HPLC (Example 9: Column: Waters XBridge C18, 5 μm; Mobile phase A: 0.03% ammonium hydroxide in water (v/v); Mobile phase B: 0.03% ammonium hydroxide in acetonitrile (v/v); Gradient: 20% to 100% B); (Example 12: Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 5% to 100% B); (All other examples: Column: Waters XBridge C18, 5 μm; Mobile phase A: 0.03% ammonium hydroxide in water (v/v); Mobile phase B: 0.03% ammonium hydroxide in acetonitrile (v/v); Gradient: 20% to 100% B). See Table 1 and Table 2 for characterization data.

TABLE 1

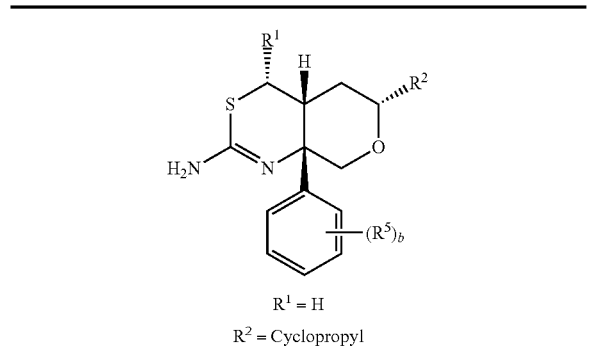

R$^1$ = H
R$^2$ = Cyclopropyl

| Example # | Structure | Calc'd Exact Mol. Wt. | Mass Spec. (M + 1) | HPLC RT (min) |
|---|---|---|---|---|
| 9 | 2,4,6-trifluorophenyl | 342.10 | 343.28 | 2.633[1] |
| 10 | 4-fluorophenyl | 306.12 | 307.24 | 2.018[2] |
| 11 | 2,5-difluorophenyl | 324.11 | 325.25 | 2.079[2] |
| 12 | 2,6-difluorophenyl | 324.11 | 325.25 | 2.018[2] |
| 13 | 2-fluorophenyl | 306.12 | 307.24 | 2.068[2] |
| 14 | phenyl | 288.12 | 289.23 | 1.95[2] |
| 15 | 2-fluoro-4-methylphenyl | 320.13 | 321.25 | 2.27[2] |
| 16 | 3-fluoro-4-methylphenyl | 320.13 | 321.25 | 2.22[2] |

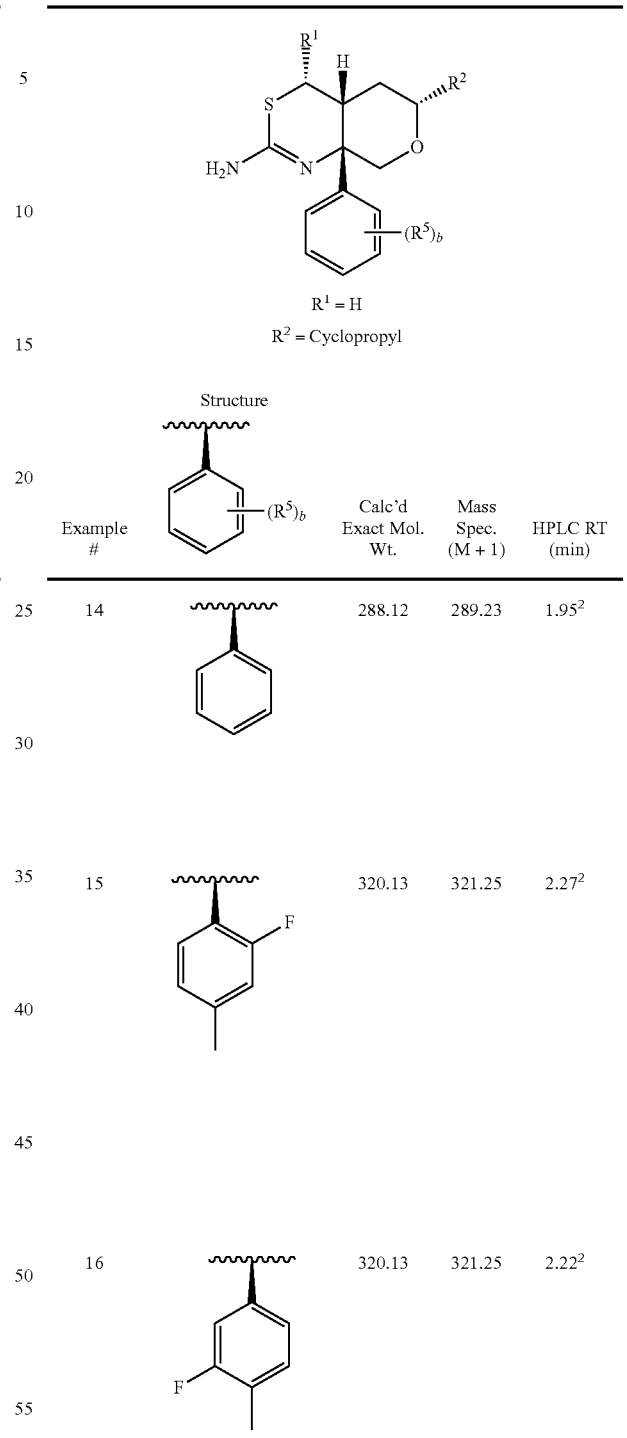

[1] Column: Waters XBridge C18, 4.6 × 50 mm, 5 μm; Mobile phase A: 0.03% ammonium hydroxide in water (v/v); Mobile phase B: 0.03% ammonium hydroxide in acetonitrile (v/v); Gradient: 5.0% to 95% B, linear over 4.0 minutes; Flow rate: 2 mL/min.

[2] Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5% to 95% B, linear over 4.0 minutes; Flow rate: 2 mL/min.

TABLE 2

R¹ = H
R² = Cyclopropyl

| Example # | Structure | Calc'd Exact Mol. Wt. | Mass Spec. (M + 1) | HPLC RT (min) |
|---|---|---|---|---|
| 17 | 2-F phenyl | 306.12 | 307.24 | 2.068[1] |

TABLE 2-continued

R¹ = H
R² = Cyclopropyl

| Example # | Structure | Calc'd Exact Mol. Wt. | Mass Spec. (M + 1) | HPLC RT (min) |
|---|---|---|---|---|
| 18 | 4-F phenyl | 306.12 | 307.24 | 2.018[1] |

[1]Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5% to 95% B, linear over 4.0 minutes; Flow rate: 2 mL/min.

Example 19

(4aR,6R,8aS)-8a-(2,4-Difluorophenyl)-6-(5,5-dimethyltetrahydrofuran-2-yl)-4,4a,5,6,8,8a-hexahydropyrano[3,4-d][1,3]thiazin-2-amine (19)

Step 1. Synthesis of N-[(4aR,6R,8aS)-8a-(2,4-difluorophenyl)-6-(1-hydroxy-4-methylpent-4-en-1-yl)-4,4a,5,6,8,8a-hexahydropyrano[3,4-d][1,3]thiazin-2-yl]benzamide (C77)

A solution of 4-iodo-2-methylbut-1-ene (942 mg, 4.8 mmol) in diethyl ether (5 mL) was added to a solution of tert-butyllithium (1.7 M in pentane, 5.65 mL, 9.6 mmol) in diethyl ether (15 mL) at −78° C. The reaction mixture was stirred at −78° C. for 35 minutes and then N-[(4aR,6R,8aS)-8a-(2,4-difluorophenyl)-6-formyl-4,4a,5,6,8,8a-hexahydropyrano[3,4-d][1,3]thiazin-2-yl]benzamide (P1) (400 mg, 0.96 mmol) in diethyl ether (5 mL) and tetrahydrofuran (4 mL) was added drop-wise over 10 minutes. The mixture was stirred at −78° C. for 15 minutes, then allowed to warm to 0° C. and stirred at 0° C. for 1 hour. The mixture was allowed to warm to room temperature, then stirred at room temperature for 15 minutes. The mixture was diluted with a saturated aqueous solution of ammonium chloride (35 mL) and extracted with ethyl acetate (3×35 mL). The combined ethyl acetate extracts were dried over sodium sulfate, filtered and concentrated to afford a yellow oil. Purification via silica gel chromatography (Gradient: 0% to 90% ethyl acetate in heptane) afforded the product as a white solid. Yield: 108 mg, 23%. LCMS m/z 487.3 [M+H$^+$]. $^1$H NMR (400 MHz, CDCl$_3$) δ 8.22 (br d, J=6.8 Hz, 2H), 7.31-7.53 (m, 4H), 6.68-6.96 (m, 2H), 4.72-4.73 (m, 1H), 4.17 (d, J=12.5 Hz, 1H), 3.80-3.87 (m, 1H), 3.76 (br s, 1H), 3.61-3.65 (m, 1H), 3.56 (br d, J=8.2 Hz, 1H), 3.13 (br s, 1H), 3.03 (dd, J=12.7, 4.1 Hz, 1H), 2.68 (m, 1H), 2.0-2.29 (m, 4H), 1.74 (s, 3H), 1.59-1.69 (m, 2H).

Step 2. Synthesis of N-[(4aR,6R,8aS)-8a-(2,4-difluorophenyl)-6-(5,5-dimethyltetrahydrofuran-2-yl)-4,4a,5,6,8,8a-hexahydropyrano[3,4-d][1,3]thiazin-2-yl]benzamide (C78)

Boron trifluoride diethyl etherate (21 μL, 0.98 mmol) was added to a solution of N-[(4aR,6R,8aS)-8a-(2,4-difluorophenyl)-6-(1-hydroxy-4-methylpent-4-en-1-yl)-4,4a,5,6,8,8a-hexahydropyrano[3,4-d][1,3]thiazin-2-yl]benzamide (C77) (106 mg, 0.22 mmol) in dichloromethane (7 mL) at 0° C. The mixture was stirred at 0° C. for 5 minutes, then allowed to warm to room temperature and stirred for a further 5 hours. The mixture was diluted with water (15 mL) and extracted with ethyl acetate (3×20 mL). The combined ethyl acetate extracts were dried over sodium sulfate, filtered and concentrated to afford a yellow oil. Purification via silica gel chromatography (Gradient: 0% to 90% ethyl acetate in heptane) afforded the product as a white solid. By $^1$H NMR analysis, this was isolated as a single diastereomer. Yield: 30.1 mg, 28%. LCMS m/z 487.2 [M+H$^+$]. $^1$H NMR (400 MHz, CDCl$_3$) δ 8.24 (br d, 7.0 Hz, 2H), 7.37-7.53 (m, 4H), 6.85-6.95 (m, 2H), 4.15 (d, J=12.1 Hz, 1H), 3.90 (ap. q, J=6.8 Hz, 1H), 3.79 (d, J=12.1 Hz, 1H), 3.53 (ddd, J=10.1, 6.6, 3.3 Hz, 1H), 3.10-3.15 (m, 1H), 3.01 (dd, J=12.8, 4.2 Hz, 1H), 2.66 (dd, J=12.7, 2.7 Hz, 1H), 2.03-2.12 (m, 1H), 1.86-1.99 (m, 3H), 1.68-1.78 (m, 2H), 1.27 (s, 3H), 1.22 (s, 3H).

Step 3. Synthesis of (4aR,6R,8aS)-8a-(2,4-difluorophenyl)-6-(5,5-dimethyltetrahydrofuran-2-yl)-4,4a,5,6,8,8a-hexahydropyrano[3,4-d][1,3]thiazin-2-amine (19)

Methylamine (8.0 M in ethanol, 500 μL, 4.0 mmol) was added to a solution of N-[(4aR,6R,8aS)-8a-(2,4-difluorophenyl)-6-(5,5-dimethyltetrahydrofuran-2-yl)-4,4a,5,6,8,8a-hexahydropyrano[3,4-d][1,3]thiazin-2-yl]benzamide (C78) (30 mg, 0.062 mmol) in ethanol (500 μL). The reaction mixture was stirred at room temperature overnight. The mixture was concentrated to an oil and combined with material derived from a reaction run on 0.01 mmol in a similar manner. Purification via silica gel chromatography (Gradient: 0% to 15% methanol in dichloromethane) afforded the product as a white solid. By $^1$H NMR analysis, this product was a single diastereomer. Yield: 19.9 mg, 72%. LCMS m/z 383.2 [M+H$^+$]. $^1$H NMR (400 MHz, CD$_3$OD) δ 7.31-7.37 (m, 1H), 6.93-7.00 (m, 2H), 4.06 (dd, J=10.9, 2.0 Hz, 1H), 3.89 (ap. q, J=6.6 Hz, 1H), 3.69 (d, J=11.3 Hz, 1H), 3.49-3.54 (m, 1H), 2.86-2.91 (m, 2H), 2.66-2.70 (m, 1H), 1.99-2.09 (m, 2H), 1.65-1.78 (m, 4H), 1.26 (s, 3H), 1.23 (s, 3H).

Example 20

(4aR,6R,8aS)-8a-(2,4-Difluorophenyl)-6-[(1R,2R)-2-methylcyclopropyl]-4,4a,5,6,8,8a-hexahydropyrano[3,4-d][1,3]thiazin-2-amine (20)

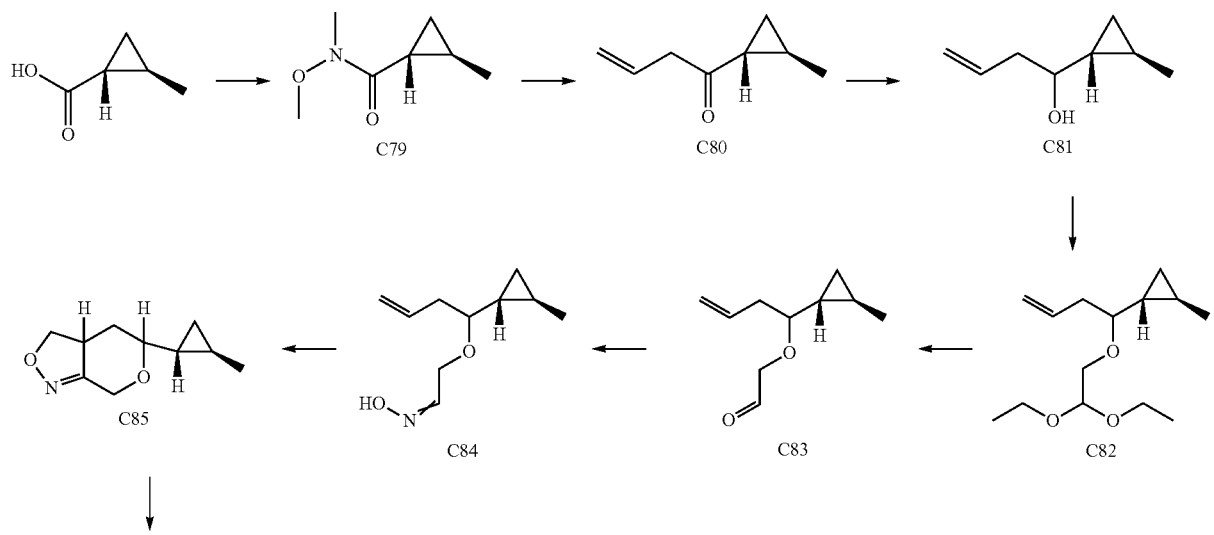

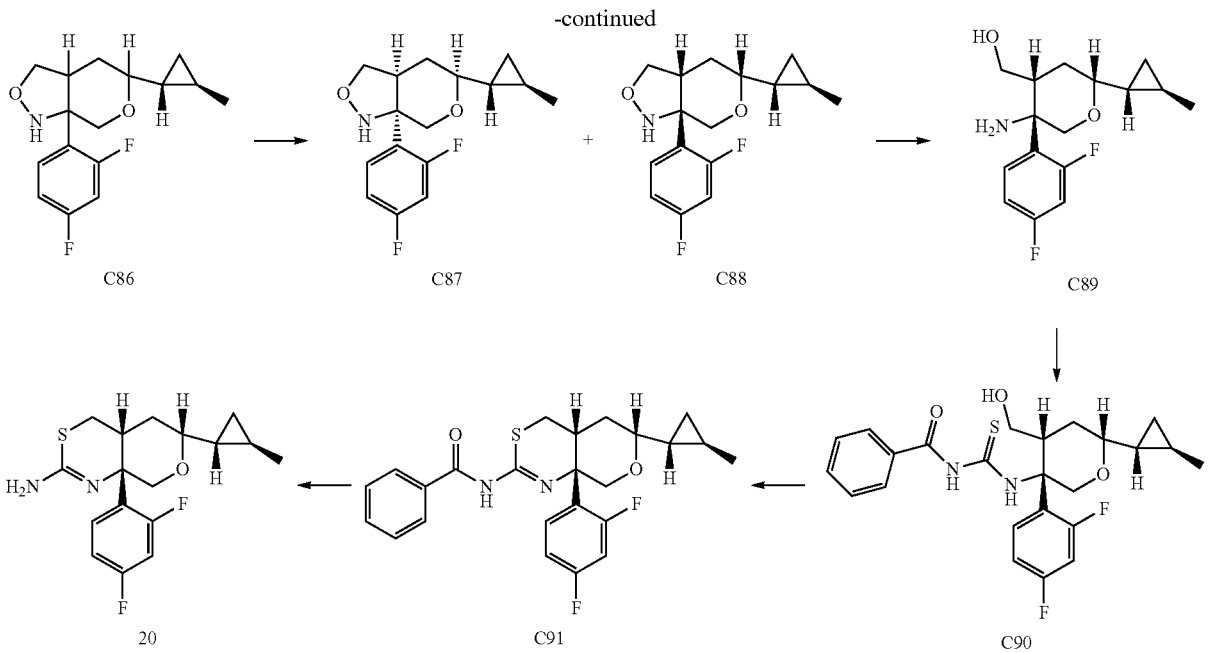

Step 1: Synthesis of (1R,2R)—N-methoxy-N,2-dimethylcyclopropanecarboxamide (C79)

To a solution of (1R,2R)-2-methylcyclopropanecarboxylic acid (44 g, 0.44 mol) in dichloromethane (600 mL) was added 1,1'-carbonyldiimidazole (79 g, 0.45 mol) portion-wise at 20° C. The reaction was stirred at 25° C. for 2 hours. N,O-Dimethylhydroxylamine hydrochloride (52 g, 0.53 mol) was added portion-wise and stirring was continued at 25° C. for 16 hours. The reaction mixture was washed with water (100 mL). The organic layer was dried over sodium sulfate, filtered and concentrated in vacuo. Silica gel chromatography (Gradient: 2% to 20% ethyl acetate in petroleum ether) provided the product as a colorless oil. Yield: 52 g, 363 mmol, 82%. $^1$H NMR (400 MHz, CDCl$_3$) δ 3.74 (s, 3H), 3.19 (s, 3H), 1.80-1.86 (m, 1H), 1.30-1.38 (m, 1H), 1.17 (dt, J=8.5, 4.3 Hz, 1H), 1.12 (d, J=6 Hz, 3H), 0.64 (ddd, J=8.2, 6.1, 3.8 Hz, 1H).

Step 2: Synthesis of 1-[(1R,2R)-2-methylcyclopropyl]but-3-en-1-one (C80)

To a solution of C79 (52.0 g, 0.364 mol) in tetrahydrofuran (500 mL) was added allylmagnesium bromide (1 M in diethyl ether, 660 mL, 0.66 mol) at −70° C. The mixture was stirred at −70° C. for 3 hours. The mixture was quenched with saturated aqueous ammonium chloride solution (600 mL) and extracted with ethyl acetate (2 L). The organic layer was dried over sodium sulfate, filtered and concentrated in vacuo to give the crude product as a brown oil, which was directly in the next step. Yield: 45.0 g, ≤0.363 mol, ≤100%.

Step 3: Synthesis of 1-[(1R,2R)-2-methylcyclopropyl]but-3-en-1-ol (C81)

To a solution of crude C80 (45 g) in dry tetrahydrofuran (500 mL) was added lithium aluminum hydride (16.6 g, 0.44 mol) portion-wise slowly at −70° C. The mixture was stirred at −70° C. for 1 hour. The mixture was slowly quenched with saturated aqueous ammonium chloride solution (400 mL) and extracted with ethyl acetate (1 L). The organic layer was dried over sodium sulfate, filtered and concentrated in vacuo. Silica gel chromatography (Gradient: 2% to 20% ethyl acetate in petroleum ether) provided the product as a colorless oil. This material consisted of a 1:1 mixture of diastereomers via $^1$H NMR analysis. Yield: 27.5 g, 218 mmol, 60% over 2 steps from (C80). $^1$H NMR (400 MHz, CDCl$_3$) δ 5.88-5.92 (m, 1H), 5.08-5.15 (m, 2H), 2.93-3.00 (m, 1H), 2.23-2.42 (m, 2H), 1.66-1.76 (m, 1H), 1.05 (d, J=6 Hz, 1.5H), 1.02 (d, J=5.5 Hz, 1.5H), 0.70-0.76 (m, 0.5H), 0.57-0.66 (m, 1.5H), 0.45-0.49 (m, 0.5H), 0.33-0.38 (m, 0.5H), 0.23-0.28 (m, 1H).

Step 4: Synthesis of (1R,2R)-1-[1-(2,2-diethoxyethoxyl)but-3-en-1-yl]-2-methylcyclopropane (C82)

To a suspension of sodium hydride (60% in mineral oil, 31 g, 0.79 mol) in N,N-dimethylformamide (250 mL) was added C81 (23.0 g, 0.183 mol) drop-wise and then the reaction mixture was stirred for 1 hour. 2-Bromo-1,1-diethoxyethane (126 g, 0.51 mol) was added at room temperature and then the reaction mixture was stirred at 140° C. for 2 hours. It was then quenched slowly with water (500 mL) and extracted with ethyl acetate (1 L). The organic phase was washed with water (2×200 mL), dried over sodium sulfate, filtered, and concentrated in vacuo to give the crude product as a brown oil, which was carried into the next step without additional purification.

Step 5: Synthesis of ({1-[(1R,2R)-2-methylcyclopropyl]but-3-en-1-yl}oxy)acetaldehyde (C83)

To a solution of crude C82 in tetrahydrofuran (780 mL) was added aqueous hydrochloric acid (2 M, 780 mL, 0.78 mol). The mixture was stirred at room temperature for 16 hours, then extracted with ethyl acetate (2 L). The organic phase was washed with saturated aqueous sodium chloride solution (3×1 L), dried over sodium sulfate, filtered and concentrated in vacuo to provide the product as a pale brown oil that was carried forward without further purification.

Step 6: Synthesis of N-hydroxy-2-({1-[(1R,2R)-2-methylcyclopropyl]but-3-en-1-yl}oxy)ethanimine (C84)

To a mixture of crude C83 and sodium acetate (123 g, 1.50 mol) in ethanol/water (2:1, 750 mL) was added hydroxylamine hydrochloride (62 g, 0.90 mol). The reaction was stirred at 60° C. for 16 hours. The reaction was concentrated and extracted with ethyl acetate (2 L). The organic layer was dried over sodium sulfate, filtered and concentrated in vacuo. Silica gel chromatography (Gradient: 2% to 20% ethyl acetate in petroleum ether) provided the product as a brown oil. Yield: 17 g, 93 mmol, 31% over 3 steps from (C81).

Step 7: Synthesis of 5-[(1R,2R)-2-methylcyclopropyl]-3,3a,4,5-tetrahydro-7H-pyrano[3,4-c][1,2]oxazole (C85)

To a mixture of compound C84 (16 g, 87 mmol) and triethylamine (662 mg, 6.60 mmol) in dichloromethane (350 mL) was slowly added bleach (6.15% aqueous sodium hypochlorite, 160 mL) via an addition funnel. After the addition, the mixture was stirred at room temperature for 30 minutes. The organic layer was washed with water (3×300 mL), dried over sodium sulfate, filtered, and concentrated in vacuo. Silica gel chromatography (Gradient: 2% to 20% ethyl acetate in petroleum ether) provided the product as a colorless oil. Yield: 8.4 g, 46 mmol, 52%. $^1$H NMR (400 MHz, CDCl$_3$) δ 4.65 (d, J=13.7 Hz, 1H), 4.52 (dd, J=10.1, 7.8 Hz, 1H), 4.05 (dd, J=13.3, 1.2 Hz, 1H), 3.71 (dd, J=11.7, 8.2 Hz, 1H), 3.32 (qd, J=11.1, 6.4 Hz, 1H), 2.78 (ddd, J=10.9, 8, 1.8 Hz, 1H), 2.19 (ddd, J=12.9, 6.6, 1.6 Hz, 1H), 1.47-1.58 (m, 1H), 0.99 (d, J=6.2 Hz, 3H), 0.69-0.78 (m, 1H), 0.56 (tt, J=8.4, 4.5 Hz, 1H), 0.29-0.33 (m, 1H), 0.21 (dt, J=8.6, 4.9 Hz, 1H).

Step 8: Synthesis of 7a-(2,4-difluorophenyl)-5-[(1R,2R)-2-methylcyclopropyl]hexahydro-1H-pyrano[3,4-c][1,2]oxazole (C86)

To a solution of C85 (2.58 g, 14.2 mmol) in toluene (50 mL) cooled to −78° C. was added boron trifluoride diethyl etherate (4.23 mL, 15.9 mmol) drop-wise. After stirring for 30 minutes at −78° C., 2,4-difluoro-1-iodobenzene (3.90 g, 15.9 mmol) was added, followed by drop-wise addition of n-butyllithium (2.5 M in hexanes, 6.04 mL, 15.1 mmol). The reaction was stirred at −78° C. for 90 minutes at which point saturated aqueous ammonium chloride solution (10 mL) was added. The reaction was allowed to warm to room temperature and then taken up in ethyl acetate. The organic layer was washed with water and with saturated aqueous sodium chloride solution and then concentrated in vacuo. Silica gel chromatography (Gradient: 0% to 25% ethyl acetate in heptane) provided the product as a colorless oil. Yield: 1.25 g, 4.23 mmol, 30%. LCMS m/z 296.2 [M+H$^+$]. $^1$H NMR (400 MHz, CDCl$_3$): characteristic peaks δ 7.82-7.88 (m, 1H), 6.79-6.84 (m, 1H), 6.68-6.74 (m, 1H), 3.93-3.97 (m, 1H), 3.72-3.76 (m, 1H), 3.63-3.66 (m, 1H), 3.44-3.48 (m, 1H), 2.83-2.98 (m, 1H), 1.83-1.92 (m, 1H), 1.44-1.59 (m, 1H), 0.99-1.01 (m, 1H), 0.72-0.87 (m, 1H).

Step 9: Isolation of (3aS,5S,7aR)-7a-(2,4-difluorophenyl)-5-[(1R,2R)-2-methylcyclopropyl]hexahydro-1H-pyrano[3,4-c][1,2]oxazole (C87) and (3aR,5R,7aS)-7a-(2,4-difluorophenyl)-5-[(1R,2R)-2-methylcyclopropyl]hexahydro-1H-pyrano[3,4-c][1,2]oxazole (C88)

The diastereomeric mixture 7a-(2,4-difluorophenyl)-5-[(1R,2R)-2-methylcyclopropyl]hexahydro-1H-pyrano[3,4-c][1,2]oxazole (C86) was separated into its diastereomers using supercritical fluid chromatography (Column: Lux Cellulose-4, 5 µm; Eluent: 85%:15% carbon dioxide/methanol).

The first-eluting diastereomer provided (3aS,5S,7aR)-7a-(2,4-difluorophenyl)-5-[(1R,2R)-2-methylcyclopropyl]hexahydro-1H-pyrano[3,4-c][1,2]oxazole (C87) as a colorless oil. Yield: 617 mg, 2.08 mmol. LCMS m/z 296.2 [M+H$^+$]. $^1$H NMR (400 MHz, CDCl$_3$) δ 7.89-7.95 (m, 1H), 6.86-6.90 (m, 1H), 6.78 (m, 1H), 4.02 (dd, J=12.5, 2 Hz, 1H), 3.82 (d, J=12.7 Hz, 1H), 3.71 (d, J=7 Hz, 1H), 3.53 (dd, J=7.1, 5 Hz, 1H) 3.01 (dddd, J=11.5, 6.8, 4.9, 1.8 Hz, 1H), 2.89-2.95 (m, 1H), 1.93 (ddd, J=14.2, 6.9, 2.2 Hz, 1H), 1.51-1.61 (m, 1H), 1.08 (d, J=5.9 Hz, 3H), 0.77-0.86 (m, 1H), 0.65 (tt, J=8.4, 4.4 Hz, 1H), 0.40-0.44 (m, 1H), 0.29 (dt, J=8.5, 4.9 Hz, 1H).

The second-eluting diastereomer provided (3aR,5R,7aS)-7a-(2,4-difluorophenyl)-5-[(1R,2R)-2-methylcyclopropyl]hexahydro-1H-pyrano[3,4-c][1,2]oxazole (C88) as a colorless oil. Yield: 362 mg, 1.23 mmol, LCMS m/z 296.2 [M+H$^+$]. $^1$H NMR (400 MHz, CDCl$_3$) δ 7.89-7.95 (m, 1H), 6.86-6.90 (m, 1H), 6.78 (ddd, J=11.9, 8.9, 2.5 Hz, 1H), 4.02 (dd, J=12.7, 2 Hz, 1H), 3.80 (d, J=12.5 Hz, 1H), 3.71 (d, J=7 Hz, 1H), 3.53 (dd, J=7.1, 5.0 Hz, 1H), 3.02 (dddd, J=11.5, 6.7, 4.9, 1.9 Hz, 1H), 2.91-2.96 (m, 1H), 1.96 (ddd, J=14.1, 6.9, 2.1 Hz, 1H), 1.56-1.66 (m, 1H), 1.07 (d, J=5.9 Hz, 3H), 0.56-0.73 (m, 3H), 0.34 (dt, J=8, 4.8, 1H). The indicated absolute stereochemistry was assigned to C88 based on the biological activity of this compound's final target, which proved active (Table 3).

Step 10: Synthesis of {(2R,4R,5S)-5-amino-5-(2,4-difluorophenyl)-2-[(1R,2R)-2-methylcyclopropyl]tetrahydro-2H-pyran-4-yl}methanol (C89)

To a solution of C88 (362 mg, 1.23 mmol) in acetic acid (4.17 mL) was added zinc powder (802 mg, 12.3 mmol) portion-wise. The resulting heterogeneous mixture was stirred at room temperature for 16 hours. The reaction mixture was diluted with methanol and filtered through a pad of Celite using additional methanol. The filtrate was concentrated in vacuo and the resulting residue was taken up in ethyl acetate. The organic layer was washed with saturated aqueous sodium bicarbonate solution and with water, dried over magnesium sulfate, filtered and concentrated in vacuo to afford the product as a clear gum that was carried to the next step without further purification. Yield: 338 mg, 1.14 mmol, 93%. LCMS m/z 298.2 [M+H$^+$]. $^1$H NMR (400 MHz, CDCl$_3$) δ 7.62-7.68 (m, 1H), 6.92-6.96 (m, 1H), 6.8 (ddd, J=12.6, 8.5, 2.5 Hz, 1H), 4.10 (dd, J=11.4, 2.6 Hz, 1H), 3.53 (dd, J=11.5, 2.5 Hz, 1H), 3.33-3.39 (m, 2H), 2.90 (ddd, J=11.2, 8.2, 2.5 Hz, 1H), 2.04-2.24 (m, 2H), 1.77-1.82 (m, 1H), 1.07 (d, J=5.9 Hz, 3H), 0.65-0.77 (m, 2H), 0.6 (dt, J=8.8, 4.6 Hz, 1H), 0.36 (dt, J=8, 4.8 Hz, 1H).

Step 11: Synthesis of N-({(3S,4R,6R)-3-(2,4-difluorophenyl)-4-(hydroxymethyl)-6-[(1R,2R)-2-methylcyclopropyl]tetrahydro-2H-pyran-3-yl}carbamothioyl)benzamide (C90)

To a solution of C89 (330 mg, 1.11 mmol) in dichloromethane (10 mL) cooled to 0° C. was added benzoyl isothiocyanate (453 mg, 2.78 mmol) drop-wise. The reaction was allowed to slowly warm to room temperature and stir at that temperature for 72 hours. The reaction mixture was taken up in dichloromethane and the organic layer was washed with water. The organic layer was concentrated in vacuo. Silica gel chromatography (Gradient: 40% to 60% ethyl acetate in heptane) provided the product as a white foam. Yield: 316 mg, 0.69 mmol, 62%. $^1$H NMR (400 MHz, CD$_3$OD), characteristic peaks: δ 7.64-7.97 (m, 2H), 7.63-7.67 (m, 1H), 7.52-7.57

(m, 2H), 7.43-7.50 (m, 1H), 6.86-6.96 (m, 2H), 3.44-3.51 (m, 1H), 3.04 (ddd, J=11.1, 7.9, 2.5 Hz, 1H), 2.08-2.13 (m, 1H), 1.86-1.98 (m, 1H), 1.06 (d, J=5.9 Hz, 3H), 0.65-0.77 (m, 2H), 0.60 (dt, J=8.6, 4.5 Hz, 1H), 0.27 (dt, J=8.1, 4.8 Hz, 1H).

Step 12: Synthesis of N-{(4aR,6R,8aS)-8a-(2,4-difluorophenyl)-6-[(1R,2R)-2-methylcyclopropyl]-4,4a,5,6,8,8a-hexahydropyrano[3,4-d][1,3]thiazin-2-yl}benzamide (C91)

To a solution of C90 (105 mg, 0.23 mmol) in dichloromethane (3 mL) was added Ghosez's reagent (60.9 mg, 0.46 mmol) drop-wise. The reaction mixture was allowed to stir at room temperature for 2 hours. The reaction mixture was taken up in dichloromethane and the organic layer was washed with saturated aqueous sodium bicarbonate solution and with water, dried over magnesium sulfate, filtered and concentrated in vacuo. Silica gel chromatography (Gradient: 10% to 40% ethyl acetate in heptane) provided the product as a white solid. Yield: 48 mg, 0.11 mmol, 48%. LCMS m/z 443.3 [M+H$^+$].

Step 13: Synthesis of (4aR,6R,8aS)-8a-(2,4-difluorophenyl)-6-[(1R,2R)-2-methylcyclopropyl]-4,4a,5,6,8,8a-hexahydropyrano[3,4-d][1,3]thiazin-2-amine. (20)

To a solution of C91 (48 mg, 0.11 mmol) in ethanol (2 mL) was added methylamine (8 M in ethanol, 3.0 mL, 6.7 mmol). The reaction was allowed to stir at room temperature for 16 hours, at which point the reaction mixture was concentrated in vacuo. The residue was dissolved in dimethyl sulfoxide (0.9 mL) and purified via reversed phase HPLC. (Column: Waters XBridge C18, 5 μm; Mobile phase A: 0.03% ammonium hydroxide in water (v/v); Mobile phase B: 0.03% ammonium hydroxide in acetonitrile (v/v); Gradient: 20% to 60% B). Yield: 24 mg, 73 μmol, 67%. LCMS m/z 339.1 [M+H$^+$]. $^1$H NMR (400 MHz, DMSO-d$_6$), characteristic peaks: δ 7.30-7.33 (m, 1H), 7.14-7.18 (m, 1H), 7.07 (t, J=8.6 Hz, 1H), 3.78 (d, J=10.5 Hz, 1H), 3.50 (d, J=11 Hz, 1H), 2.88-2.91 (m, 1H), 2.61-2.69 (m, 2H). 1.67-1.73 (m, 1H), 1.55 (d, J=13.2 Hz, 1H), 0.99 (d, J=6.1 Hz, 3H), 0.61-0.67 (m, 1H), 0.53-0.57 (m, 1H), 0.43-0.46 (m, 1H), 0.16-0.18 (m, 1H).

Example 21

(4aR,6R,8aS)-8a-(2,4-Difluorophenyl)-6-[(2S)-tetrahydrofuran-2-yl]-4,4a,5,6,8,8a-hexahydropyrano[3,4-d][1,3]thiazin-2-amine (21)

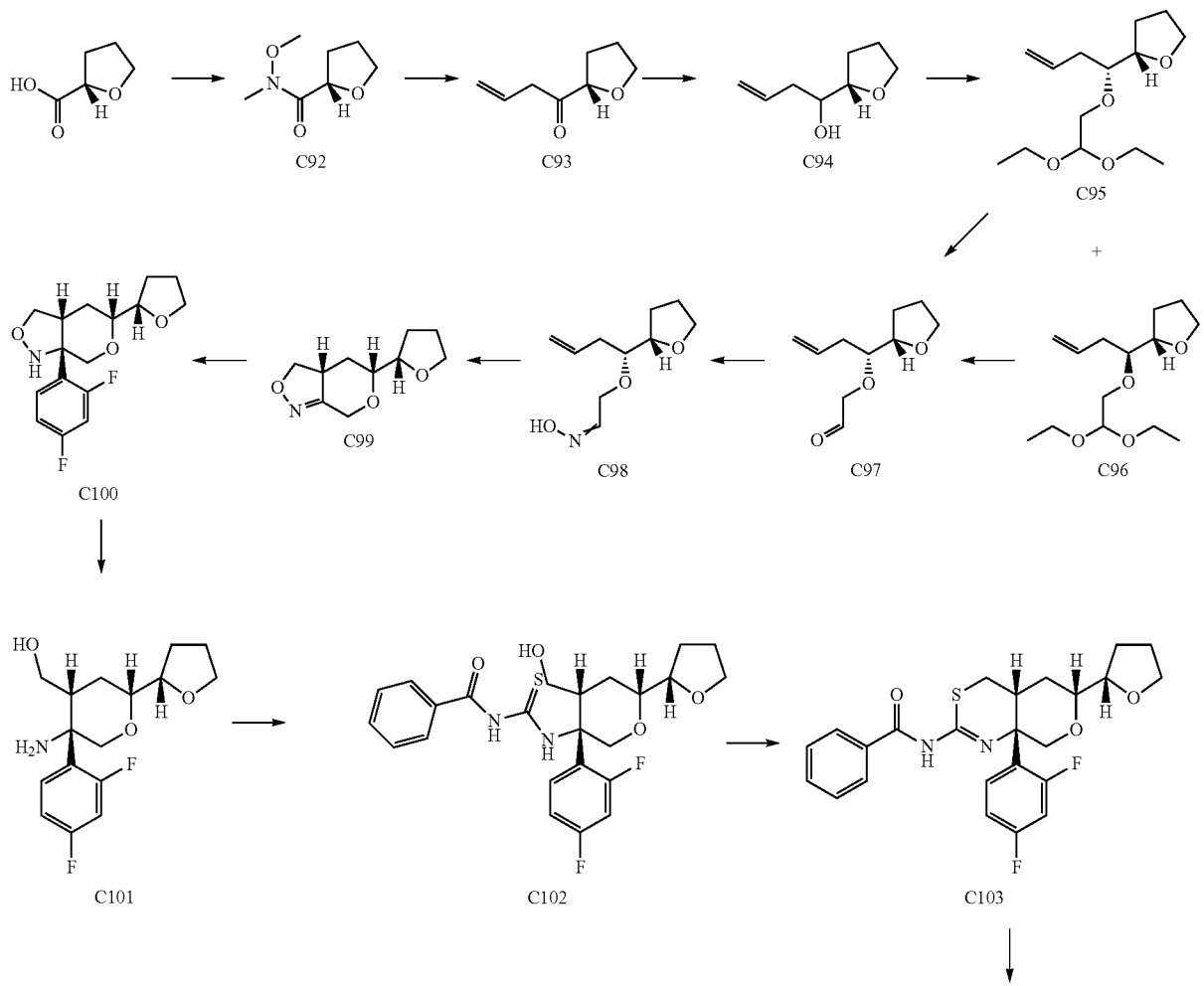

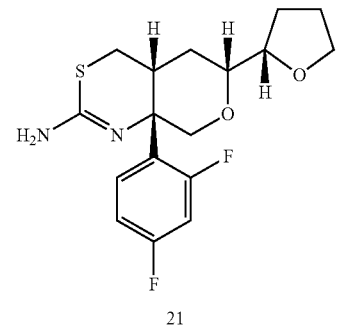

21

Step 1: Synthesis of (2S)—N-methoxy-N-methyltetrahydrofuran-2-carboxamide (C92)

(2S)-Tetrahydrofuran-2-carboxylic acid was converted to the product using the method described for the synthesis of (1R,2R)—N-methoxy-N,2-dimethylcyclopropanecarboxamide (C79) in Example 20. The resulting product was used in the next step without further purification. Yield: 24.6 g, ≤0.153 mol, ≤90%.

Step 2: Synthesis of 1-[(2S)-tetrahydrofuran-2-yl]but-3-en-1-one (C93)

(2S)—N-Methoxy-N-methyltetrahydrofuran-2-carboxamide (C92) was converted to the product using the method described for the synthesis of 1-[(1R,2R)-2-methylcyclopropyl]but-3-en-1-one (C80) in Example 20. The resulting product was used in the next step without further purification. Yield: 19 g, ≤0.14 mol, ≤87%.

Step 3: Synthesis of 1-[(2S)-tetrahydrofuran-2-yl]but-3-en-1-ol (C94)

To a solution of crude (C93) (19 g, ≤0.14 mol) in anhydrous ethanol (300 mL) at 0° C. was added sodium borohydride (11.4 g, 0.30 mol) portion-wise. After the addition the reaction was stirred at room temperature for 2 hours. The reaction mixture was then concentrated in vacuo and the residue was taken up in water (200 mL) and extracted with ethyl acetate (3×200 mL). The combined organic layers were washed with saturated aqueous sodium chloride solution (200 mL) and concentrated in vacuo to provide the product as a yellow oil, which was used in the next step without further purification. Yield: 16.0 g, ≤1.112 mol, ≤30%.

Step 4: Synthesis of (2S)-2-[(1R)-1-(2,2-diethoxyethoxyl)but-3-en-1-yl]tetrahydrofuran (C95) and (2S)-2-[(1S)-1-(2,2-diethoxyethoxyl)but-3-en-1-yl]tetrahydrofuran (C96)

To a solution of crude (C94) (16.0 g, ≤1.112 mol) in tetrahydrofuran (600 mL) at 0° C. was added sodium hydride (60% in mineral oil, 13.5 g, 0.33 mol) portion-wise. After addition was complete, the reaction was allowed to warm to room temperature and stir at that temperature for 30 minutes. 2-Bromo-1,1-diethoxyethane (83 g, 0.33 mol) was added and the reaction was refluxed for 16 hours. The reaction mixture was cooled to room temperature and poured into ice-water (100 mL). The aqueous layer was washed with ethyl acetate (3×200 mL), and the organic phases were combined and washed with saturated aqueous sodium chloride solution (200 mL), dried over sodium sulfate, filtered and concentrated in vacuo. Silica gel chromatography (Gradient: 1% to 10% ethyl acetate in petroleum ether) provided (2S)-2-[(1R)-1-(2,2-diethoxyethoxyl)but-3-en-1-yl]tetrahydrofuran as the first eluting isomer and (2S)-2-[(1S)-1-(2,2-diethoxyethoxyl)but-3-en-1-yl]tetrahydrofuran as the second eluting isomer, both as yellow oils.

(2S)-2-[(1R)-1-(2,2-Diethoxyethoxyl)but-3-en-1-yl]tetrahydrofuran (C95). Yield: 5.8 g, 22.5 mmol, 15% over 4 steps from (2S)-tetrahydrofuran-2-carboxylic acid. The indicated absolute stereochemistry was assigned to (C95) based on the biological activity of this compound's final target, which proved active (Table 3). $^1$H NMR (400 MHz, CDCl$_3$) δ 5.83-5.93 (m, 1H), 5.03-5.11 (m, 2H), 4.56-4.59 (m, 1H), 3.81-3.89 (m, 2H), 3.51-3.75 (m, 7H), 3.42-3.46 (m, 1H), 2.26-2.30 (m, 2H), 1.81-1.93 (m, 4H), 1.19-1.22 (m, 6H).

(2S)-2-[(1S)-1-(2,2-Diethoxyethoxy)but-3-en-1-yl]tetrahydrofuran (C96). Yield: 7.1 g, 27.5 mmol, 18% over 4 steps from (2S)-Tetrahydrofuran-2-carboxylic acid. $^1$H NMR (400 MHz, CDCl$_3$) δ 5.83-5.95 (m, 1H), 5.02-5.11 (m, 2H), 5.59-5.62 (m, 1H), 3.81-3.90 (m, 2H), 3.53-3.77 (m, 7H), 3.31-3.36 (m, 1H), 2.24-2.36 (m, 1H), 1.78-1.95 (m, 3H), 1.64-1.73 (m, 2H), 1.19-1.22 (m, 6H).

Step 5: Synthesis of ({(1R)-1-[(2S)-tetrahydrofuran-2-yl]but-3-en-1-yl}oxy)acetaldehyde (C97)

(2S)-2-[(1R)-1-(2,2-Diethoxyethoxyl)but-3-en-1-yl]tetrahydrofuran (C95) was converted to the product using the method described for the synthesis of ({1-[(1R,2R)-2-methylcyclopropyl]but-3-en-1-yl}oxy)acetaldehyde (C83) in Example 20. The resulting product was used in the next step without further purification. Yield: 6 g, ≤33 mmol, ≤35%.

Step 6: Synthesis of N-hydroxy-2-({(1R)-1-[(2S)-tetrahydrofuran-2-yl]but-3-en-1-yl}oxy)ethanimine (C98)

({(1R)-1-[(2S)-Tetrahydrofuran-2-yl]but-3-en-1-yl}oxy)acetaldehyde (C97) was converted to the product using the method described for the synthesis of N-hydroxy-2-({1-[(1R,2R)-2-methylcyclopropyl]but-3-en-1-yl}oxy)ethanimine (C84) in Example 20. Yield: 4.7 g, 23.6 mmol, 65% over 2 steps from (C95).

Step 7: Synthesis of (3aR,5R)-5-[(2S)-tetrahydrofuran-2-yl]-3,3a,4,5-tetrahydro-7H-pyrano[3,4-c][1,2]oxazole (C99)

N-Hydroxy-2-({(1R)-1-[(2S)-tetrahydrofuran-2-yl]but-3-en-1-yl}oxy)ethanimine (C98) was converted to the product using the method described for the synthesis of 5-[(1R,2R)-2-methylcyclopropyl]-3,3a,4,5-tetrahydro-7H-pyrano[3,4-c][1,2]oxazole (C85) in Example 20. Yield: 2.6 g, 13 mmol, 54%. LCMS m/z 198.0 [M+H⁺]. ¹H NMR (400 MHz, CDCl₃) δ 4.73 (d, J=13.1 Hz, 1H), 4.61 (dd, J=10.0, 8.0 Hz, 1H), 4.19 (dd, J=13.6, 1 Hz, 1H), 3.72-3.89 (m, 4H), 3.38-3.48 (m, 2H), 2.35 (ddd, J=12.9, 6.4, 1.3 Hz, 1H), 1.78-2.02 (m, 4H), 1.44-1.53 (m, 1H).

Step 8: Synthesis of (3aR,5R,7aS)-7a-(2,4-difluorophenyl)-5-[(2S)-tetrahydrofuran-2-yl]hexahydro-1H-pyrano[3,4-c][1,2]oxazole (C100)

(3aR,5R)-5-[(2S)-Tetrahydrofuran-2-yl]-3,3a,4,5-tetrahydro-7H-pyrano[3,4-c][1,2]oxazole (C99) was converted to the product using the method described for the synthesis of 7a-(2,4-difluorophenyl)-5-[(1R,2R)-2-methylcyclopropyl]hexahydro-1H-pyrano[3,4-c][1,2]oxazole (C86) in Example 20. Yield: 1.4 g, 4.5 mmol, 36%. LCMS m/z 312.1 [M+H⁺]. ¹H NMR (400 MHz, CDCl₃) δ 7.89-7.95 (m, 1H), 6.87-6.91 (m, 1H), 6.77-6.83 (m, 1H), 6.29 (s, 1H), 4.10 (dd, J=12.5, 1.5 Hz, 1H), 3.72-3.92 (m, 5H), 3.53-3.57 (m, 2H), 3.07 (dt, J=11.4, 5.6 Hz, 1H), 1.79-2.03 (m, 5H), 1.46-1.55 (m, 1H).

Step 9: Synthesis of {(2R,4R,5S)-5-amino-5-(2,4-difluorophenyl)-2-[(2S)-tetrahydrofuran-2-yl]tetrahydro-2H-pyran-4-yl}methanol (C101)

To a solution of (C100) (1.20 g, 3.85 mmol) in acetonitrile/water (15:1, 30 mL) was added molybdenum hexacarbonyl (1.10 g, 4.16 mmol) in one portion and the reaction mixture was refluxed for 30 minutes. The reaction was then cooled to room temperature, at which point sodium borohydride (146 mg, 3.85 mmol) was added in one portion and the reaction was stirred at reflux for 2 hours. The reaction mixture was cooled to room temperature, filtered through a pad of Celite and washed with ethyl acetate (30 mL). The filtrate was concentrated in vacuo to provide the crude product as a dark oil that was used in the subsequent step without further purification. Yield: 1.3 g, ≤4.1 mmol, ≤107%.

Step 10: Synthesis of N-({(3S,4R,6R)-3-(2,4-difluorophenyl)-4-(hydroxymethyl)-6-[(2S)-tetrahydrofuran-2-yl]tetrahydro-2H-pyran-3-yl}carbamothioyl)benzamide (C102)

{(2R,4R,5S)-5-Amino-5-(2,4-difluorophenyl)-2-[(2S)-tetrahydrofuran-2-yl]tetrahydro-2H-pyran-4-yl}methanol (C101) was converted to the product using the method described for the synthesis of N-({(3S,4R,6R)-3-(2,4-difluorophenyl)-4-(hydroxymethyl)-6-[(1R,2R)-2-methylcyclopropyl]tetrahydro-2H-pyran-3-yl}carbamothioyl)benzamide (C90) in Example 20. Yield: 1.3 g, 2.7 mmol, 70% over 2 steps from (C100). LCMS m/z 477.2 [M+H⁺].

Step 11: Synthesis of N-{(4aR,6R,8aS)-8a-(2,4-difluorophenyl)-6-[(2S)-tetrahydrofuran-2-yl]-4,4a,5,6,8,8a-hexahydropyrano[3,4-d][1,3]thiazin-2-yl}benzamide (C103)

N-({(3S,4R,6R)-3-(2,4-Difluorophenyl)-4-(hydroxymethyl)-6-[(2S)-tetrahydrofuran-2-yl]tetrahydro-2H-pyran-3-yl}carbamothioyl)benzamide (C102) was converted to the product using the method described for the synthesis of N-[(4aR,6R,8aS)-6-[(benzyloxy)methyl]-8a-(2,4-difluorophenyl)- 4,4a,5,6,8,8a-hexahydropyrano[3,4-d][1,3]thiazin-2-yl]benzamide (C8) in Preparation P1. Yield: 1.0 g, 2.2 mmol, 87%. LCMS m/z 458.9 [M+H⁺].

Step 12: Synthesis of (4aR,6R,8aS)-8a-(2,4-difluorophenyl)-6-[(2S)-tetrahydrofuran-2-yl]-4,4a,5,6,8,8a-hexahydropyrano[3,4-d][1,3]thiazin-2-amine (21)

N-{(4aR,6R,8aS)-8a-(2,4-Difluorophenyl)-6-[(2S)-tetrahydrofuran-2-yl]-4,4a,5,6,8,8a-hexahydropyrano[3,4-d][1,3]thiazin-2-yl}benzamide (C103) was converted to the product using the method described for the synthesis of (4S,4aR,6R,8aS)-6-cyclopropyl-8a-(2,4-difluorophenyl)-4-(fluoromethyl)-4,4a,5,6,8,8a-hexahydropyrano[3,4-d][1,3]thiazin-2-amine, hydrochloride salt (6) in Example 6. Purification by reversed phase HPLC {Column: Phenomenex Gemini C18, 8 μm; Gradient: 36% to 56% acetonitrile in water [ammonia (pH 10)]} provided the product as a white solid. Yield: 193 mg, 0.545 mmol, 25%. LCMS m/z 355.1 [M+H⁺]. ¹H NMR (400 MHz, CDCl₃) δ 7.31-7.37 (m, 1H), 6.75-6.87 (m, 2H), 4.06 (dd, J=11, 2.0 Hz, 1H), 3.73-3.90 (m, 4H), 3.51 (ddd, J=10.8, 6.5, 2.3 Hz, 1H), 2.95 (dd, J=12.0, 4.0 Hz, 1H), 2.83-2.89 (m, 1H), 2.60 (dd, J=12.3, 2.3 Hz, 1H), 1.97-2.05 (m, 1H), 1.73-1.94 (m, 4H), 1.64-1.69 (m, 1H).

Biological Assays

BACE1 Cell-Free Assay:
Beta-secretase (BACE) is one of the enzymes involved in the generation of the amyloid beta peptide found in the amyloid plaques of Alzheimer's Disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY^EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a ½ log dose response curve from a top concentration of 100 μM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 μL assay buffer (100 mM sodium acetate, pH 4.5 (brought to pH with acetic acid), and 0.001% Tween-20). Plates are covered and incubated for 3 hours at 37° C. The reaction is stopped with the addition of 30 μL of 1.5 μM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

Whole Cell Assay (In Vitro sAPPb Assay):
H4 human neuroglioma cells over-expressing the wild-type human APP₆₉₅ are treated for 18 hours with compound in cell growth media having a final concentration 1% DMSO. sAPPβ. levels are measured using either TMB-ELISA or Pierce SuperSignal ELISA Pico Chemiluminescent Substrate (Pierce 37069) with capture APP N-terminal antibody (Affinity BioReagents, OMA1-03132), wild-type sAPPβ. specific reporter p192 (Elan), and tertiary anti rabbit-HRP (GE Healthcare).

BACE2 Assay:

This assay measures the inhibition of the BACE2 enzyme as it cleaves a non-native peptide. A synthetic substrate that can be cleaved by BACE2 having N-terminal biotin and made fluorescent by the covalent attachment of Oregon Green at the Cys residue is used to assay BACE2 activity in the presence or absence of the inhibitory compounds. The substrate is Biotin-KEISEISYEVEFR-C(Oregon green)-KK-OH. The BACE2 enzyme is available from Enzo Life Sciences (Cat # BML-SE550). Compounds are incubated in a ½ log dose response curve from a top concentration of 100 μM with BACE2 enzyme and the biotinylated fluorescent peptide in 384-well black plates (Thermo Scientific #4318). BACE2 is at a final concentration of 2.5 nM with a final concentration of peptide substrate of 150 nM in a reaction volume of 30 μL assay buffer (100 mM sodium acetate, pH 4.5 (brought to pH with acetic acid), and 0.001% Tween-20). Plates are covered and incubated for 3 hours at 37° C. The reaction is stopped with the addition of 30 μL of 1.5 μM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of BACE2 enzymatic cleavage of the synthetic substrate.

The biological assay data for Examples 1-18 are found below in Table 3:

TABLE 3

| Ex. # or Cpd. # | IUPAC name | BACE1 Cell-free Assay IC$_{50}$ (μM)$^a$ | sAPPβ Whole-Cell Assay IC$_{50}$ (nM)$^a$ | BACE2 Cell-free Assay IC$_{50}$ (μM) |
|---|---|---|---|---|
| 1 | (4aR,6R,8aS)-8a-(2,4-Difluorophenyl)-6-(tetrahydrofuran-2-yl)-4,4a,5,6,8,8a-hexahydropyrano[3,4-d][1,3]thiazin-2-amine, trifluoroacetate salt | 0.447 | 73.8 | 1.29$^b$ |
| 2 | (4aR,6R,8aS)-6-Cyclopropyl-8a-(2,4-difluorophenyl)-4,4a,5,6,8,8a-hexahydropyrano[3,4-d][1,3]thiazin-2-amine | 0.281$^c$ | 24.2$^c$ | 2.26$^b$ |
| C23 | (4aS,6S,8aR)-6-Cyclopropyl-8a-(2,4-difluorophenyl)-4,4a,5,6,8,8a-hexahydropyrano[3,4-d][1,3]thiazin-2-amine | >100 | 17,300 | N.D. |
| 3 | (4R,4aR,6R,8aS)-6-Cyclopropyl-8a-(2,4-difluorophenyl)-4-methyl-4,4a,5,6,8,8a-hexahydropyrano[3,4-d][1,3]thiazin-2-amine, trifluoroacetate salt | 0.337 | 38.9 | 2.49$^b$ |
| 4 | (4aR,6R,8aS)-8a-(2,4-Difluorophenyl)-6-(oxetan-2-yl)-4,4a,5,6,8,8a-hexahydropyrano[3,4-d][1,3]thiazin-2-amine | 1.31 | 137 | N.D.$^d$ |
| 5 | rel-(4S,4aR,6R,8aS)-6-Cyclopropyl-8a-(2,4-difluorophenyl)-4-(methoxymethyl)-4,4a,5,6,8,8a-hexahydropyrano[3,4-d][1,3]thiazin-2-amine, hydrochloride salt | 1.41 | 116 | N.D. |
| 6 | (4S,4aR,6R,8aS)-6-Cyclopropyl-8a-(2,4-difluorophenyl)-4-(fluoromethyl)-4,4a,5,6,8,8a-hexahydropyrano[3,4-d][1,3]thiazin-2-amine, hydrochloride salt | 0.346 | 39.1 | N.D. |
| C48 | (4R,4aS,6S,8aR)-6-Cyclopropyl-8a-(2,4-difluorophenyl)-4-(fluoromethyl)-4,4a,5,6,8,8a-hexahydropyrano[3,4-d][1,3]thiazin-2-amine, hydrochloride salt | >100 | >30,000 | N.D. |
| 7 | (4aR,6R,8aS)-8a-(2,4-Difluorophenyl)-6-(1-methylcyclopropyl)-4,4a,5,6,8,8a-hexahydropyrano[3,4-d][1,3]thiazin-2-amine | 0.484 | 142 | N.D. |
| C61 | (4aS,6S,8aR)-8a-(2,4-Difluorophenyl)-6-(1-methylcyclopropyl)-4,4a,5,6,8,8a-hexahydropyrano[3,4-d][1,3]thiazin-2-amine | 37,000 | 2,890 | N.D. |
| 8 | (4aR,6S,8aS)-6-(Cyclopropylmethyl)-8a-(2,4-difluorophenyl)-4,4a,5,6,8,8a-hexahydropyrano[3,4-d][1,3]thiazin-2-amine | 0.235 | 61.2 | N.D. |
| C74 | (4aS,6R,8aR)-6-(Cyclopropylmethyl)-8a-(2,4-difluorophenyl)-4,4a,5,6,8,8a-hexahydropyrano[3,4-d][1,3]thiazin-2-amine | >86,000 | 7,400 | N.D. |
| 9 | (4aR,6R,8aS)-6-Cyclopropyl-8a-(2,4,6-trifluorophenyl)-4,4a,5,6,8,8a-hexahydropyrano[3,4-d][1,3]thiazin-2-amine | 1.052 | 57.2 | N.D. |
| 10 | (4aR,6R,8aS)-6-Cyclopropyl-8a-(4-fluorophenyl)-4,4a,5,6,8,8a-hexahydropyrano[3,4-d][1,3]thiazin-2-amine | 0.572 | 89.7 | N.D. |
| 11 | (4aR,6R,8aS)-6-Cyclopropyl-8a-(2,5-difluorophenyl)-4,4a,5,6,8,8a-hexahydropyrano[3,4-d][1,3]thiazin-2-amine | 1.42 | 85.1 | N.D. |
| 12 | (4aR,6R,8aS)-6-Cyclopropyl-8a-(2,6-difluorophenyl)-4,4a,5,6,8,8a-hexahydropyrano[3,4-d][1,3]thiazin-2-amine | 0.395 | 34.6 | N.D. |

TABLE 3-continued

| Ex. # or Cpd. # | IUPAC name | BACE1 Cell-free Assay IC$_{50}$ (µM)[a] | sAPPβ Whole-Cell Assay IC$_{50}$ (nM)[a] | BACE2 Cell-free Assay IC$_{50}$ (µM) |
|---|---|---|---|---|
| 13 | (4aR,6R,8aS)-6-Cyclopropyl-8a-(2-fluorophenyl)-4,4a,5,6,8,8a-hexahydropyrano[3,4-d][1,3]thiazin-2-amine | 0.422 | 40.0 | N.D. |
| 14 | (4aR,6R,8aS)-6-Cyclopropyl-8a-phenyl-4,4a,5,6,8,8a-hexahydropyrano[3,4-d][1,3]thiazin-2-amine | 1.28 | 142 | N.D. |
| 15 | (4aR,6R,8aS)-6-Cyclopropyl-8a-(2-fluoro-4-methylphenyl)-4,4a,5,6,8,8a-hexahydropyrano[3,4-d][1,3]thiazin-2-amine | 0.715 | 72.1 | N.D. |
| 16 | (4aR,6R,8aS)-6-Cyclopropyl-8a-(3-fluoro-4-methylphenyl)-4,4a,5,6,8,8a-hexahydropyrano[3,4-d][1,3]thiazin-2-amine | 0.897 | 92.3 | N.D. |
| 17 | (4aS,6S,8aR)-6-Cyclopropyl-8a-(2-fluorophenyl)-4,4a,5,6,8,8a-hexahydropyrano[3,4-d][1,3]thiazin-2-amine | 25.71 | 1,561 | N.D. |
| 18 | (4aS,6S,8aR)-6-Cyclopropyl-8a-(4-fluorophenyl)-4,4a,5,6,8,8a-hexahydropyrano[3,4-d][1,3]thiazin-2-amine | 15.63 | 2,224 | N.D. |
| 19 | (4aR,6R,8aS)-8a-(2,4-Difluorophenyl)-6-((R)-5,5-dimethyltetrahydrofuran-2-yl)-4,4a,5,6,8,8a-hexahydropyrano[3,4-d][1,3]thiazin-2-amine | 0.184 | 17.9 | N.D. |
| 20 | (4aR,6R,8aS)-8a-(2,4-Difluorophenyl)-6-[(1R,2R)-2-methylcyclopropyl]-4,4a,5,6,8,8a-hexahydropyrano[3,4-d][1,3]thiazin-2-amine | 0.116 | 16.2 | N.D. |
| 21 | (4aR,6R,8aS)-8a-(2,4-Difluorophenyl)-6-[(2S)-tetrahydrofuran-2-yl]-4,4a,5,6,8,8a-hexahydropyrano[3,4-d][1,3]thiazin-2-amine | 0.302 | 39.7 | N.D. |

[a]Reported IC$_{50}$ values are the geometric mean of 2-3 determinations.
[b]IC$_{50}$ value is from a single determination.
[c]IC$_{50}$ value represents the geometric mean of ≥6 determinations.
[d]Not determined

We claim:
1. A compound of formula (I)

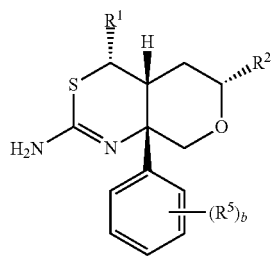

I or a tautomer thereof or a pharmaceutically acceptable salt of said compound or tautomer, wherein:
$R^1$ is selected from hydrogen, —CH$_3$, —CH$_2$F, —CHF$_2$, —CF$_3$, or —CH$_2$OCH$_3$;
$R^2$ is —(C(R$^{3a}$)(R$^{3b}$))$_m$—(C$_3$-C$_6$)cycloalkyl or —(C(R$^{3a}$)(R$^{3b}$))$_m$-(4- to 10-membered) heterocycloalkyl having one to three heteroatoms independently selected from N, O or S, wherein said N is optionally substituted with $R^4$; and wherein each available carbon position of said (C$_3$-C$_6$)cycloalkyl moiety or said (4- to 10-membered)heterocycloalkyl moiety is optionally substituted with one to two $R^6$;
$R^{3a}$ and $R^{3b}$ are each independently hydrogen, fluoro, or (C$_1$-C$_6$)alkyl; wherein said (C$_1$-C$_6$)alkyl is optionally substituted with one to three fluoro;
$R^4$ is selected from (C$_1$-C$_6$)alkyl, (C$_1$-C$_6$)alkylcarbonyl, (C$_3$-C$_6$)cycloalkylcarbonyl or (C$_1$-C$_6$)alkylcarbonyl(C$_1$-C$_6$)alkyl; wherein said (C$_1$-C$_6$)alkyl moiety, said (C$_1$-C$_6$)alkylcarbonyl moiety and said (C$_1$-C$_6$)alkylcarbonyl(C$_1$-C$_6$)alkyl moiety are optionally substituted with one to three fluoro;
$R^5$ at each occurrence is independently halogen, (C$_1$-C$_3$)alkyl, and (C$_1$-C$_3$)alkoxy, wherein said (C$_1$-C$_3$)alkyl moiety and said (C$_1$-C$_3$)alkoxy are optionally substituted with one to three fluoro;
$R^6$ at each occurrence is independently halogen, —OH, —CN, (C$_1$-C$_6$)alkyl, and (C$_1$-C$_6$)alkoxy, wherein said (C$_1$-C$_6$)alkyl or (C$_1$-C$_6$)alkoxy is optionally substituted with one to three fluoro;
m is 0, 1, or 2; and
b is 0, 1, 2, 3, 4, or 5.

2. The compound of claim 1, or a tautomer thereof or a pharmaceutically acceptable salt of said compound or tautomer, wherein $R^2$ is —(C(R$^{3a}$)(R$^{3b}$))$_m$—(C$_3$-C$_6$)cycloalkyl; wherein said (C$_3$-C$_6$)cycloalkyl moiety is optionally substituted with one to three $R^6$; $R^5$ at each occurrence is independently fluoro or methyl, wherein said methyl moiety is optionally substituted with one to three fluoro; $R^6$ at each occurrence is independently fluoro or methyl, wherein said methyl moiety is optionally substituted with one to three fluoro; m is 0 or 1; and b is 0, 1, 2, or 3.

3. The compound of claim 2, or a tautomer thereof or a pharmaceutically acceptable salt of said compound or tautomer, wherein $R^2$ is cyclopropyl.

4. The compound of claim 3, or a tautomer thereof or a pharmaceutically acceptable salt of said compound or tautomer, wherein said compound is selected from the group consisting of:
(4aR,6R,8aS)-6-Cyclopropyl-8a-(2,4-difluorophenyl)-4,4a,5,6,8,8a-hexahydropyrano[3,4-d][1,3]thiazin-2-amine;

(4R,4aR,6R,8aS)-6-Cyclopropyl-8a-(2,4-difluorophenyl)-4-methyl-4,4a,5,6,8,8a-hexahydropyrano[3,4-d][1,3]thiazin-2-amine;
rel-(4S,4aR,6R,8aS)-6-Cyclopropyl-8a-(2,4-difluorophenyl)-4-(methoxymethyl)-4,4a,5,6,8,8a-hexahydropyrano[3,4-d][1,3]thiazin-2-amine;
(4S,4aR,6R,8aS)-6-Cyclopropyl-8a-(2,4-difluorophenyl)-4-(fluoromethyl)-4,4a,5,6,8,8a-hexahydropyrano[3,4-d][1,3]thiazin-2-amine;
(4aR,6R,8aS)-8a-(2,4-Difluorophenyl)-6-(1-methylcyclopropyl)-4,4a,5,6,8,8a-hexahydropyrano[3,4-d][1,3]thiazin-2-amine;
(4aR,6R,8aS)-6-Cyclopropyl-8a-(2,4,6-trifluorophenyl)-4,4a,5,6,8,8a-hexahydropyrano[3,4-d][1,3]thiazin-2-amine;
(4aR,6R,8aS)-6-Cyclopropyl-8a-(4-fluorophenyl)-4,4a,5,6,8,8a-hexahydropyrano[3,4-d][1,3]thiazin-2-amine;
(4aR,6R,8aS)-6-Cyclopropyl-8a-(2,5-difluorophenyl)-4,4a,5,6,8,8a-hexahydropyrano[3,4-d][1,3]thiazin-2-amine;
(4aR,6R,8aS)-6-Cyclopropyl-8a-(2,6-difluorophenyl)-4,4a,5,6,8,8a-hexahydropyrano[3,4-d][1,3]thiazin-2-amine;
(4aR,6R,8aS)-6-Cyclopropyl-8a-(2-fluorophenyl)-4,4a,5,6,8,8a-hexahydropyrano[3,4-d][1,3]thiazin-2-amine;
(4aR,6R,8aS)-6-Cyclopropyl-8a-phenyl-4,4a,5,6,8,8a-hexahydropyrano[3,4-d][1,3]thiazin-2-amine;
(4aR,6R,8aS)-6-Cyclopropyl-8a-(2-fluoro-4-methylphenyl)-4,4a,5,6,8,8a-hexahydropyrano[3,4-d][1,3]thiazin-2-amine; and
(4aR,6R,8aS)-6-Cyclopropyl-8a-(3-fluoro-4-methylphenyl)-4,4a,5,6,8,8a-hexahydropyrano[3,4-d][1,3]thiazin-2-amine.

5. The compound of claim 2, or a tautomer thereof or a pharmaceutically acceptable salt of said compound or tautomer, wherein $R^2$ is cyclopropylmethyl.

6. The compound of claim 5, or a tautomer thereof or a pharmaceutically acceptable salt of said compound or tautomer, wherein said compound is
(4aR,6S,8aS)-6-(Cyclopropylmethyl)-8a-(2,4-difluorophenyl)-4,4a,5,6,8,8a-hexahydropyrano[3,4-d][1,3]thiazin-2-amine.

7. The compound of claim 1, or a tautomer thereof or a pharmaceutically acceptable salt of said compound or tautomer, wherein $R^2$ is —(C($R^{3a}$)($R^{3b}$))$_m$-(4- to 10-membered)heterocycloalkyl; said (4- to 10-membered)heterocycloalkyl is optionally substituted with one to three $R^6$; $R^5$ at each occurrence is independently fluoro or methyl, wherein said methyl is optionally substituted with one to three fluoro; $R^6$ at each occurrence is independently fluoro or methyl, wherein said methyl is optionally substituted with one to three fluoro; m is 0 or 1; and b is 0, 1, 2, or 3.

8. The compound of claim 7, or a tautomer thereof or a pharmaceutically acceptable salt of said compound or tautomer, wherein m is 0;
and wherein said (4- to 10-membered)heterocycloalkyl moiety is selected from oxetanyl or tetrahydrofuranyl.

9. The compound of claim 8, or a tautomer thereof or a pharmaceutically acceptable salt of said compound or tautomer, wherein said (4- to 10-membered)heterocycloalkyl is oxetanyl.

10. The compound of claim 9, or a tautomer thereof or a pharmaceutically acceptable salt of said compound or tautomer, wherein said compound is:
(4aR,6R,8aS)-8a-(2,4-Difluorophenyl)-6-(oxetan-2-yl)-4,4a,5, 6, 8,8a-hexahydropyrano[3, 4-d][1, 3]thiazin-2-amine.

11. The compound of claim 8, or a tautomer thereof or a pharmaceutically acceptable salt of said compound or tautomer, wherein said (4- to 10-membered)heterocycloalkyl is tetrahydrofuranyl.

12. The compound of claim 11, or a tautomer thereof or a pharmaceutically acceptable salt of said compound or tautomer, wherein said compound is:
(4aR,6R,8aS)-8a-(2,4-Difluorophenyl)-6-(tetrahydrofuran-2-yl)-4,4a,5,6,8,8a-hexahydropyrano[3, 4-d][1, 3]thiazin-2-amine.

13. A compound of formula Ic:

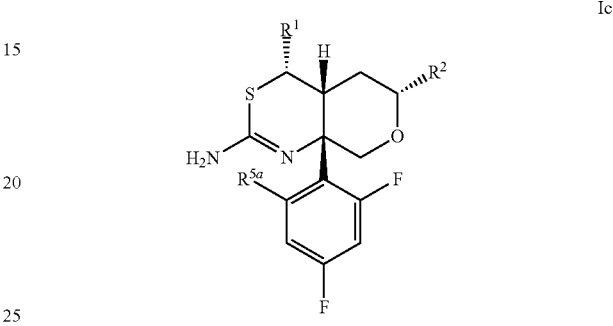

Ic or a tautomer thereof or a pharmaceutically acceptable salt of said compound or tautomer, wherein:
$R^1$ is hydrogen, —CH$_3$, —CH$_2$F, or —CH$_2$OCH$_3$;
$R^2$ is —(C($R^{3a}$)($R^{3b}$))$_m$—(C$_3$-C$_6$)cycloalkyl or —(C($R^{3a}$)($R^{3b}$))$_m$-(4- to 5-membered)heterocycloalkyl having one to two heteroatoms independently selected from N, O or S, wherein said N is optionally substituted with $R^4$;
$R^{3a}$ and $R^{3b}$ each independently hydrogen, fluoro, or (C$_1$-C$_6$)alkyl; wherein said (C$_1$-C$_6$)alkyl is optionally substituted with one to three fluoro;
$R^4$ is (C$_1$-C$_3$)alkyl; and wherein said (C$_3$-C$_6$)cycloalkyl moiety or said (4- to 5-membered)heterocycloalkyl moiety is optionally substituted with one to three $R^6$;
$R^{5a}$ is hydrogen, fluoro or methyl;
$R^6$ at each occurrence is independently (C$_1$-C$_3$)alkyl; and
m is 0 or 1.

14. The compound of claim 13, or a tautomer thereof or a pharmaceutically acceptable salt of said compound or tautomer, wherein $R^2$ is cyclopropyl optionally substituted with methyl; and $R^{5a}$ is hydrogen.

15. The compound according to claim 14, or a tautomer thereof or a pharmaceutically acceptable salt of said compound or tautomer, wherein $R^{5a}$ is fluoro.

16. A compound of formula Id:

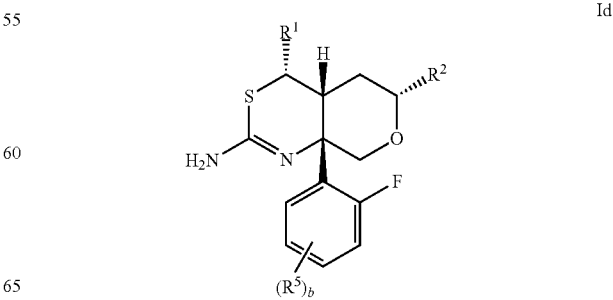

Id or a tautomer thereof or a pharmaceutically acceptable salt of said compound or tautomer, wherein:

$R^1$ is hydrogen;

$R^2$ is $-(C(R^{3a})(R^{3b}))_m-(C_3-C_6)$cycloalkyl or $-(C(R^{3a})(R^{3b}))_m$-(4- to 5-membered)heterocycloalkyl having at least one to two heteroatoms selected from N, O or S, wherein said N is optionally substituted with $R^4$;

$R^{3a}$ and $R^{3b}$ are each independently hydrogen fluoro or $C_1-C_6$ alkyl; wherein said $(C_1-C_6)$alkyl is optionally substituted with one to three fluoro;

$R^4$ is $(C_1-C_3)$alkyl; wherein said $(C_3-C_6)$cycloalkyl moiety or said (4- to 5-membered)heterocycloalkyl moiety is optionally substituted with one to three $R^6$;

$R^5$ is halogen or $(C_1-C_3)$alkyl;

$R^6$ is $(C_1-C_3)$alkyl;

m is 0, 1 or 2; and b is 0 or 1.

17. A pharmaceutical composition comprising a therapeutically effective amount of a compound of claim 1, or a tautomer thereof or a pharmaceutically acceptable salt of said compound or tautomer, and a pharmaceutically acceptable excipient.

18. A method of treating Alzheimer's disease in a patient, the method comprising administering a therapeutically effective amount of a compound of claim 1, or a tautomer thereof or a pharmaceutically acceptable salt of said compound or tautomer, to a patient in need thereof.

19. A method of treating type 2 diabetes or obesity in a patient, the method comprising administering a therapeutically effective amount of a compound of claim 1, or a tautomer thereof or a pharmaceutically acceptable salt of said compound or tautomer, to a patient in need thereof.

* * * * *